(12) United States Patent
Yang et al.

(10) Patent No.: US 9,828,375 B2
(45) Date of Patent: Nov. 28, 2017

(54) 4-POSITION SUBSTITUTED PYRAZOLOPYRIMIDINE DERIVATIVE, AND USE THEREOF IN DRUG PREPARATION

(71) Applicant: Guangxi Wuzhou Pharmaceuticals (Group) Co., Ltd., Guangxi (CN)

(72) Inventors: Shengyong Yang, Sichuan (CN); Yuquan Wei, Sichuan (CN)

(73) Assignee: Guangxi Wuzhou Pharmaceuticals (Group) Co., Ltd., Guangxi (CN)

( * ) Notice: Subject to any disclaimer, the term of this patent is extended or adjusted under 35 U.S.C. 154(b) by 0 days.

(21) Appl. No.: 14/417,588

(22) PCT Filed: Mar. 5, 2013

(86) PCT No.: PCT/CN2013/072185
§ 371 (c)(1),
(2) Date: Jan. 27, 2015

(87) PCT Pub. No.: WO2014/015673
PCT Pub. Date: Jan. 30, 2014

(65) Prior Publication Data
US 2015/0315191 A1    Nov. 5, 2015

(30) Foreign Application Priority Data
Jul. 27, 2012    (CN) .......................... 2012 1 0264034

(51) Int. Cl.
*A61K 31/519*    (2006.01)
*C07D 487/04*    (2006.01)

(52) U.S. Cl.
CPC ................. *C07D 487/04* (2013.01)

(58) Field of Classification Search
CPC .................................................. C07D 487/04
See application file for complete search history.

(56) References Cited

U.S. PATENT DOCUMENTS

2008/0275054 A1    11/2008    Holzer et al.

FOREIGN PATENT DOCUMENTS

| WO | 03099820 | A1 | 12/2003 |
| WO | 2004106339 | A2 | 12/2004 |
| WO | 2005047288 | A1 | 5/2005 |

OTHER PUBLICATIONS

Yang et al. Structure-Activity Relationship Studies of Pyrazolo[3,4-d]pyrimidine Derivatives Leading to the Discovery of a Novel Multikinase Inhibitor That Potently Inhibits FLT3 and VEGFR2 and Evaluation of Its Activity against Acute Myeloid Leukemia in Vitro and in Vivo Journal of Medicinal Chemistry (2013), 56(4), 1641-1655.*

STN CAS Registry Structures, 2008-2011.*

International Search Report and Written Opinion issued in corresponding International Patent Application No. PCT/CN2013/072185 dated Jun. 13, 2013 (11 pages) (English Translation).

Yang et al., "Structure-Activity Relationship Studies of Pyrazolo [3,4-d] pyrimidine Derivatives Leading to the Discovery of a Novel Multikinase Inhibitor That Potently Inhibits FLT3 and VEGFR2 and Evaluation of Its Activity against Acute Myeloid Leukemia in Vitro and in Vivo", Journal of Medicinal Chemistry, vol. 56, No. 4, Jan. 30, 2013, pp. 1641-1655.

Extended European Search Report issued in corresponding European Patent Application No. 13822476.1 dated May 3, 2016 (8 pages).

* cited by examiner

*Primary Examiner* — Brian McDowell
(74) *Attorney, Agent, or Firm* — Kilyk & Bowersox, P.L.L.C.

(57) ABSTRACT

The invention belongs to the technical field of organic synthetic drugs, and particularly relates to a pyrazolopyrimidine derivative and a preparation method and medical uses thereof. The invention provides a new pyrazolopyrimidine derivative mainly having position 4 substituted, i.e., position substituted by Y in formula I. The pyrazolopyrimidine derivative of the invention has a structural formula I as follows:

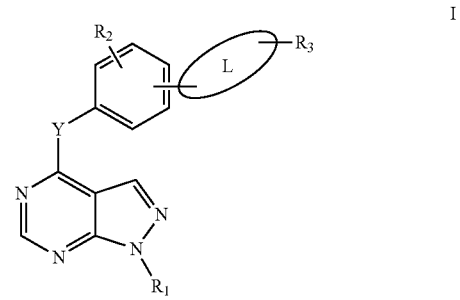

The invention provides a new pyrazolopyrimidine derivative and a simple, efficient and low-cost preparation method thereof. The pyrazolopyrimidine derivative of the invention has good inhibitory activity for multiple kinases, has inhibitory action on multiple solid tumors, leukemia and autoimmune diseases, provides a new effective choice for preparation of kinase inhibitors, medicines for autoimmune diseases, angiogenesis inhibitors and antitumor drugs, and has good application prospect.

60 Claims, 4 Drawing Sheets

4-POSITION SUBSTITUTED PYRAZOLOPYRIMIDINE DERIVATIVE, AND USE THEREOF IN DRUG PREPARATION

The present application is a National Stage Application of PCT/CN2013/072185, filed Mar. 5, 2013, which claims priority from Chinese Patent Application No. 201210264034.2, filed Jul. 27, 2012.

FIELD OF THE INVENTION

The invention belongs to the technical field of organic synthetic drugs, and particularly relates to a pyrazolopyrimidine derivative and a preparation method and uses thereof in pharmaceutical preparation. The pyrazolopyrimidine derivative mainly has position 4 substituted.

DESCRIPTION OF THE RELATED ART

Kinases are widely distributed in organisms and play an essential role in regulating cell proliferation, growth, differentiation, apoptosis, ageing, etc. Abnormal activities of kinases may cause many major diseases including cancer, autoimmune diseases (e.g. lupus erythematosus, rheumatic arthritis and psoriasis), diabetes and inflammation. Therefore, as a kind of the most important disease treatment target, kinases are being studied intensively.

According to human gene map, 518 kinases have been identified in human beings. The relations between kinases and tumor and autoimmune diseases have been clarified. For example, the receptor tyrosine kinase of vascular endothelial growth factor receptor 2 (VEGFR2) and platelet derived growth factor receptor (PDGFR) is involved in the regulation of new blood vessels. This angiogenesis plays an important role in body development, wound healing, tissue regeneration and other physiological processes, and is also an important participant in pathological processes including tumor. The purpose of oncotherapy can be achieved by inhibiting angiogenesis of tumor tissues and further blocking nutrition supply of tumors. Fms-like tyrosine kinase 3 (FLT3) is another receptor tyrosine kinase and plays an important role in proliferation and differentiation of hemopoietic stem cells. According to molecular biological study in recent years, FLT3 mutation or high expression occurs to hemopoietic stem cells among about a third of acute myelogenous leukemia (AML) patients. Many studies have shown that AML patients with FLT3 mutation are prone to recurrence and poor prognosis. At present, FLT3 is an important treatment target for AML and its inhibitor is known as the most perspective molecular targeted drug for treating AML. A few FLT3 inhibitors such as SU-5416, PKC-412 and CEP-701 have been used in clinical trials. However, the latest studies have found that clinical trials of these compounds are not ideal, and one of the main reasons is that their large toxic and side effects limit the increase of drug dose and further affect the efficacy. Therefore, it is particularly important to research and develop FLT3 inhibitor with high efficacy and low toxicity for AML treatment. In addition, tumors are closely related to other kinases such as human Fms-like tyrosine kinase 1 (FLT1), human Fms-like tyrosine kinase 4 (FLT4), BRAF serine/threonine protein kinase (BRAF), cRAF serine/threonine protein kinase (cRAF), fibroblast growth factor receptor (FGFR1), RET receptor tyrosine kinase (RET), SRC tyrosine kinase (SRC), EphA2 tyrosine kinase (EphA2), EphB2 tyrosine kinase (EphB2), c-KIT, CDK1 and tyrosine protein kinase (KIT).

Recent studies have identified that FLT3 is related to not only acute myeloid leukemia but also autoimmune diseases including systemic lupus erythematosus, rheumatic arthritis, psoriasis, multiple sclerosis, inflammatory-immune disease, etc. FLT3 is highly expressed in progenitor cells of dendritic cells (DC), and FLT3 ligand can induce DC differentiation and maturation. Besides, FLT3 is also highly expressed in mature dendritic cells, which suggests that FLT3 signal path plays an important role in maintaining normal DC function. DCs are a kind of key participant of the human immune system, and abnormal regulation of DCs is an important reason for leading autoimmune diseases. In recent years, studies have shown that FLT3 activation can be inhibited to regulate DC differentiation and maturation, thus achieving the purpose of treating autoimmune diseases. Therefore, highly active FLT3 inhibitor can be used for AML treatment and is particularly important for treating autoimmune diseases.

Traditionally, highly selective kinase inhibitor of single kinase is mainly focused on in terms of research and development of kinase drugs. However, for complex diseases such as tumor and autoimmune diseases, multi-target drugs targeting at multiple kinases may have more advantages in terms of efficacy and recurrence prevention.

SUMMARY OF THE INVENTION

The invention provides a new pyrazolopyrimidine derivative mainly having position 4 substituted. The pyrazolopyrimidine derivative of the invention has a structural formula I as follows:

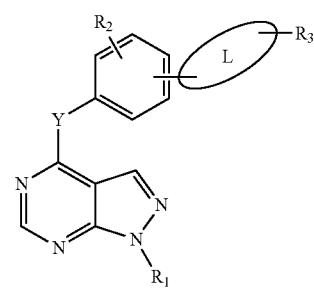

wherein, Y is nitrogen, oxygen or sulfur; and L is

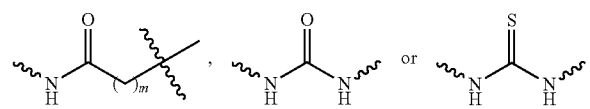

substituted at 3-position or 4-position on the benzene ring of the matrix; wherein one end of atom N is connected with the matrix;

$R_1$ is —H, $C_1$-$C_6$ alkyl,

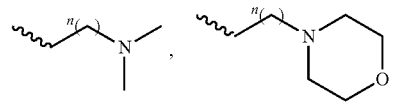

or substituted 6-10 membered aromatic ring substituted methyl; and the substituent on the substituted aromatic ring is —H, halogen or $C_1$-$C_4$ alkyl;
$R_2$ is —H, halogen, $C_1$-$C_4$ alkyl, $C_1$-$C_4$ alkoxy, $C_1$-$C_4$ alkyl sulfenyl or —$NO_2$;
$R_3$ is substituted 4-12 membered aromatic heterocyclic radical,

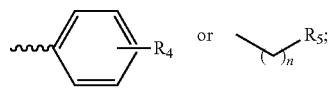

the number of heteroatoms on the substituted aromatic heterocyclic radical is 1 to 4, the heteroatom is N, O or S; the substituent on the substituted heteroaromatic ring is —H, $C_1$-$C_6$ alkyl, substituted aryl, —$CF_3$, 5-10 membered aromatic heterocyclic radical, carboxyl or $C_3$-$C_6$ cycloalkyl; and the substituent on the substituted aryl is —H or halogen;
$R_4$ is —H, halogen, $C_1$-$C_4$ alkyl, $C_1$-$C_4$ alkoxy, —$CF_3$, —$OCF_3$, morpholinyl or $C_1$-$C_4$ phenylalkyl;
$R_5$ is —H, aryl or $C_3$-$C_8$ cycloalkyl;
m=0-2; and
n=0-4.

Preferably, Y is nitrogen, oxygen or sulfur; and L is

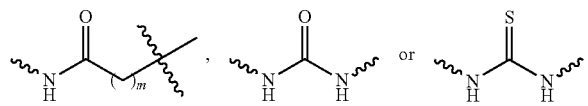

substituted at 3-position or 4-position on the benzene ring of the matrix; wherein one end of atom N is connected with the benzene ring of the matrix;
$R_1$ is —H, $C_1$-$C_6$ alkyl,

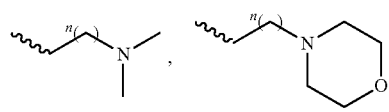

or substituted 6-10 membered aromatic ring substituted methyl; and the substituent on the substituted aromatic ring is —H, halogen or $C_1$-$C_4$ alkyl;
$R_2$ is —H, halogen, $C_1$-$C_4$ alkyl, $C_1$-$C_4$ alkoxy, $C_1$-$C_4$ alkyl sulfenyl or —$NO_2$;
$R_3$ is substituted 4-12 membered aromatic heterocyclic radical,

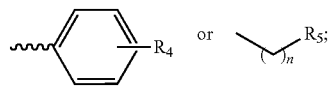

the substituent on the substituted heteroaromatic ring is —H, $C_1$-$C_6$ alkyl, aryl, —$CF_3$ or 5-10 membered aromatic heterocyclic radical; and the number of heteroatoms on the aromatic heterocyclic radical is 1 to 4, and the heteroatom is N, O or S;
$R_4$ is —H, halogen, $C_1$-$C_4$ alkyl, $C_1$-$C_4$ alkoxy, —$CF_3$, —$OCF_3$, morpholinyl or $C_1$-$C_4$ phenylalkyl;
$R_5$ is —H, aryl or $C_3$-$C_8$ cycloalkyl;
m=0-2; and
n=0-4.

Preferably, Y is nitrogen, oxygen or sulfur; and L is

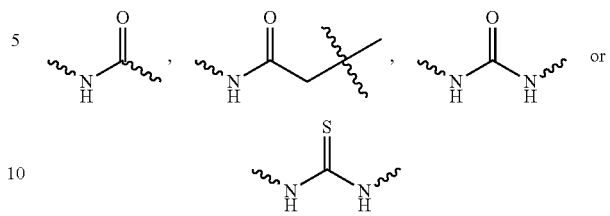

substituted at 3-position or 4-position on the benzene ring of the matrix; wherein one end of atom N is connected with the benzene ring of the matrix;
$R_1$ is —H, $C_1$-$C_4$ alkyl,

or substituted 6-10 membered aromatic ring substituted methyl; and the substituent on the substituted aromatic ring is —H, halogen or $C_1$-$C_4$ alkyl;
$R_2$ is —H, halogen, $C_1$-$C_4$ alkyl, $C_1$-$C_4$ alkoxy, $C_1$-$C_4$ alkyl sulfenyl or —$NO_2$;
$R_3$ is substituted 4-12 membered aromatic heterocyclic radical,

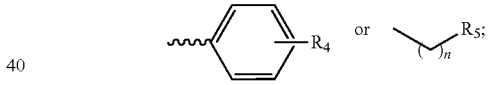

the substituent on the substituted heteroaromatic ring is —H, $C_1$-$C_6$ alkyl, aryl, —$CF_3$ or 5-10 membered aromatic heterocyclic radical; and the number of heteroatoms on the aromatic heterocyclic radical is 1 to 4, and the heteroatom is N, O or S;
$R_4$ is —H, halogen, $C_1$-$C_4$ alkyl, $C_1$-$C_4$ alkoxy, —$CF_3$, —$OCF_3$, morpholinyl or $C_1$-$C_4$ phenylalkyl;
$R_5$ is —H, aryl or $C_3$-$C_8$ cycloalkyl; and
n=0-4.

Further preferably, Y is nitrogen, oxygen or sulfur; and L is

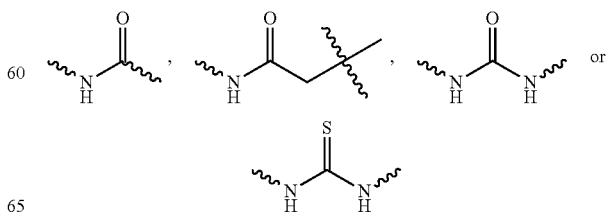

substituted at 3-position or 4-position on the benzene ring of the matrix; wherein one end of atom N is connected with the benzene ring of the matrix;
$R_1$ is —H, $C_1$-$C_4$ alkyl,

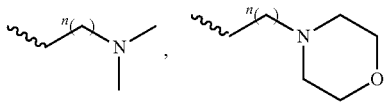

or substituted 6-10 membered aromatic ring substituted methyl; and the substituent on the substituted aromatic ring is —H, halogen or $C_1$-$C_4$ alkyl;
$R_2$ is —H, halogen, $C_1$-$C_4$ alkyl, $C_1$-$C_4$ alkoxy or —$NO_2$;
$R_3$ is substituted 4-12 membered aromatic heterocyclic radical,

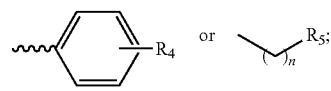

the substituent on the substituted heteroaromatic ring is —H, $C_1$-$C_6$ alkyl, aryl, —$CF_3$ or 5-10 membered aromatic heterocyclic radical; and the number of heteroatoms on the aromatic heterocyclic radical is 1 to 4, and the heteroatom is N, O or S;
$R_4$ is —H, halogen, $C_1$-$C_4$ alkyl, $C_1$-$C_4$ alkoxy, —$CF_3$, —$OCF_3$, morpholinyl or $C_1$-$C_4$ phenylalkyl;
$R_5$ is H, aryl or $C_3$-$C_8$ cycloalkyl; and
n=0-4.

Preferably, Y is nitrogen, oxygen or sulfur; and L

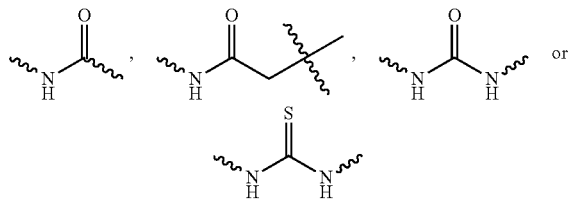

substituted at 3-position or 4-position on the benzene ring of the matrix; wherein one end of atom N is connected with the benzene ring of the matrix;
$R_1$ is —H, $C_1$-$C_4$ alkyl,

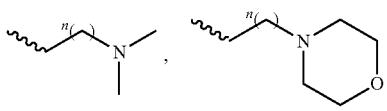

or substituted phenyl substituted methyl; and the substituent of the substituted phenyl is —H, halogen or $C_1$-$C_4$ alkyl;
$R_2$ is —H, halogen, $C_1$-$C_4$ alkyl, $C_1$-$C_4$ alkoxy or —$NO_2$;
$R_3$ is substituted 4-12 membered aromatic heterocyclic radical,

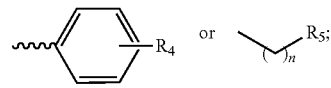

the substituent on the substituted heteroaromatic ring is —H, $C_1$-$C_6$ alkyl, aryl, —$CF_3$ or 5-10 membered aromatic heterocyclic radical; and the number of heteroatoms on the aromatic heterocyclic radical is 1 to 4, and the heteroatom is N, O or S;
$R_4$ is —H, halogen, $C_1$-$C_4$ alkyl, $C_1$-$C_4$ alkoxy, —$CF_3$, —$OCF_3$, morpholinyl or $C_1$-$C_4$ phenylalkyl;
$R_5$ is —H, aryl or $C_3$-$C_8$ cycloalkyl; and
n=0-3.

Preferably, Y is nitrogen, oxygen or sulfur; and L is

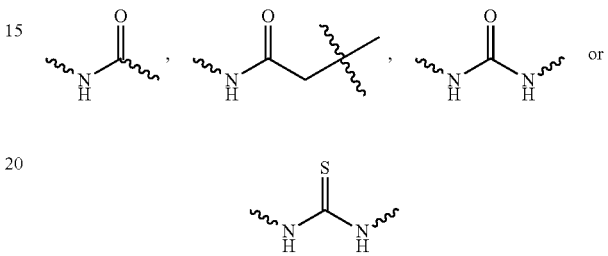

substituted at 3-position or 4-position on the benzene ring of the matrix; wherein one end of atom N is connected with the benzene ring of the matrix;
$R_1$ is —H, $C_1$-$C_4$ alkyl,

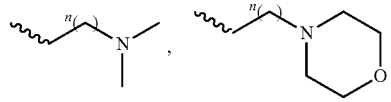

or substituted phenyl substituted methyl; and the substituent of the substituted phenyl is —H, —F, —Cl or —Br;
$R_2$ is —H, halogen, $C_1$-$C_4$ alkyl, $C_1$-$C_4$ alkoxy or —$NO_2$;
$R_3$ is substituted 4-12 membered aromatic heterocyclic radical,

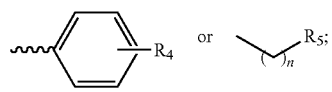

the substituent on the substituted heteroaromatic ring is —H, $C_1$-$C_6$ alkyl, aryl, —$CF_3$ or 5-10 membered aromatic heterocyclic radical; and the number of heteroatoms on the aromatic heterocyclic radical is 1 to 4, and the heteroatom is N, O or S;
$R_4$ is —H, halogen, $C_1$-$C_4$ alkyl, $C_1$-$C_4$ alkoxy, —$CF_3$, —$OCF_3$, morpholinyl or $C_1$-$C_4$ phenylalkyl;
$R_5$ is —H, aryl or $C_3$-$C_8$ cycloalkyl; and
n=0-3.

Preferably, Y is nitrogen, oxygen or sulfur; and L is

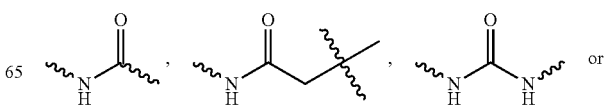

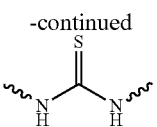

substituted at 3-position or 4-position on the benzene ring of the matrix; wherein one end of atom N is connected with the benzene ring of the matrix;

$R_1$ is —H, $C_1$-$C_4$ alkyl,

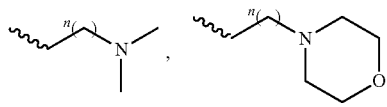

or substituted phenyl substituted methyl; and the substituent of the substituted phenyl is —H or —Br;

$R_2$ is —H, halogen, $C_1$-$C_4$ alkyl, $C_1$-$C_4$ alkoxy or —NO$_2$;

$R_3$ is substituted 4-12 membered aromatic heterocyclic radical,

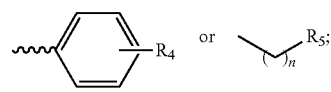

the substituent on the substituted heteroaromatic ring is —H, $C_1$-$C_6$ alkyl, aryl, —CF$_3$ or 5-10 membered aromatic heterocyclic radical; and the number of heteroatoms on the aromatic heterocyclic radical is 1 to 4, and the heteroatom is N, O or S;

$R_4$ is —H, halogen, $C_1$-$C_4$ alkyl, $C_1$-$C_4$ alkoxy, —CF$_3$, —OCF$_3$, morpholinyl or $C_1$-$C_4$ phenylalkyl;

$R_5$ is —H, aryl or $C_3$-$C_8$ cycloalkyl; and n=0-3.

Preferably, Y is nitrogen, oxygen or sulfur; and L is

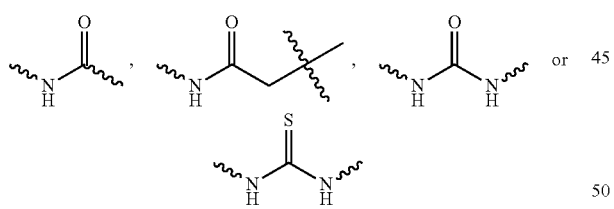

substituted at 3-position or 4-position on the benzene ring of the matrix; wherein one end of atom N is connected with the matrix;

$R_1$ is —H, $C_1$-$C_4$ alkyl,

$R_2$ is —H, halogen, $C_1$-$C_4$ alkyl, $C_1$-$C_4$ alkoxy or —NO$_2$;

$R_3$ is substituted 4-12 membered aromatic heterocyclic radical,

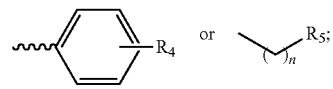

the substituent on the substituted heteroaromatic ring is —H, $C_1$-$C_6$ alkyl, aryl, —CF$_3$ or 5-10 membered aromatic heterocyclic radical; and the number of heteroatoms on the aromatic heterocyclic radical is 1 to 4, and the heteroatom is N, O or S;

$R_4$ is —H, halogen, $C_1$-$C_4$ alkyl, $C_1$-$C_4$ alkoxy, —CF$_3$, —OCF$_3$, morpholinyl or $C_1$-$C_4$ phenylalkyl;

$R_5$ is —H, aryl or $C_3$-$C_8$ cycloalkyl; and n=0-3.

Preferably, Y is nitrogen, oxygen or sulfur; and L is

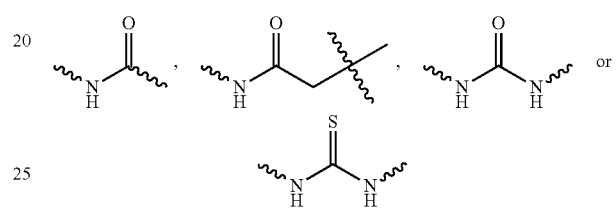

substituted at 3-position or 4-position on the benzene ring of the matrix; wherein one end of atom N is connected with the matrix;

$R_1$ is —H,

$R_2$ is —H, halogen, $C_1$-$C_4$ alkyl, $C_1$-$C_4$ alkoxy or —NO$_2$;

$R_3$ is substituted 4-12 membered aromatic heterocyclic radical,

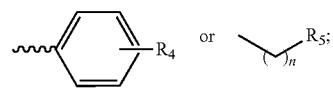

the substituent on the substituted heteroaromatic ring is —H, $C_1$-$C_6$ alkyl, aryl, —CF$_3$ or 5-10 membered aromatic heterocyclic radical; and the number of heteroatoms on the aromatic heterocyclic radical is 1 to 4, and the heteroatom is N, O or S;

$R_4$ is —H, halogen, $C_1$-$C_4$ alkyl, $C_1$-$C_4$ alkoxy, —CF$_3$, —OCF$_3$, morpholinyl or $C_1$-$C_4$ phenylalkyl;

$R_5$ is —H, aryl or $C_3$-$C_8$ cycloalkyl; and n=0-3.

Preferably, Y is nitrogen, oxygen or sulfur; and L

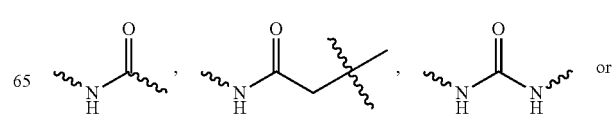

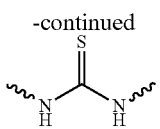

substituted at 3-position or 4-position on the benzene ring of the matrix; wherein one end of atom N is connected with the matrix;
R₁ is —H;
R₂ is —H, halogen, C₁-C₄ alkyl, C₁-C₄ alkoxy or —NO₂;
R₃ is substituted 4-12 membered aromatic heterocyclic radical,

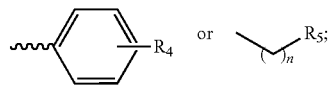

the substituent on the substituted heteroaromatic ring is —H, C₁-C₆ alkyl, aryl, —CF₃ or 5-10 membered aromatic heterocyclic radical; and the number of heteroatoms on the aromatic heterocyclic radical is 1 to 4, and the heteroatom is N, O or S;
R₄ is —H, halogen, C₁-C₄ alkyl, C₁-C₄ alkoxy, —CF₃, —OCF₃, morpholinyl or C₁-C₄ phenylalkyl;
R₅ is —H, aryl or C₃-C₈ cycloalkyl; and
n=0-3.

Further preferably, Y is nitrogen, oxygen or sulfur; and L is

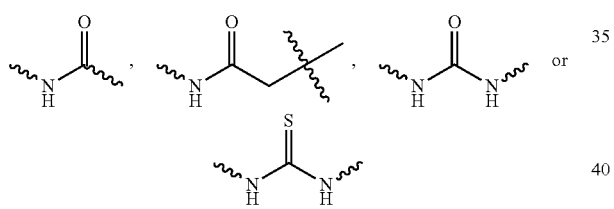

substituted at 3-position or 4-position on the benzene ring of the matrix; wherein one end of atom N is connected with the benzene ring of the matrix;
R₁ is —H, C₁-C₄ alkyl,

or substituted phenyl substituted methyl; and the substituent of the substituted phenyl is —H, halogen or C₁-C₄ alkyl;
R₂ is —H, —F, —Cl, —Br, C₁-C₄ alkyl, C₁-C₄ alkoxy or —NO₂;
R₃ is substituted 4-12 membered aromatic heterocyclic radical,

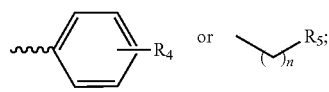

the substituent on the substituted heteroaromatic ring is —H, C₁-C₆ alkyl, aryl, —CF₃ or 5-10 membered aromatic heterocyclic radical; and the number of heteroatoms on the aromatic heterocyclic radical is 1 to 4, and the heteroatom is N, O or S;
R₄ is —H, halogen, C₁-C₄ alkyl, C₁-C₄ alkoxy, —CF₃, —OCF₃, morpholinyl or C₁-C₄ phenylalkyl;
R₅ is —H, aryl or C₃-C₈ cycloalkyl; and
n=0-4.

Preferably, Y is nitrogen, oxygen or sulfur; and L is

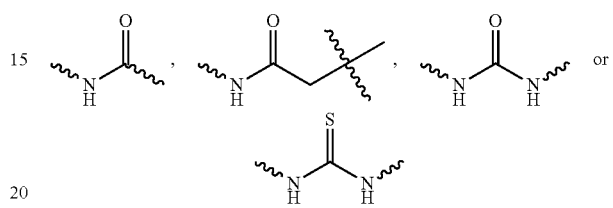

substituted at 3-position or 4-position on the benzene ring of the matrix; wherein one end of atom N is connected with the benzene ring of the matrix;
R₁ is —H, C₁-C₄ alkyl,

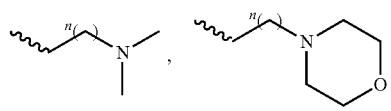

or substituted phenyl substituted methyl; and the substituent of the substituted phenyl is —H, halogen or C₁-C₄ alkyl;
R₂ is —H, —F, —Cl, C₁-C₄ alkyl, C₁-C₄ alkoxy or —NO₂;
R₃ is substituted 4-12 membered aromatic heterocyclic radical,

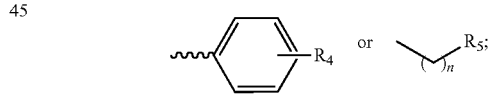

the substituent on the substituted heteroaromatic ring is —H, C₁-C₆ alkyl, aryl, —CF₃ or 5-10 membered aromatic heterocyclic radical; and the number of heteroatoms on the aromatic heterocyclic radical is 1 to 4, and the heteroatom is N, O or S;
R₄ is —H, halogen, C₁-C₄ alkyl, C₁-C₄ alkoxy, —CF₃, —OCF₃, morpholinyl or C₁-C₄ phenylalkyl;
R₅ is H, aryl or C₃-C₈ cycloalkyl; and
n=0-4.

Preferably, Y is nitrogen, oxygen or sulfur; and L is

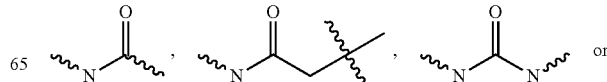

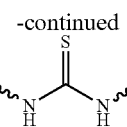

substituted at 3-position or 4-position on the benzene ring of the matrix; wherein one end of atom N is connected with the benzene ring of the matrix;
$R_1$ is —H, $C_1$-$C_4$ alkyl,

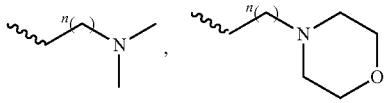

or substituted phenyl substituted methyl; and the substituent of the substituted phenyl is —H, halogen or $C_1$-$C_4$ alkyl;
$R_2$ is —H, —F, —Cl, methyl, methoxy or —NO$_2$;
$R_3$ is substituted 4-12 membered aromatic heterocyclic radical,

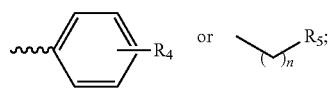

the substituent on the substituted heteroaromatic ring is —H, $C_1$-$C_6$ alkyl, aryl, —CF$_3$ or 5-10 membered aromatic heterocyclic radical; and the number of heteroatoms on the aromatic heterocyclic radical is 1 to 4, and the heteroatom is N, O or S;
$R_4$ is —H, halogen, $C_1$-$C_4$ alkyl, $C_1$-$C_4$ alkoxy, —CF$_3$, —OCF$_3$, morpholinyl or $C_1$-$C_4$ phenylalkyl;
$R_5$ is —H, aryl or $C_3$-$C_8$ cycloalkyl; and
n=0-3.

Further preferably, Y is nitrogen, oxygen or sulfur; and L is

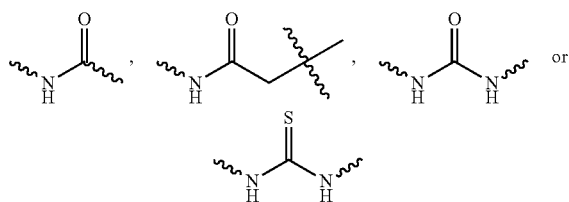

substituted at 3-position or 4-position on the benzene ring of the matrix; wherein one end of atom N is connected with the benzene ring of the matrix;
$R_1$ is —H, $C_1$-$C_4$ alkyl,

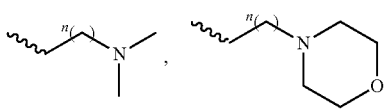

or substituted phenyl substituted methyl; and the substituent of the substituted phenyl is —H, halogen or $C_1$-$C_4$ alkyl;
$R_2$ is —H, halogen, $C_1$-$C_4$ alkyl, $C_1$-$C_4$ alkoxy or —NO$_2$;
$R_3$ is substituted 5-10 membered aromatic heterocyclic radical,

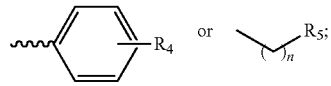

the substituent on the substituted heteroaromatic ring is —H, $C_1$-$C_4$ alkyl, aryl, —CF$_3$ or 5-10 membered aromatic heterocyclic radical; and the number of heteroatoms on the aromatic heterocyclic radical is 1 to 3, and the heteroatom is N or O;
$R_4$ is —H, halogen, $C_1$-$C_4$ alkyl, $C_1$-$C_4$ alkoxy, —CF$_3$, —OCF$_3$, morpholinyl or $C_1$-$C_4$ phenylalkyl;
$R_5$ is —H, aryl or $C_3$-$C_8$ cycloalkyl; and
n=0-4.

Preferably, Y is nitrogen, oxygen or sulfur; and L is

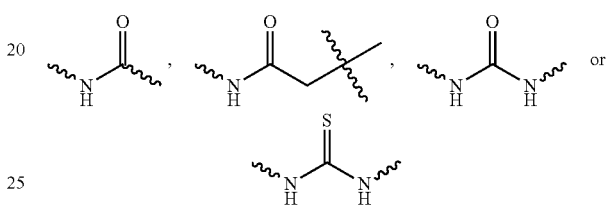

substituted at 3-position or 4-position on the benzene ring of the matrix; wherein one end of atom N is connected with the benzene ring of the matrix;
$R_1$ is —H, $C_1$-$C_4$ alkyl,

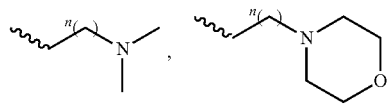

or substituted phenyl substituted methyl; and the substituent of the substituted phenyl is —H, halogen or $C_1$-$C_4$ alkyl;
$R_2$ is —H, halogen, $C_1$-$C_4$ alkyl, $C_1$-$C_4$ alkoxy or —NO$_2$;
$R_3$ is substituted 5-10 membered aromatic heterocyclic radical,

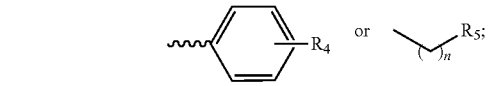

the substituent on the substituted heteroaromatic ring is —H, $C_1$-C4 alkyl, aryl, —CF$_3$ or quinolyl; and the number of heteroatoms on the aromatic heterocyclic radical is 1 to 3, and the heteroatom is N or O;
$R_4$ is —H, halogen, $C_1$-$C_4$ alkyl, $C_1$-$C_4$ alkoxy, —CF$_3$, —OCF$_3$, morpholinyl or $C_1$-$C_4$ phenylalkyl;
$R_5$ is —H, aryl or $C_3$-$C_8$ cycloalkyl; and
n=0-4.

Preferably, Y is nitrogen, oxygen or sulfur; and L is

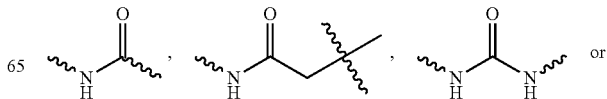

-continued

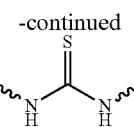

substituted at 3-position or 4-position on the benzene ring of the matrix; wherein one end of atom N is connected with the benzene ring of the matrix;
$R_1$ is —H, $C_1$-$C_4$ alkyl,

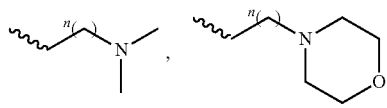

or substituted phenyl substituted methyl; and the substituent of the substituted phenyl is —H, halogen or $C_1$-$C_4$ alkyl;
$R_2$ is —H, halogen, $C_1$-$C_4$ alkyl, $C_1$-$C_4$ alkoxy or —$NO_2$;
$R_3$ is substituted 5-10 membered aromatic heterocyclic radical,

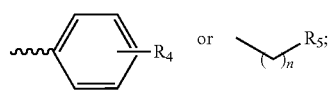

the substituent on the substituted heteroaromatic ring is —H, $C_1$-$C_4$ alkyl, phenyl, —$CF_3$ or quinolyl; and the number of heteroatoms on the aromatic heterocyclic radical is 1 to 3, and the heteroatom is N or O;
$R_4$ is —H, halogen, $C_1$-$C_4$ alkyl, $C_1$-$C_4$ alkoxy, —$CF_3$, —$OCF_3$, morpholinyl or $C_1$-$C_4$ phenylalkyl;
$R_5$ is —H, aryl or $C_3$-$C_8$ cycloalkyl; and
n=0-4.

Preferably, Y is nitrogen, oxygen or sulfur; and L is

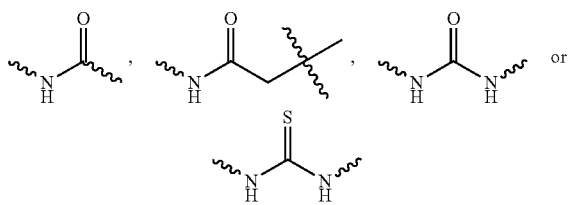

substituted at 3-position or 4-position on the benzene ring of the matrix; wherein one end of atom N is connected with the benzene ring of the matrix;
$R_1$ is —H, $C_1$-$C_4$ alkyl,

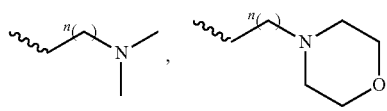

or substituted phenyl substituted methyl; and the substituent of the substituted phenyl is —H, halogen or $C_1$-$C_4$ alkyl;
$R_2$ is —H, halogen, $C_1$-$C_4$ alkyl, $C_1$-$C_4$ alkoxy or —$NO_2$;
$R_3$ is substituted 5-10 membered aromatic heterocyclic radical,

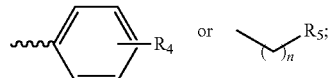

the substituent on the substituted heteroaromatic ring is —H, $C_1$-$C_4$ alkyl, phenyl, —$CF_3$ or quinolyl; and the number of heteroatoms on the aromatic heterocyclic radical is 1 to 2, and the heteroatom is N or O;
$R_4$ is —H, halogen, $C_1$-$C_4$ alkyl, $C_1$-$C_4$ alkoxy, —$CF_3$, —$OCF_3$, morpholinyl or $C_1$-$C_4$ phenylalkyl;
$R_5$ is —H, aryl or $C_3$-$C_8$ cycloalkyl; and
n=0-3.

Preferably, Y is nitrogen, oxygen or sulfur; and L is

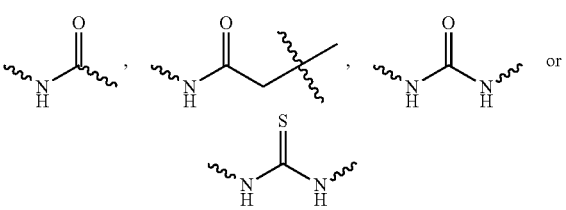

substituted at 3-position or 4-position on the benzene ring of the matrix; wherein one end of atom N is connected with the benzene ring of the matrix;
$R_1$ is —H, $C_1$-$C_4$ alkyl,

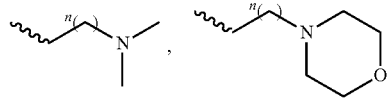

or substituted phenyl substituted methyl; and the substituent of the substituted phenyl is —H, halogen or $C_1$-$C_4$ alkyl;
$R_2$ is —H, halogen, $C_1$-$C_4$ alkyl, $C_1$-$C_4$ alkoxy or —$NO_2$;
$R_3$ is substituted pyrazolyl, substituted isoxazolyl, substituted quinolyl, substituted pyridyl,

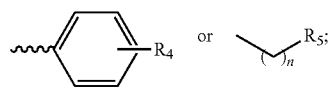

and the substituent is —H, $C_1$-$C_4$ alkyl, phenyl, —$CF_3$ or quinolyl;
$R_4$ is —H, halogen, $C_1$-$C_4$ alkyl, $C_1$-$C_4$ alkoxy, —$CF_3$, —$OCF_3$, morpholinyl or $C_1$-$C_4$ phenylalkyl;
$R_5$ is —H, aryl or $C_3$-$C_8$ cycloalkyl; and
n=0-3.

Further preferably, Y is nitrogen, oxygen or sulfur; and L is

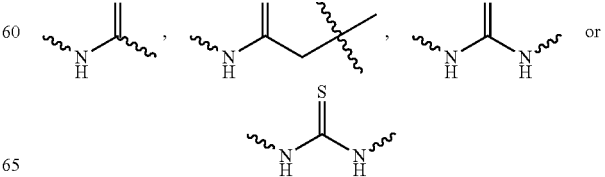

substituted at 3-position or 4-position on the benzene ring of the matrix; wherein one end of atom N is connected with the benzene ring of the matrix;

$R_1$ is —H, $C_1$-$C_4$ alkyl,

or substituted phenyl substituted methyl; and the substituent of the substituted phenyl is —H, halogen or $C_1$-$C_4$ alkyl;
$R_2$ is —H, halogen, $C_1$-$C_4$ alkyl, $C_1$-$C_4$ alkoxy or —$NO_2$;
$R_3$ is substituted 4-12 membered aromatic heterocyclic radical,

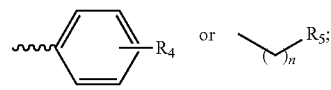

the substituent on the substituted heteroaromatic ring is —H, $C_1$-C6 alkyl, aryl, —$CF_3$ or 5-10 membered aromatic heterocyclic radical; and the number of heteroatoms on the aromatic heterocyclic radical is 1 to 4, and the heteroatom is N or O;
$R_4$ is —H, halogen, $C_1$-$C_4$ alkyl, $C_1$-$C_4$ alkoxy, —$CF_3$, —$OCF_3$ or morpholinyl;
$R_5$ is —H, aryl or $C_3$-$C_8$ cycloalkyl; and
n=0-4.

Preferably, Y is nitrogen, oxygen or sulfur; and L is

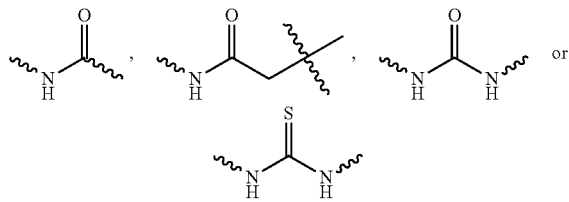

substituted at 3-position or 4-position on the benzene ring of the matrix; wherein one end of atom N is connected with the benzene ring of the matrix;
$R_1$ is —H, $C_1$-$C_4$ alkyl,

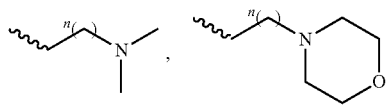

or substituted phenyl substituted methyl; and the substituent of the substituted phenyl is —H, halogen or $C_1$-$C_4$ alkyl;
$R_2$ is —H, halogen, $C_1$-$C_4$ alkyl, $C_1$-$C_4$ alkoxy or —$NO_2$;
$R_3$ is substituted 4-12 membered aromatic heterocyclic radical,

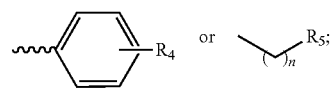

the substituent on the substituted heteroaromatic ring is —H, $C_1$-$C_6$ alkyl, aryl, —$CF_3$ or 5-10 membered aromatic heterocyclic radical; and the number of heteroatoms on the aromatic heterocyclic radical is 1 to 4, and the heteroatom is N or O;
$R_4$ is —H, —F, —Cl, —Br, $C_1$-$C_4$ alkyl, $C_1$-$C_4$ alkoxy, —$CF_3$, —$OCF_3$ or morpholinyl;
$R_5$ is —H, aryl or $C_3$-$C_8$ cycloalkyl; and
n=0-4.

Preferably, Y is nitrogen, oxygen or sulfur; and L is

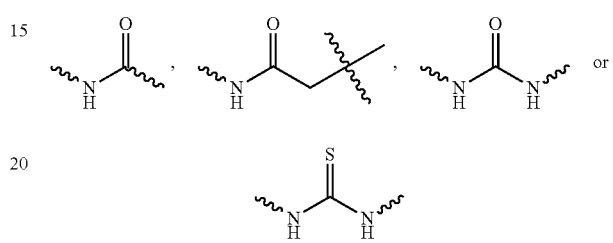

substituted at 3-position or 4-position on the benzene ring of the matrix; wherein one end of atom N is connected with the benzene ring of the matrix;
$R_1$ is —H, $C_1$-$C_4$ alkyl,

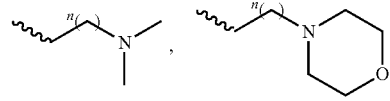

or substituted phenyl substituted methyl; and the substituent of the substituted phenyl is —H, halogen or $C_1$-$C_4$ alkyl;
$R_2$ is —H, halogen, $C_1$-$C_4$ alkyl, $C_1$-$C_4$ alkoxy or —$NO_2$;
$R_3$ is substituted 4-12 membered aromatic heterocyclic radical,

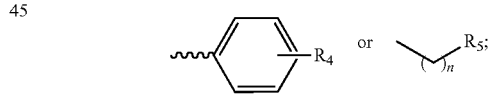

the substituent on the substituted heteroaromatic ring is —H, $C_1$-$C_6$ alkyl, aryl, —$CF_3$ or 5-10 membered aromatic heterocyclic radical; and the number of heteroatoms on the aromatic heterocyclic radical is 1 to 4, and the heteroatom is N or O;
$R_4$ is —H, —F, —Cl, —Br, $C_1$-$C_4$ alkyl, methoxy, —$CF_3$, —$OCF_3$ or morpholinyl;
$R_5$ is —H, aryl or $C_3$-$C_8$ cycloalkyl; and
n=0-4.

Preferably, Y is nitrogen, oxygen or sulfur; and L is

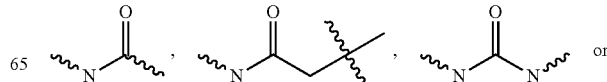

-continued

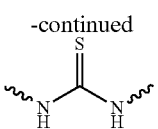

substituted at 3-position or 4-position on the benzene ring of the matrix; wherein one end of atom N is connected with the benzene ring of the matrix;
$R_1$ is —H, $C_1$-$C_4$ alkyl,

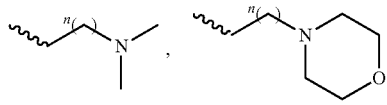

or substituted phenyl substituted methyl; and the substituent of the substituted phenyl is —H, halogen or $C_1$-$C_4$ alkyl;
$R_2$ is —H, halogen, $C_1$-$C_4$ alkyl, $C_1$-$C_4$ alkoxy or —$NO_2$;
$R_3$ is substituted 4-12 membered aromatic heterocyclic radical,

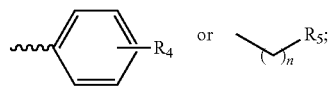

the substituent on the substituted heteroaromatic ring is —H, $C_1$-$C_6$ alkyl, aryl, —$CF_3$ or 5-10 membered aromatic heterocyclic radical; and the number of heteroatoms on the aromatic heterocyclic radical is 1 to 4, and the heteroatom is N or O;
$R_4$ is —H, —F, —Cl, —Br, methyl, isopropyl, methoxy, —$CF_3$, —$OCF_3$ or morpholinyl;
$R_5$ is —H, aryl or $C_3$-$C_8$ cycloalkyl; and
n=0-3.

Further preferably, Y is nitrogen, oxygen or sulfur; and L is

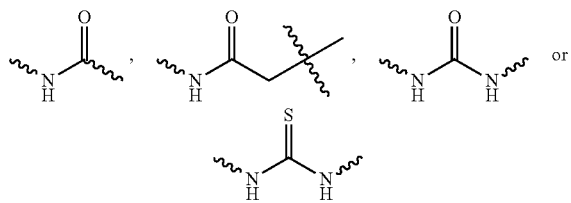

substituted at 3-position or 4-position on the benzene ring of the matrix; wherein one end of atom N is connected with the benzene ring of the matrix;
$R_1$ is —H, $C_1$-$C_4$ alkyl,

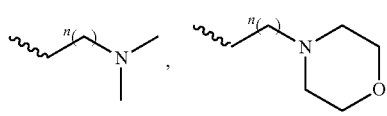

or substituted phenyl substituted methyl; and the substituent of the substituted phenyl is —H, halogen or $C_1$-$C_4$ alkyl;
$R_2$ is —H, halogen, $C_1$-$C_4$ alkyl, $C_1$-$C_4$ alkoxy or —$NO_2$;
$R_3$ is substituted 4-12 membered aromatic heterocyclic radical,

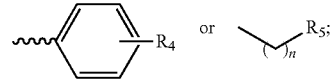

the substituent on the substituted heteroaromatic ring is —H, $C_1$-$C_6$ alkyl, aryl, —$CF_3$ or 5-10 membered aromatic heterocyclic radical; and the number of heteroatoms on the aromatic heterocyclic radical is 1 to 4, and the heteroatom is N or O;
$R_4$ is —H, halogen, $C_1$-$C_4$ alkyl, $C_1$-$C_4$ alkoxy, —$CF_3$, —$OCF_3$ or morpholinyl;
$R_5$ is —H, phenyl or $C_3$-$C_8$ cycloalkyl; and
n=0-4.

Preferably, Y is nitrogen, oxygen or sulfur; and L is

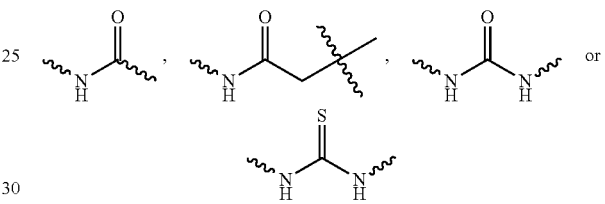

substituted at 3-position or 4-position on the benzene ring of the matrix; wherein one end of atom N is connected with the benzene ring of the matrix;
$R_1$ is —H, $C_1$-$C_4$ alkyl,

or substituted phenyl substituted methyl; and the substituent of the substituted phenyl is —H, halogen or $C_1$-$C_4$ alkyl;
$R_2$ is —H, halogen, $C_1$-$C_4$ alkyl, $C_1$-$C_4$ alkoxy or —$NO_2$;
$R_3$ is substituted 4-12 membered aromatic heterocyclic radical,

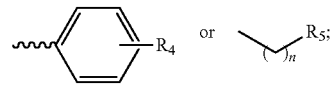

the substituent on the substituted heteroaromatic ring is —H, $C_1$-$C_6$ alkyl, aryl, —$CF_3$ or 5-10 membered aromatic heterocyclic radical; and the number of heteroatoms on the aromatic heterocyclic radical is 1 to 4, and the heteroatom is N or O;
$R_4$ is —H, halogen, $C_1$-$C_4$ alkyl, $C_1$-$C_4$ alkoxy, —$CF_3$, —$OCF_3$ or morpholinyl;
$R_5$ is —H, phenyl or cyclohexyl; and
n=0-3.

Further preferably, Y is oxygen or sulfur; and L is

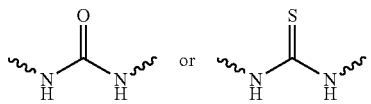

substituted at 4-position at on the benzene ring of the matrix;
$R_1$ is —H, $C_1$-$C_4$ alkyl,

or substituted 6-10 membered aromatic ring substituted methyl; and the substituent on the substituted aromatic ring is —H, halogen or $C_1$-$C_4$ alkyl;
$R_2$ is —H, halogen, $C_1$-$C_4$ alkyl, $C_1$-$C_4$ alkoxy, $C_1$-$C_4$ alkyl sulfenyl or —$NO_2$;
$R_3$ is substituted 4-12 membered aromatic heterocyclic radical,

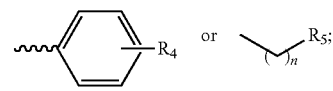

the substituent on the substituted heteroaromatic ring is —H, $C_1$-$C_6$ alkyl, aryl, —$CF_3$ or 5-10 membered aromatic heterocyclic radical; and the number of heteroatoms on the aromatic heterocyclic radical is 1 to 4, and the heteroatom is N, O or S;
$R_4$ is —H, halogen, $C_1$-$C_4$ alkyl, $C_1$-$C_4$ alkoxy, —$CF_3$, —$OCF_3$, morpholinyl or $C_1$-$C_4$ phenylalkyl;
$R_5$ is —H, aryl or $C_3$-$C_8$ cycloalkyl; and
n=0-4.

Preferably, Y is oxygen or sulfur; and L is

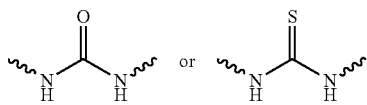

substituted at 4-position on the benzene ring of the matrix;
$R_1$ is —H or $C_1$-$C_4$ alkyl;
$R_2$ is —H, halogen, $C_1$-$C_4$ alkyl, $C_1$-$C_4$ alkoxy, $C_1$-$C_4$ alkyl sulfenyl or —$NO_2$;
$R_3$ is substituted 4-12 membered aromatic heterocyclic radical,

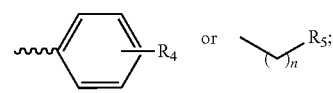

the substituent on the substituted heteroaromatic ring is —H, $C_1$-$C_6$ alkyl, aryl, —$CF_3$ or 5-10 membered aromatic heterocyclic radical; and the number of heteroatoms on the aromatic heterocyclic radical is 1 to 4, and the heteroatom is N, O or S;
$R_4$ is —H, halogen, $C_1$-$C_4$ alkyl, $C_1$-$C_4$ alkoxy, —$CF_3$, —$OCF_3$, morpholinyl or $C_1$-$C_4$ phenylalkyl;
$R_5$ is —H, aryl or $C_3$-$C_8$ cycloalkyl; and
n=0-4.

Preferably, Y is oxygen or sulfur; and L is

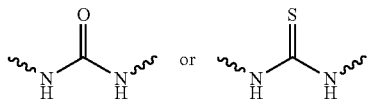

substituted at 4-position on the benzene ring of the matrix;
$R_1$ is —H;
$R_2$ is —H, halogen, $C_1$-$C_4$ alkyl, $C_1$-$C_4$ alkoxy, $C_1$-$C_4$ alkyl sulfenyl or —$NO_2$;
$R_3$ is substituted 4-12 membered aromatic heterocyclic radical,

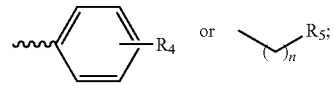

the substituent on the substituted heteroaromatic ring is —H, $C_1$-$C_6$ alkyl, aryl, —$CF_3$ or 5-10 membered aromatic heterocyclic radical; and the number of heteroatoms on the aromatic heterocyclic radical is 1 to 4, and the heteroatom is N, O or S;
$R_4$ is —H, halogen, $C_1$-$C_4$ alkyl, $C_1$-$C_4$ alkoxy, —$CF_3$, —$OCF_3$, morpholinyl or $C_1$-$C_4$ phenylalkyl;
$R_5$ is —H, aryl or $C_3$-$C_8$ cycloalkyl; and
n=0-4.

Most preferably, Y is oxygen or sulfur; and L is

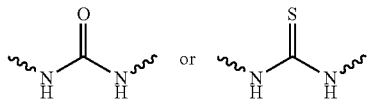

substituted at 4-position on the benzene ring of the matrix;
$R_1$ is —H;
$R_2$ is —H, —F, —Cl, methyl, methoxy or —$NO_2$;
$R_3$ is substituted pyrazolyl, substituted isoxazolyl, substituted quinolyl, substituted pyridyl,

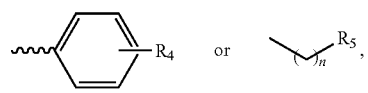

and the substituent is —H, $C_1$-$C_4$ alkyl, phenyl, —$CF_3$ or quinolyl;
$R_4$ is —H, —F, —Cl, —Br, methyl, isopropyl, methoxy, —$CF_3$, —$OCF_3$ or morpholinyl;
$R_5$ is —H, phenyl or cyclohexyl; and
n=0-3.

Further, when L is

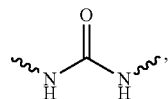

the pyrazolopyrimidine derivative has a structural formula II as follows:

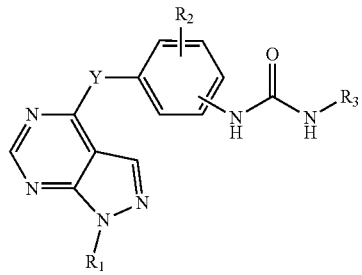

wherein, Y is nitrogen, oxygen or sulfur;
R$_1$ is —H, C$_1$-C$_4$ alkyl,

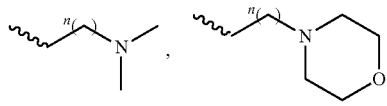

or substituted phenyl substituted methyl; and the substituent of the substituted phenyl is —H, halogen or C$_1$-C$_4$ alkyl;
R$_2$ is —H, halogen, C$_1$-C$_4$ alkyl, C$_1$-C$_4$ alkoxy or —NO$_2$;
R$_3$ is substituted 4-12 membered aromatic heterocyclic radical,

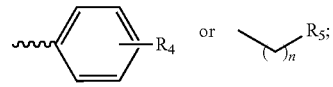

the substituent on the substituted heteroaromatic ring is —H, C$_1$-C$_6$ alkyl, aryl, —CF$_3$ or 5-10 membered aromatic heterocyclic radical; and the number of heteroatoms on the aromatic heterocyclic radical is 1 to 4, and the heteroatom is N, O or S;
R$_4$ is —H, halogen, C$_1$-C$_4$ alkyl, C$_1$-C$_4$ alkoxy, —CF$_3$, —OCF$_3$ or morpholinyl;
R$_5$ is —H, aryl or C$_3$-C$_8$ cycloalkyl; and
n=0-4.
Preferably, Y is nitrogen, oxygen or sulfur, and R$_1$ is —H, C$_1$-C$_4$ alkyl,

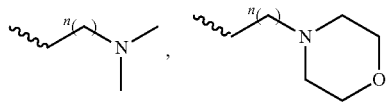

or substituted phenyl substituted methyl; and the substituent of the substituted phenyl is —H, —F, —Cl or —Br;
R$_2$ is —H, halogen, C$_1$-C$_4$ alkyl, C$_1$-C$_4$ alkoxy or —NO$_2$;
R$_3$ is substituted 4-12 membered aromatic heterocyclic radical,

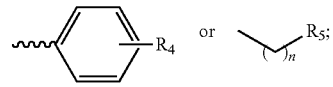

the substituent on the substituted heteroaromatic ring is —H, C$_1$-C$_6$ alkyl, aryl, —CF$_3$ or 5-10 membered aromatic heterocyclic radical; and the number of heteroatoms on the aromatic heterocyclic radical is 1 to 4, and the heteroatom is N, O or S;
R$_4$ is —H, halogen, C$_1$-C$_4$ alkyl, C$_1$-C$_4$ alkoxy, —CF$_3$, —OCF$_3$ or morpholinyl;
R$_5$ is H, aryl or C$_3$-C$_8$ cycloalkyl; and
n=0-3.
Preferably, Y is nitrogen, oxygen or sulfur, and R$_1$ is —H, C$_1$-C$_4$ alkyl,

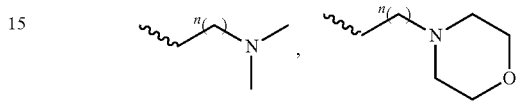

or substituted phenyl substituted methyl; and the substituent of the substituted phenyl is —H or —Br;
R$_2$ is —H, halogen, C$_1$-C$_4$ alkyl, C$_1$-C$_4$ alkoxy or —NO$_2$;
R$_3$ is substituted 4-12 membered aromatic heterocyclic radical,

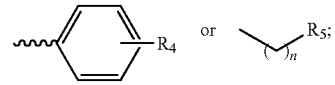

the substituent on the substituted heteroaromatic ring is —H, C$_1$-C$_6$ alkyl, aryl, —CF$_3$ or 5-10 membered aromatic heterocyclic radical; and the number of heteroatoms on the aromatic heterocyclic radical is 1 to 4, and the heteroatom is N, O or S;
R$_4$ is —H, halogen, C$_1$-C$_4$ alkyl, C$_1$-C$_4$ alkoxy, —CF$_3$, —OCF$_3$ or morpholinyl;
R$_5$ is H, aryl or C$_3$-C$_8$ cycloalkyl; and
n=0-3.
Preferably, Y is nitrogen, oxygen or sulfur, and R$_1$ is —H, C$_1$-C$_4$ alkyl,

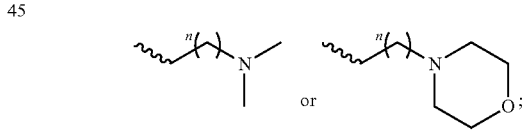

R$_2$ is —H, halogen, C$_1$-C$_4$ alkyl, C$_1$-C$_4$ alkoxy or —NO$_2$;
R$_3$ is substituted 4-12 membered aromatic heterocyclic radical,

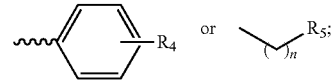

the substituent on the substituted heteroaromatic ring is —H, C$_1$-C$_6$ alkyl, aryl, —CF$_3$ or 5-10 membered aromatic heterocyclic radical; and the number of heteroatoms on the aromatic heterocyclic radical is 1 to 4, and the heteroatom is N, O or S;

$R_4$ is —H, halogen, $C_1$-$C_4$ alkyl, $C_1$-$C_4$ alkoxy, —$CF_3$, —$OCF_3$, morpholinyl or $C_1$-$C_4$ phenylalkyl;
$R_5$ is —H, aryl or $C_3$-$C_8$ cycloalkyl; and
n=0-3.

Preferably, Y is nitrogen, oxygen or sulfur, and $R_1$ is —H, I or;

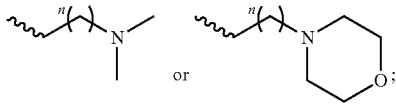

$R_2$ is —H, halogen, $C_1$-$C_4$ alkyl, $C_1$-$C_4$ alkoxy or —$NO_2$;
$R_3$ is substituted 4-12 membered aromatic heterocyclic radical,

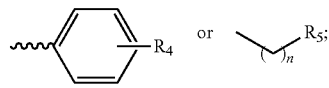

the substituent on the substituted heteroaromatic ring is —H, $C_1$-$C_6$ alkyl, aryl, —$CF_3$ or 5-10 membered aromatic heterocyclic radical; and the number of heteroatoms on the aromatic heterocyclic radical is 1 to 4, and the heteroatom is N, O or S;
$R_4$ is —H, halogen, $C_1$-$C_4$ alkyl, $C_1$-$C_4$ alkoxy, —$CF_3$, —$OCF_3$, morpholinyl or $C_1$-$C_4$ phenylalkyl;
$R_5$ is —H, aryl or $C_3$-$C_8$ cycloalkyl; and
n=0-3.

Preferably, Y is nitrogen, oxygen or sulfur, and $R_1$ is —H;
$R_2$ is —H, halogen, $C_1$-$C_4$ alkyl, $C_1$-$C_4$ alkoxy or —$NO_2$;
$R_3$ is substituted 4-12 membered aromatic heterocyclic radical,

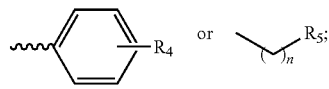

the substituent on the substituted heteroaromatic ring is —H, $C_1$-$C_6$ alkyl, aryl, —$CF_3$ or 5-10 membered aromatic heterocyclic radical; and the number of heteroatoms on the aromatic heterocyclic radical is 1 to 4, and the heteroatom is N, O or S;
$R_4$ is —H, halogen, $C_1$-$C_4$ alkyl, $C_1$-$C_4$ alkoxy, —$CF_3$, —$OCF_3$, morpholinyl or $C_1$-$C_4$ phenylalkyl;
$R_5$ is —H, aryl or $C_3$-$C_8$ cycloalkyl; and
n=0-3.

Further preferably, Y is nitrogen, oxygen or sulfur, and $R_1$ is —H, $C_1$-$C_4$ alkyl,

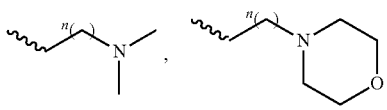

or substituted phenyl substituted methyl; and the substituent of the substituted phenyl is —H, halogen or $C_1$-$C_4$ alkyl;
$R_2$ is —H, —F, —Cl, —Br, $C_1$-$C_4$ alkyl, $C_1$-$C_4$ alkoxy or —$NO_2$;
$R_3$ is substituted 4-12 membered aromatic heterocyclic radical,

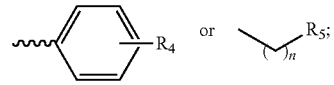

the substituent on the substituted heteroaromatic ring is —H, $C_1$-$C_6$ alkyl, aryl, —$CF_3$ or 5-10 membered aromatic heterocyclic radical; and the number of heteroatoms on the aromatic heterocyclic radical is 1 to 4, and the heteroatom is N, O or S;
$R_4$ is —H, halogen, $C_1$-$C_4$ alkyl, $C_1$-$C_4$ alkoxy, —$CF_3$, —$OCF_3$ or morpholinyl;
$R_5$ is —H, aryl or $C_3$-$C_8$ cycloalkyl; and
n=0-4.

Preferably, Y is nitrogen, oxygen or sulfur, and $R_1$ is —H, $C_1$-$C_4$ alkyl,

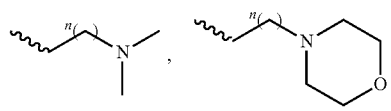

or substituted phenyl substituted methyl; and the substituent of the substituted phenyl is —H, halogen or $C_1$-$C_4$ alkyl;
$R_2$ is —H, —F, —Cl, methyl, methoxy or —$NO_2$;
$R_3$ is substituted 4-12 membered aromatic heterocyclic radical,

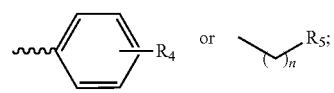

the substituent on the substituted heteroaromatic ring is —H, $C_1$-$C_6$ alkyl, aryl, —$CF_3$ or 5-10 membered aromatic heterocyclic radical; and the number of heteroatoms on the aromatic heterocyclic radical is 1 to 4, and the heteroatom is N, O or S;
$R_4$ is —H, halogen, $C_1$-$C_4$ alkyl, $C_1$-$C_4$ alkoxy, —$CF_3$, —$OCF_3$ or morpholinyl;
$R_5$ is —H, aryl or $C_3$-$C_8$ cycloalkyl; and
n=0-3.

Further preferably, Y is nitrogen, oxygen or sulfur, and $R_1$ is —H, $C_1$-$C_4$ alkyl,

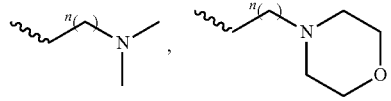

or substituted phenyl substituted methyl; and the substituent of the substituted phenyl is —H, halogen or $C_1$-$C_4$ alkyl;
$R_2$ is —H, halogen, $C_1$-$C_4$ alkyl, $C_1$-$C_4$ alkoxy or —$NO_2$;
$R_3$ is substituted 5-10 membered aromatic heterocyclic radical,

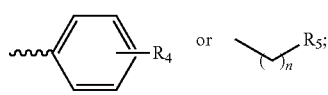

the substituent on the substituted heteroaromatic ring is —H, $C_1$-C4 alkyl, aryl, —$CF_3$ or quinolyl; and the number of heteroatoms on the aromatic heterocyclic radical is 1 to 3, and the heteroatom is N or O;

$R_4$ is —H, halogen, $C_1$-$C_4$ alkyl, $C_1$-$C_4$ alkoxy, —$CF_3$, —$OCF_3$ or morpholinyl;

$R_5$ is —H, aryl or $C_3$-$C_8$ cycloalkyl; and n=0-4.

Preferably, Y is nitrogen, oxygen or sulfur, and $R_1$ is —H, $C_1$-$C_4$ alkyl,

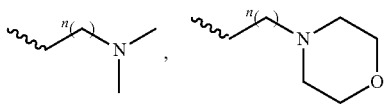

or substituted phenyl substituted methyl; and the substituent of the substituted phenyl is —H, halogen or $C_1$-$C_4$ alkyl;

$R_2$ is —H, halogen, $C_1$-$C_4$ alkyl, $C_1$-$C_4$ alkoxy or —$NO_2$;

$R_3$ is substituted pyrazolyl, substituted isoxazolyl, substituted quinolyl, substituted pyridyl,

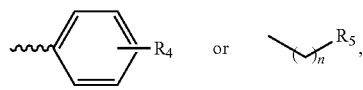

and the substituent is —H, $C_1$-$C_4$ alkyl, phenyl, —$CF_3$ or quinolyl;

$R_4$ is —H, halogen, $C_1$-$C_4$ alkyl, $C_1$-$C_4$ alkoxy, —$CF_3$, —$OCF_3$ or morpholinyl;

$R_5$ is —H, aryl or $C_3$-$C_8$ cycloalkyl; and n=0-3.

Further preferably, Y is nitrogen, oxygen or sulfur, and $R_1$ is —H, $C_1$-$C_4$ alkyl,

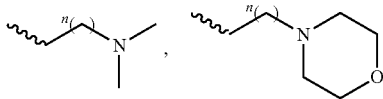

or substituted phenyl substituted methyl; and the substituent of the substituted phenyl is —H, halogen or $C_1$-$C_4$ alkyl;

$R_2$ is —H, halogen, $C_1$-$C_4$ alkyl, $C_1$-$C_4$ alkoxy or —$NO_2$;

$R_3$ is substituted 4-12 membered aromatic heterocyclic radical,

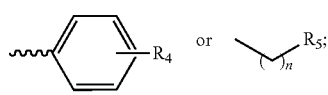

the substituent on the substituted heteroaromatic ring is —H, $C_1$-$C_6$ alkyl, aryl, —$CF_3$ or 5-10 membered aromatic heterocyclic radical; and the number of heteroatoms on the aromatic heterocyclic radical is 1 to 4, and the heteroatom is N or O;

$R_4$ is —H, —F, —Cl, —Br, $C_1$-$C_4$ alkyl, $C_1$-$C_4$ alkoxy, —$CF_3$, —$OCF_3$ or morpholinyl;

$R_5$ is —H, aryl or $C_3$-$C_8$ cycloalkyl; and n=0-4.

Preferably, Y is nitrogen, oxygen or sulfur, and $R_1$ is —H, $C_1$-$C_4$ alkyl,

or substituted phenyl substituted methyl; and the substituent of the substituted phenyl is —H, halogen or $C_1$-$C_4$ alkyl;

$R_2$ is —H, halogen, $C_1$-$C_4$ alkyl, $C_1$-$C_4$ alkoxy or —$NO_2$;

$R_3$ is substituted 4-12 membered aromatic heterocyclic radical,

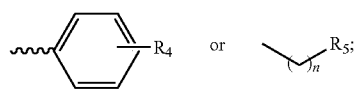

the substituent on the substituted heteroaromatic ring is —H, $C_1$-$C_6$ alkyl, aryl, —$CF_3$ or 5-10 membered aromatic heterocyclic radical; and the number of heteroatoms on the aromatic heterocyclic radical is 1 to 4, and the heteroatom is N or O;

$R_4$ is —H, —F, —Cl, —Br, methyl, isopropyl, methoxy, —$CF_3$, —$OCF_3$ or morpholinyl;

$R_5$ is —H, aryl or $C_3$-$C_8$ cycloalkyl; and n=0-3.

Further preferably, Y is nitrogen, oxygen or sulfur, and $R_1$ is —H, $C_1$-$C_4$ alkyl,

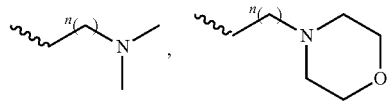

or substituted phenyl substituted methyl; and the substituent of the substituted phenyl is —H, halogen or $C_1$-$C_4$ alkyl;

$R_2$ is —H, halogen, $C_1$-$C_4$ alkyl, $C_1$-$C_4$ alkoxy or —$NO_2$;

$R_3$ is substituted 4-12 membered aromatic heterocyclic radical,

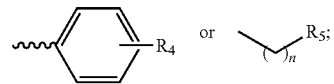

the substituent on the substituted heteroaromatic ring is —H, $C_1$-$C_6$ alkyl, aryl, —$CF_3$ or 5-10 membered aromatic heterocyclic radical; and the number of heteroatoms on the aromatic heterocyclic radical is 1 to 4, and the heteroatom is N or O;

$R_4$ is —H, halogen, $C_1$-$C_4$ alkyl, $C_1$-$C_4$ alkoxy, —$CF_3$, —$OCF_3$ or morpholinyl;

$R_5$ is —H, phenyl or $C_3$-$C_8$ cycloalkyl; and n=0-4.

Preferably, Y is nitrogen, oxygen or sulfur, and $R_1$ is —H, $C_1$-$C_4$ alkyl,

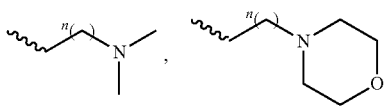

or substituted phenyl substituted methyl; and the substituent of the substituted phenyl is —H, halogen or $C_1$-$C_4$ alkyl;
$R_2$ is —H, halogen, $C_1$-$C_4$ alkyl, $C_1$-$C_4$ alkoxy or —$NO_2$;
$R_3$ is substituted 4-12 membered aromatic heterocyclic radical,

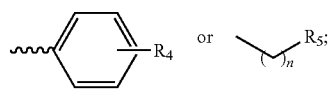

the substituent on the substituted heteroaromatic ring is —H, $C_1$-$C_6$ alkyl, aryl, —$CF_3$ or 5-10 membered aromatic heterocyclic radical; and the number of heteroatoms on the aromatic heterocyclic radical is 1 to 4, and the heteroatom is N or O;
$R_4$ is —H, halogen, $C_1$-$C_4$ alkyl, $C_1$-$C_4$ alkoxy, —$CF_3$, —$OCF_3$ or morpholinyl;
$R_5$ is —H, phenyl or cyclohexyl; and
n=0-3.

Further preferably, Y is oxygen or sulfur, and $R_1$ is —H, $C_1$-$C_4$ alkyl,

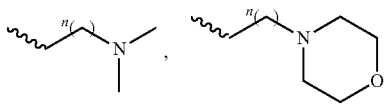

or substituted 6-10 membered aromatic ring substituted methyl; and the substituent on the substituted aromatic ring is —H, halogen or $C_1$-$C_4$ alkyl;
$R_2$ is —H, halogen, $C_1$-$C_4$ alkyl, $C_1$-$C_4$ alkoxy, $C_1$-$C_4$ alkyl sulfenyl or —$NO_2$;
$R_3$ is substituted 4-12 membered aromatic heterocyclic radical,

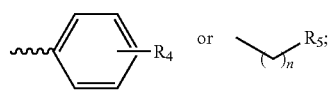

the substituent on the substituted heteroaromatic ring is —H, $C_1$-$C_6$ alkyl, aryl, —$CF_3$ or 5-10 membered aromatic heterocyclic radical; and the number of heteroatoms on the aromatic heterocyclic radical is 1 to 4, and the heteroatom is N, O or S;
$R_4$ is —H, halogen, $C_1$-$C_4$ alkyl, $C_1$-$C_4$ alkoxy, —$CF_3$, —$OCF_3$, morpholinyl or $C_1$-$C_4$ phenylalkyl;
$R_5$ is —H, aryl or $C_3$-$C_8$ cycloalkyl; and
n=0-4.

Preferably, Y is oxygen or sulfur, and $R_1$ is —H or $C_1$-$C_4$ alkyl;
$R_2$ is —H, halogen, $C_1$-$C_4$ alkyl, $C_1$-$C_4$ alkoxy, $C_1$-$C_4$ alkyl sulfenyl or —$NO_2$;
$R_3$ is substituted 4-12 membered aromatic heterocyclic radical,

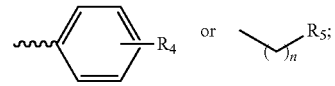

the substituent on the substituted heteroaromatic ring is —H, $C_1$-$C_6$ alkyl, aryl, —$CF_3$ or 5-10 membered aromatic heterocyclic radical; and the number of heteroatoms on the aromatic heterocyclic radical is 1 to 4, and the heteroatom is N, O or S;
$R_4$ is —H, halogen, $C_1$-$C_4$ alkyl, $C_1$-$C_4$ alkoxy, —$CF_3$, —$OCF_3$, morpholinyl or $C_1$-$C_4$ phenylalkyl;
$R_5$ is —H, aryl or $C_3$-$C_8$ cycloalkyl; and
n=0-4.

Preferably, Y is oxygen or sulfur, and $R_1$ is —H;
$R_2$ is —H, halogen, $C_1$-$C_4$ alkyl, $C_1$-$C_4$ alkoxy, $C_1$-$C_4$ alkyl sulfenyl or —$NO_2$;
$R_3$ is substituted 4-12 membered aromatic heterocyclic radical,

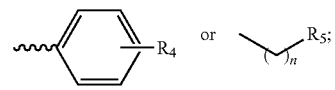

the substituent on the substituted heteroaromatic ring is —H, $C_1$-$C_6$ alkyl, aryl, —$CF_3$ or 5-10 membered aromatic heterocyclic radical; and the number of heteroatoms on the aromatic heterocyclic radical is 1 to 4, and the heteroatom is N, O or S;
$R_4$ is —H, halogen, $C_1$-$C_4$ alkyl, $C_1$-$C_4$ alkoxy, —$CF_3$, —$OCF_3$, morpholinyl or $C_1$-$C_4$ phenylalkyl;
$R_5$ is —H, aryl or $C_3$-$C_8$ cycloalkyl; and
n=0-4.

Most preferably, Y is oxygen or sulfur, and $R_1$ is —H;
$R_2$ is —H, —F, —Cl, methyl, methoxy or —$NO_2$;
$R_3$ is substituted pyrazolyl, substituted isoxazolyl, substituted quinolyl, substituted pyridyl,

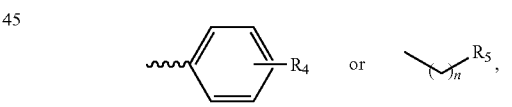

and the substituent is —H, $C_1$-$C_4$ alkyl, phenyl, —$CF_3$ or quinolyl;
$R_4$ is —H, —F, —Cl, —Br, methyl, isopropyl, methoxy, —$CF_3$, —$OCF_3$ or morpholinyl;
$R_5$ is —H, phenyl or cyclohexyl; and
n=0-3.

Further, when L is

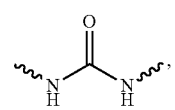

the pyrazolopyrimidine derivative has a structural formula III as follows:

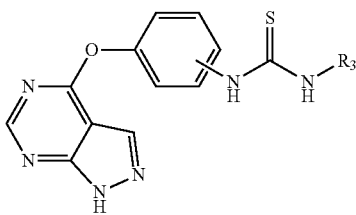

wherein, $R_3$ is substituted 4-12 membered aromatic heterocyclic radical,

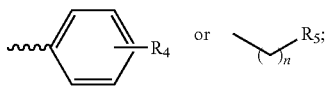

the substituent on the substituted heteroaromatic ring is —H, $C_1$-$C_6$ alkyl, aryl, —$CF_3$ or 5-10 membered aromatic heterocyclic radical; and the number of heteroatoms on the aromatic heterocyclic radical is 1 to 4, and the heteroatom is N, O or S;
$R_4$ is —H, halogen, $C_1$-$C_4$ alkyl, $C_1$-$C_4$ alkoxy, —$CF_3$, —$OCF_3$ or morpholinyl;
$R_5$ is —H, aryl or $C_3$-$C_8$ cycloalkyl; and
n=0-4.

Preferably, $R_3$ is substituted 5-10 membered aromatic heterocyclic radical or

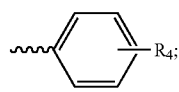

the substituent on the substituted heteroaromatic ring is —H, $C_1$-$C_6$ alkyl, aryl, —$CF_3$ or 5-10 membered aromatic heterocyclic radical; and the number of heteroatoms on the aromatic heterocyclic radical is 1 to 4, and the heteroatom is N or O; and
$R_4$ is —H, halogen, $C_1$-$C_4$ alkyl, $C_1$-$C_4$ alkoxy, —$CF_3$, —$OCF_3$ or morpholinyl.

Preferably, $R_3$ is

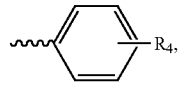

substituted pyrazolyl, substituted isoxazolyl, substituted quinolyl or substituted pyridyl, and the substituent is —H, $C_1$-$C_4$ alkyl, phenyl, —$CF_3$ or quinolyl; and
$R_4$ is —H, halogen, $C_1$-$C_4$ alkyl, $C_1$-$C_4$ alkoxy, —$CF_3$, —$OCF_3$ or morpholinyl.

Preferably, $R_3$ is

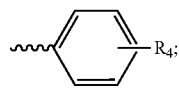

and
$R_4$ is —H, halogen, $C_1$-$C_4$ alkyl, $C_1$-$C_4$ alkoxy, —$CF_3$, —$OCF_3$ or morpholinyl.

Preferably, $R_3$ is

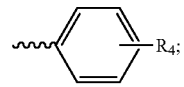

and
$R_4$ is —H, —F, —Cl, —Br, $C_1$-$C_4$ alkyl, $C_1$-$C_4$ alkoxy or —$CF_3$.

Preferably, $R_3$ is

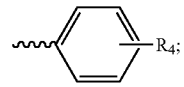

and
$R_4$ is —H, $C_1$-$C_4$ alkyl or —$CF_3$.

Most preferably, $R_3$ is

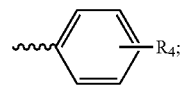

and
$R_4$ is —H or —$CF_3$.

Further, when L is

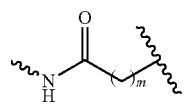

and one end of atom N is connected with the matrix, the pyrazolopyrimidine derivative of the invention has a structural formula IV as follows:

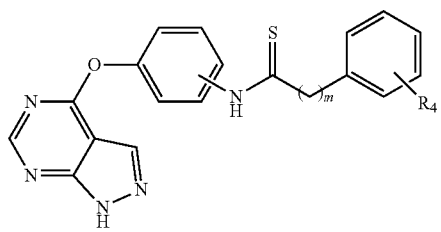

wherein, $R_4$ is —H, halogen, $C_1$-$C_4$ alkyl, $C_1$-$C_4$ alkoxy or —$CF_3$; and m=0-2.

Preferably, $R_4$ is halogen or —$CF_3$; and m=0 or 1.

Most preferably, $R_4$ is —F, —Cl, —Br or —$CF_3$; and m=0 or 1.

Further, the specific name of the pyrazolopyrimidine derivative is as follows:
1-(4-((1H-pyrazolopyrimidine-4-yl)oxy)phenyl)-3-(4-(trifluoromethyl)phenyl)urea,
1-(4-((1H-pyrazolopyrimidine-4-yl)oxy)phenyl)-3-(4-chloro-3-(trifluoromethyl)phenyl)urea,
1-(4-((1H-pyrazolopyrimidine-4-yl)oxy)phenyl)-3-(4-bromophenyl)urea, 1-(4-((1H-pyrazolopyrimidine-4-yl)oxy)phenyl)-3-(2,3-dimethylphenyl)urea,
1-(4-((1H-pyrazolopyrimidine-4-yl)oxy)phenyl)-3-(3-methoxyphenyl)urea,
1-(4-((1H-pyrazolopyrimidine-4-yl)oxy)phenyl)-3-(3-(trifluoromethyl)phenyl)urea,
1-(4-((1H-pyrazolopyrimidine-4-yl)oxy)-3-fluorophenyl)-3-(3-isopropylphenyl)urea,
1-(4-((1H-pyrazolopyrimidine-4-yl)oxy)-3-fluorophenyl)-3-(3-(trifluoromethoxy)phenyl)urea,
1-(4-((1H-pyrazolopyrimidine-4-yl)oxy)-3-fluorophenyl)-3-(4-(trifluoromethyl)phenyl)urea,
1-(4-((1H-pyrazolopyrimidine-4-yl)oxy)-3-fluorophenyl)-3-(4-chloro-3-(trifluoromethyl) phenyl)urea,
1-(4-((1H-pyrazolopyrimidine-4-yl)oxy)-2-methylphenyl)-3-(3-(trifluoromethyl)phenyl)urea,
1-(4-((1H-pyrazolopyrimidine-4-yl)oxy)phenyl)-3-(3,5-bis(trifluoromethyl)phenyl)urea,
1-(4-((1H-pyrazolopyrimidine-4-yl)oxy)phenyl)-3-(2-chloro-4-(trifluoromethyl)phenyl)urea,
1-(4-((1H-pyrazolopyrimidine-4-yl)oxy)phenyl)-3-(3-fluorophenyl)urea,
1-(4-((1H-pyrazolopyrimidine-4-yl)oxy)phenyl)-3-phenylurea,
1-(4-((1H-pyrazolopyrimidine-4-yl)oxy)phenyl)-3-(4-morpholinphenyl)urea,
1-(4-((1H-pyrazolopyrimidine-4-yl)oxy)phenyl)-3-(4-fluorophenyl)urea,
(S)-1-(4-((1H-pyrazolopyrimidine-4-yl)oxy)phenyl)-3-(1-phenethyl)urea,
(R)-1-(4-((1H-pyrazolopyrimidine-4-yl)oxy)phenyl)-3-(1-phenethyl)urea,
1-(4-((1H-pyrazolopyrimidine-4-yl)oxy)phenyl)-3-(methylcyclohexyl)urea,
1-(4-((1H-pyrazolopyrimidine-4-yl)oxy)phenyl)-3-cyclohexylurea,
1-(4-((1H-pyrazolopyrimidine-4-yl)oxy)phenyl)-3-(6-quinolyl)urea,
1-(4-((1H-pyrazolopyrimidine-4-yl)oxy)phenyl)-3-pyridylurea,
1-(4-((1H-pyrazolopyrimidine-4-yl)oxy)phenyl)-3-(3-tert-butyl-1-phenyl-1H-pyrazol-5-yl)urea,
1-(4-((1H-pyrazolopyrimidine-4-yl)oxy)phenyl)-3-(3-tert-butylisoxazol-5-yl)urea,
1-(4-((1H-pyrazolopyrimidine-4-yl)oxy)phenyl)-3-(5-tert-butylisoxazol-3-yl)urea,
1-(4-((1H-pyrazolopyrimidine-4-yl)oxy)phenyl)-3-(3-isopropyl-1-methyl-pyrazol-5-yl)urea,
1-(4-((1H-pyrazolopyrimidine-4-yl)oxy)phenyl)-3-(5-(trifluoromethyl)isoxazol-3-yl)urea,
1-(4-((1H-pyrazolopyrimidine-4-yl)oxy)-2-methylphenyl)-3-(5-tert-butylisoxazol-3-yl)urea,
1-(4-((1H-pyrazolopyrimidine-4-yl)oxy)-2-fluorophenyl)-3-(5-tert-butylisoxazol-3-yl)urea,
1-(4-((1H-pyrazolopyrimidine-4-yl)oxy)-3-fluorophenyl)-3-(5-tert-butylisoxazol-3-yl)urea,
1-(4-((1H-pyrazolopyrimidine-4-yl)oxy)-3-chlorophenyl)-3-(3-tert-butyl-1-methylpyrazol-5-yl)urea,
1-(4-((1H-pyrazolopyrimidine-4-yl)oxy)-3,5-difluorophenyl)-3-(5-tert-butylisoxazol-3-yl)urea,
1-(4-((1H-pyrazolopyrimidine-4-yl)oxy)phenyl)-3-(3-tert-butyl-1-methyl-1H-pyrazol-5-yl)urea,
1-(4-((1H-pyrazolopyrimidine-4-yl)oxy)phenyl)-3-(1-methyl-3-(trifluoromethyl)1H-pyrazol-5-yl)urea,
1-(4-((1H-pyrazolopyrimidine-4-yl)oxy)-3-fluorophenyl)-3-(1-methyl-3 (trifluoromethyl)1H-pyrazol-5-yl)urea,
1-(4-((1H-pyrazolopyrimidine-4-yl)oxy)-2-nitrophenyl)-3-(5-tert-butylisoxazol-3-yl)urea,
1-(4-((1H-pyrazolopyrimidine-4-yl)oxy)-3-fluorophenyl)-3-(3-tert-butylisoxazol-5-yl)urea,
1-(4-((1H-pyrazolopyrimidine-4-yl)oxy)-2-methoxyphenyl)-3-(5-tert-butylisoxazol-3-yl)urea,
1-(4-((1H-pyrazolopyrimidine-4-yl)oxy)phenyl)-3-(3-tert-butyl-1-(quinolin-7-yl)-1H-pyrazol-5-yl)urea,
1-(3-((1H-pyrazolopyrimidine-4-yl)oxy)phenyl)-3-(3-(trifluoromethyl)phenyl)urea,
1-(3-((1H-pyrazolopyrimidine-4-yl)oxy)phenyl)-3-(4-chloro-3-(trifluoromethyl)phenyl)urea,
1-(3-((1H-pyrazolopyrimidine-4-yl)oxy)phenyl)-3-(4-(trifluoromethyl)phenyl)urea,
1-(3-((1H-pyrazolopyrimidine-4-yl)oxy)phenyl)-3-(5-tert-butylisoxazol-3-yl)urea,
1-(4-((1H-pyrazolopyrimidine-4-yl)oxy)phenyl)-3-phenylthiourea,
1-(4-((1H-pyrazolopyrimidine-4-yl)oxy)phenyl)-3-(3-trifluoromethylphenyl)thiourea,
1-(4-(1H-pyrazolopyrimidine-4-sulfydryl)phenyl)-3-(4-trifluoromethyl)phenyl)urea,
1-(4-(1H-pyrazolopyrimidine-4-sulfydryl)phenyl)-3-(3-(trifluoromethyl)phenyl)urea,
1-(4-(1H-pyrazolopyrimidine-4-sulfydryl)phenyl)-3-(5-tert-butylisoxazol-3-yl)urea,
1-(4-((1H-pyrazolopyrimidine-4-yl)oxy)-3-fluorophenyl)-3-(3-tert-butyl-1-methylpyrazol-5-yl)urea,
1-(4-((1H-pyrazolopyrimidine-4-yl)oxy)-3-chlorophenyl)-3-(5-tert-butylisoxazol-3-yl)urea,
1-(4-((1H-pyrazolopyrimidine-4-yl)oxy)-2-fluorophenyl)-3-(4-chloro-3-(trifluoromethyl)phenyl) urea,
1-(4-((1H-pyrazolopyrimidine-4-yl)oxy)-2-chlorophenyl)-3-(4-chloro-3-(trifluoromethyl)phenyl) urea,
1-(4-((1H-pyrazolopyrimidine-4-yl)oxy)-3-fluorophenyl)-3-(3-tert-butyl-1-phenyl-1H-pyrazol-5-yl)urea,
1-(4-((1H-pyrazolopyrimidine-4-yl)oxy)-3-chlorophenyl)-3-(3-tert-butyl-1-phenyl-1H-pyrazol-5-yl)urea,
5-(3-(4-((1H-pyrazolopyrimidine-4-yl)oxy)phenyl)carbamido)-3-tert-butyl-1H-pyrazol-1-carboxylic acid,
5-(3-(4-((1H-pyrazolopyrimidine-4-yl)oxy)-3-fluoro-phenyl)carbamido)-3-tert-butyl-1H-pyrazol-1-carboxylic acid,
1-(4-((1H-pyrazolopyrimidine-4-yl)oxy)-3-fluorophenyl)-3-(3-tert-butyl-1-(4-fluoro-phenyl)-1H-pyrazol-5-yl)urea,
1-(4-((1H-pyrazolopyrimidine-4-yl)oxy)phenyl)-3-(3-tert-butyl-1-cyclopentyl-1H-pyrazol-5-yl)urea,
1-(4-((1H-pyrazolopyrimidine-4-yl)oxy)-3-fluorophenyl)-3-(3-tert-butyl-1-cyclopentyl-1H-pyrazol-5-yl)urea,
1-(4-((1H-pyrazolopyrimidine-4-yl)oxy)phenyl)-3-(3-tert-butyl-thiazol-2-yl)urea,
1-(4-((1H-pyrazolopyrimidine-4-yl)oxy)phenyl)-3-(4-phenylthiazol-2-yl)urea or
1-(4-((1H-pyrazolopyrimidine-4-yl)oxy)phenyl)-3-(benzothiazol-2-yl)urea.

Wherein, Y is oxygen, L is

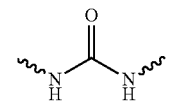

substituted at 4-position on the benzene ring of the matrix; and $R_1$ is —H; $R_2$ is —H or halogen;

$R_3$ is substituted 4-12 membered aromatic heterocyclic radical; the number of heteroatoms on the substituted aromatic heterocyclic radical is 1 to 4, the heteroatom is N, O or S; the substituent on the substituted heteroaromatic ring is —H, $C_1$-$C_6$ alkyl, substituted phenyl, —$CF_3$, 5-10 membered aromatic heterocyclic radical, carboxyl or $C_3$-$C_6$ cycloalkyl; and the substituent on the substituted aryl is —H or halogen.

Preferably, Y is oxygen, L is

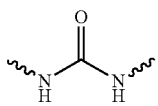

substituted at 4-position on the benzene ring of the matrix; $R_1$ is —H; and $R_2$ is —H or halogen;
$R_3$ is substituted 4-6 membered aromatic heterocyclic radical; the number of heteroatoms on the substituted aromatic heterocyclic radical is 1 to 2, the heteroatom is N or S; the substituent on the substituted heteroaromatic ring is —H, $C_1$-$C_6$ alkyl, substituted phenyl, —$CF_3$, 5-10 membered aromatic heterocyclic radical, carboxyl or $C_3$-$C_6$ cycloalkyl; and the substituent on the substituted aryl is —H or halogen.

Preferably, Y is oxygen, L is

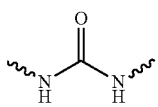

substituted at 4-position on the benzene ring of the matrix; $R_1$ is —H; and $R_2$ is —H or halogen;
$R_3$ is substituted pyrazolyl or thiazolyl; the substituent on the substituted pyrazolyl or thiazolyl is —H, $C_1$-$C_6$ alkyl, substituted phenyl, —$CF_3$, 5-10 membered aromatic heterocyclic radical, carboxyl or $C_3$-$C_6$ cycloalkyl; and the substituent on the substituted aryl is —H or halogen.

Preferably, Y is oxygen, L is

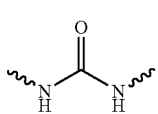

substituted at 4-position on the benzene ring of the matrix; $R_1$ is —H; and $R_2$ is —H or halogen;
$R_3$ is substituted pyrazolyl or thiazolyl; the substituent on the substituted pyrazolyl or thiazolyl is —H, $C_1$-$C_4$ alkyl, substituted phenyl, carboxyl or $C_3$-$C_6$ cycloalkyl; and the substituent on the substituted phenyl is —H or halogen.

Most preferably, Y is oxygen, L is

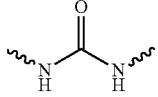

substituted at 4-position on the benzene ring of the matrix; $R_1$ is —H; and $R_2$ is —H or halogen;
$R_3$ is substituted pyrazolyl or thiazolyl; and the substituent on the substituted pyrazolyl or thiazolyl is —H, $C_1$-$C_4$ alkyl, para-fluorophenyl, carboxyl or cyclopentyl.

The invention also provides a preparation method of the pyrazolopyrimidine derivative:

When Y is oxygen or sulfur, the synthetic route of the compound of formula II, III and IV is as follows:

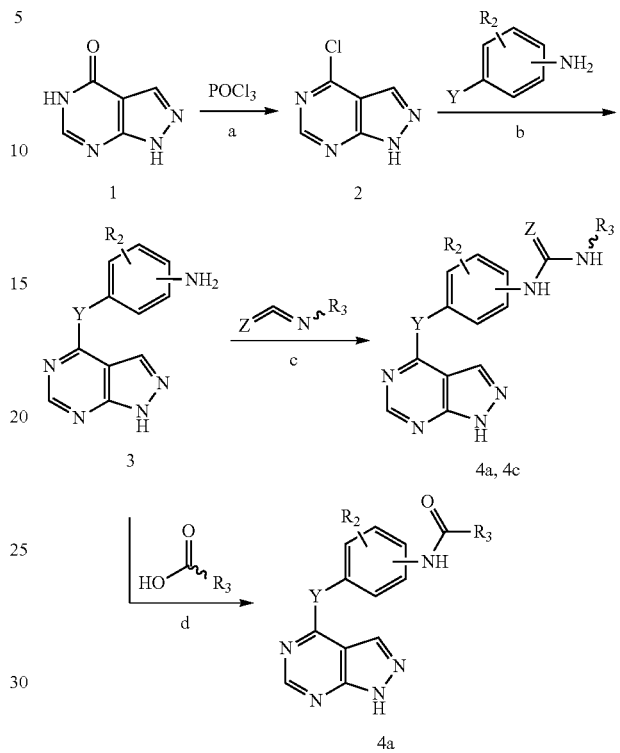

When Y is nitrogen, the synthetic route of the compound of formula II is as follows:

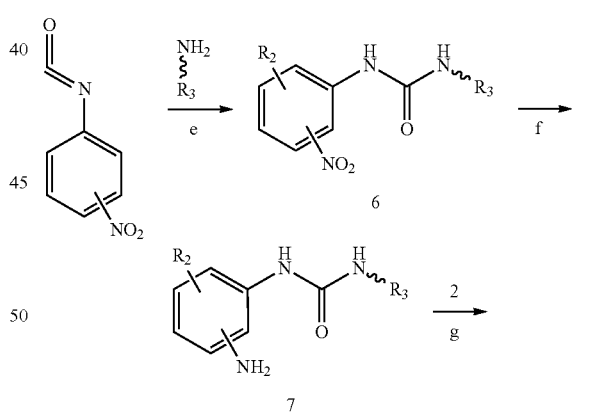

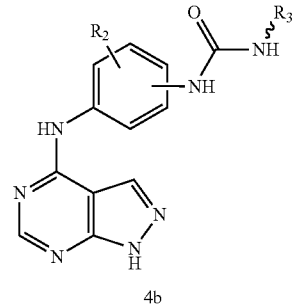

When Y is nitrogen, oxygen or sulfur, the synthetic route of type 5 compounds is as follows:

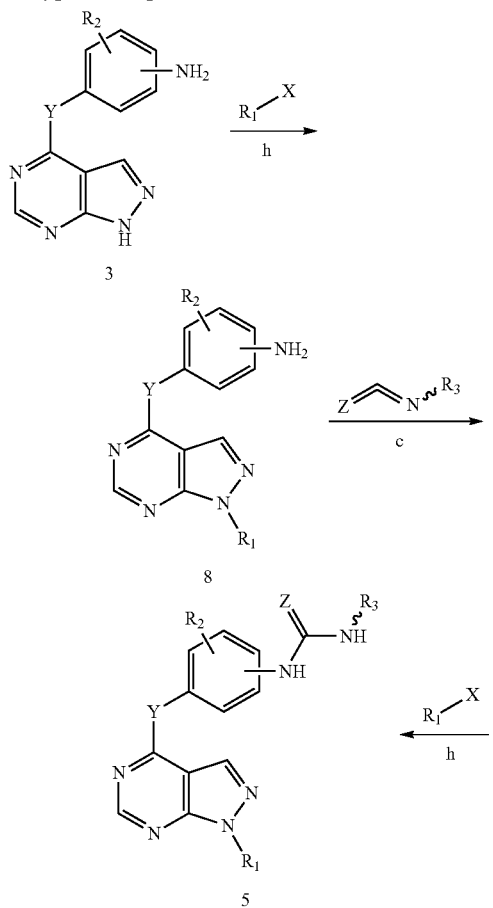

The specific reaction conditions are as follows:
a) reacting allopurinol (1) with POCl₃ to obtain compound (2);
wherein, the solvent is at least one of xylene, toluene, acetonitrile and POCl₃, the catalyst is at least one of DMF (N,N-dimethylformamide), pyridine, N,N-dimethylaniline and N,N-diethylaniline; the reaction temperature is 100° C.-125° C., preferably 120° C.; and the reaction time is 3 h-6 h.
b) reacting the compound (2) with

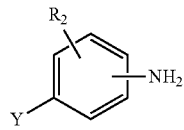

in the presence of inorganic base to obtain compound (3);
wherein, inorganic base is at least one of aqueous solutions of potassium carbonate, sodium carbonate, sodium hydroxide and potassium hydroxide; the solvent may be at least one of THF (tetrahydrofuran), acetone, DMF and dioxane; the reaction temperature is 45° C.-60° C., preferably 60° C.; and the reaction time is 1 h-2 h.
c) reacting the compound (3) with

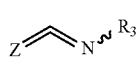

to obtain compound (4a) or (4c); wherein, the solvent is at least one of benzene, xylene, THF, acetonitrile or toluene; and the reflux reaction time is 5 h-12 h.
d) reacting the compound (3) with

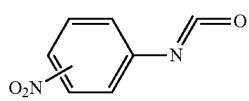

to obtain compound (4a);
wherein, the solvent may be at least one of dichloromethane, THF, acetone, DMF and dioxane; the catalyst is at least one of 1-hydroxybenzotriazole, 1-(3-dimethylaminopropyl)-3-ethylcarbodiimide hydrochloride and N,N-Diisopropylethylamine; the reaction temperature is 25° C.-60° C., preferably 60° C.; and the reaction time is 10 h-20 h.
e) reacting the compound

with R₃ substituted amine to obtain compound (6);
wherein, the solvent may be at least one of THF, acetone, DMF, acetonitrile or dioxane; and the reflux reaction time is 0.5 h-3 h.
f) reacting the compound (6) with a reducing agent to obtain compound (7);
wherein, the solvent may be organic alcohol solvent with carbon number less than 6 such as methanol, ethanol and water; the reducing agent is at least one of iron powder, stannous chloride, sodium hydrosulfite and hydrogen; the reaction time is 1 h-8 h; and the reaction temperature is 25° C.-100° C., preferably 90° C.
g) reacting the compound (7) with the compound (2) in the presence of acid to obtain compound (4b);
wherein, acid is organic and inorganic acid such as hydrochloric acid, sulfuric acid, p-toluenesulfonic acid, trifluoroacetic acid and acetic acid; the solvent is one of ethanol, isopropanol and n-butyl alcohol; the reaction temperature is 80° C.-110° C., preferably 100° C.; and the reaction time is 3 h-8 h.
h) reacting the compound (3) or the compounds (4a, 4b and 4c) with halogen substituted R₁ in the presence of basic catalyst to obtain compound (5);
wherein, inorganic base is at least one of potassium carbonate, sodium carbonate, sodium hydroxide, potassium hydroxide and sodium hydride, and organic base is at least one of triethylamine, pyridine, diethylamine and DMAP (4-dimethylaminopyridine); the solvent is at least one of methanol, ethanol, propanol, THF, acetone, DMF, dioxane, dichloromethane and ethyl acetate; the reaction time is 2 h-20 h; and the reaction temperature is 25° C.-120° C.

Wherein, X is —Cl or —Br, Y is nitrogen, oxygen or sulfur, and Z is oxygen or sulfur;
R₁ is —H, C₁-C₄ alkyl,

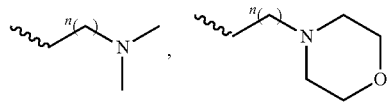

or substituted phenyl substituted methyl; and the substituent of the substituted phenyl is —H, halogen or $C_1$-$C_4$ alkyl;
$R_2$ is —H, halogen, $C_1$-$C_4$ alkyl, $C_1$-$C_4$ alkoxy or —$NO_2$;
$R_3$ is substituted 4-12 membered aromatic heterocyclic radical,

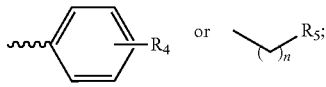

the substituent on the substituted heteroaromatic ring is —H, $C_1$-$C_6$ alkyl, aryl, —$CF_3$ or 5-10 membered aromatic heterocyclic radical; and the number of heteroatoms on the aromatic heterocyclic radical is 1 to 4, and the heteroatom is N, O or S;
$R_4$ is —H, halogen, $C_1$-$C_4$ alkyl, $C_1$-$C_4$ alkoxy, —$CF_3$, —$OCF_3$ or morpholinyl;
$R_5$ is —H, aryl or $C_3$-$C_8$ cycloalkyl; and
n=0-4.

Preferably, X is —Cl or —Br; Y is nitrogen, oxygen or sulfur, Z is oxygen or sulfur; and $R_1$ is —H, $C_1$-$C_4$ alkyl,

or substituted phenyl substituted methyl; and the substituent of the substituted phenyl is —H, —F, —Cl or —Br;
$R_2$ is —H, halogen, $C_1$-$C_4$ alkyl, $C_1$-$C_4$ alkoxy or —$NO_2$;
$R_3$ is substituted 4-12 membered aromatic heterocyclic radical,

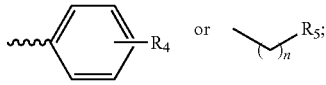

the substituent on the substituted heteroaromatic ring is —H, $C_1$-$C_6$ alkyl, aryl, —$CF_3$ or 5-10 membered aromatic heterocyclic radical; and the number of heteroatoms on the aromatic heterocyclic radical is 1 to 4, and the heteroatom is N, O or S;
$R_4$ is —H, halogen, $C_1$-$C_4$ alkyl, $C_1$-$C_4$ alkoxy, —$CF_3$, —$OCF_3$ or morpholinyl;
$R_5$ is H, aryl or $C_3$-$C_8$ cycloalkyl; and
n=0-3.

Preferably, X is —Cl or —Br; Y is nitrogen, oxygen or sulfur; Z is oxygen or sulfur; $R_1$ is —H, $C_1$-$C_4$ alkyl,

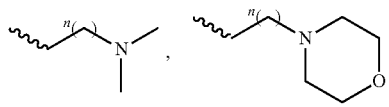

or substituted phenyl substituted methyl; and the substituent of the substituted phenyl is —H or —Br;
$R_2$ is —H, halogen, $C_1$-$C_4$ alkyl, $C_1$-$C_4$ alkoxy or —$NO_2$;
$R_3$ is substituted 4-12 membered aromatic heterocyclic radical,

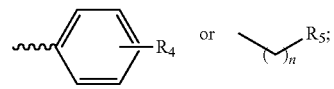

the substituent on the substituted heteroaromatic ring is —H, $C_1$-$C_6$ alkyl, aryl, —$CF_3$ or 5-10 membered aromatic heterocyclic radical; and the number of heteroatoms on the aromatic heterocyclic radical is 1 to 4, and the heteroatom is N, O or S;
$R_4$ is —H, halogen, $C_1$-$C_4$ alkyl, $C_1$-$C_4$ alkoxy, —$CF_3$, —$OCF_3$ or morpholinyl;
$R_5$ is H, aryl or $C_3$-$C_8$ cycloalkyl; and
n=0-3.

Preferably, X is —Cl or —Br; Y is nitrogen, oxygen or sulfur; Z is oxygen or sulfur; $R_1$ is —H, methyl, isopropyl,

or substituted phenyl substituted methyl; and the substituent of the substituted phenyl is —H or —Br;
$R_2$ is —H, halogen, $C_1$-$C_4$ alkyl, $C_1$-$C_4$ alkoxy or —$NO_2$;
$R_3$ is substituted 4-12 membered aromatic heterocyclic radical,

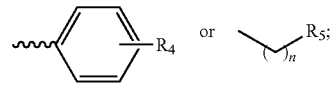

the substituent on the substituted heteroaromatic ring is —H, $C_1$-$C_6$ alkyl, aryl, —$CF_3$ or 5-10 membered aromatic heterocyclic radical; and the number of heteroatoms on the aromatic heterocyclic radical is 1 to 4, and the heteroatom is N, O or S;
$R_4$ is —H, halogen, $C_1$-$C_4$ alkyl, $C_1$-$C_4$ alkoxy, —$CF_3$, —$OCF_3$ or morpholinyl;
$R_5$ is H, aryl or $C_3$-$C_8$ cycloalkyl; and
n=0-3.

Further preferably, X is —Cl or —Br; Y is nitrogen, oxygen or sulfur; Z is oxygen or sulfur; $R_1$ is —H, $C_1$-$C_4$ alkyl,

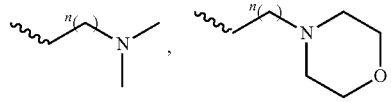

or substituted phenyl substituted methyl; and the substituent of the substituted phenyl is —H, halogen or $C_1$-$C_4$ alkyl;
$R_2$ is —H, —F, —Cl, —Br, $C_1$-$C_4$ alkyl, $C_1$-$C_4$ alkoxy or —$NO_2$;
$R_3$ is substituted 4-12 membered aromatic heterocyclic radical,

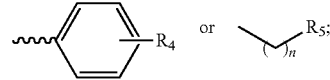

the substituent on the substituted heteroaromatic ring is —H, $C_1$-$C_6$ alkyl, aryl, —$CF_3$ or 5-10 membered aromatic heterocyclic radical; and the number of heteroatoms on the aromatic heterocyclic radical is 1 to 4, and the heteroatom is N, O or S;
$R_4$ is —H, halogen, $C_1$-$C_4$ alkyl, $C_1$-$C_4$ alkoxy, —$CF_3$, —$OCF_3$ or morpholinyl;
$R_5$ is —H, aryl or $C_3$-$C_8$ cycloalkyl; and
n=0-4.

Preferably, X is —Cl or —Br; Y is nitrogen, oxygen or sulfur; Z is oxygen or sulfur; $R_1$ is —H, $C_1$-$C_4$ alkyl,

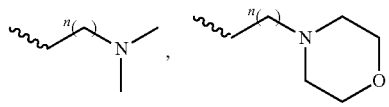

or substituted phenyl substituted methyl; and the substituent of the substituted phenyl is —H, halogen or $C_1$-$C_4$ alkyl;
$R_2$ is —H, —F, —Cl, methyl, methoxy or —$NO_2$;
$R_3$ is substituted 4-12 membered aromatic heterocyclic radical,

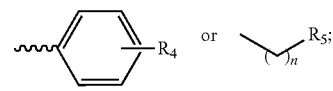

the substituent on the substituted heteroaromatic ring is —H, $C_1$-$C_6$ alkyl, aryl, —$CF_3$ or 5-10 membered aromatic heterocyclic radical; and the number of heteroatoms on the aromatic heterocyclic radical is 1 to 4, and the heteroatom is N, O or S;
$R_4$ is —H, halogen, $C_1$-$C_4$ alkyl, $C_1$-$C_4$ alkoxy, —$CF_3$, —$OCF_3$ or morpholinyl;
$R_5$ is —H, aryl or $C_3$-$C_8$ cycloalkyl; and
n=0-3.

Further preferably, X is —Cl or —Br; Y is nitrogen, oxygen or sulfur; Z is oxygen or sulfur; $R_1$ is —H, $C_1$-$C_4$ alkyl,

or substituted phenyl substituted methyl; and the substituent of the substituted phenyl is —H, halogen or $C_1$-$C_4$ alkyl;
$R_2$ is —H, halogen, $C_1$-$C_4$ alkyl, $C_1$-$C_4$ alkoxy or —$NO_2$;
$R_3$ is substituted 5-10 membered aromatic heterocyclic radical,

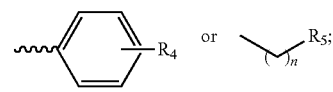

the substituent on the substituted heteroaromatic ring is —H, $C_1$-C4 alkyl, aryl, —$CF_3$ or quinolyl; and the number of heteroatoms on the aromatic heterocyclic radical is 1 to 3, and the heteroatom is N or O;

$R_4$ is —H, halogen, $C_1$-$C_4$ alkyl, $C_1$-$C_4$ alkoxy, —$CF_3$, —$OCF_3$ or morpholinyl;
$R_5$ is —H, aryl or $C_3$-$C_8$ cycloalkyl; and
n=0-4.

Preferably, X is —Cl or —Br; Y is nitrogen, oxygen or sulfur; Z is oxygen or sulfur; $R_1$ is —H, $C_1$-$C_4$ alkyl,

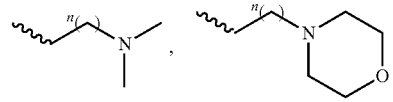

or substituted phenyl substituted methyl; and the substituent of the substituted phenyl is —H, halogen or $C_1$-$C_4$ alkyl;
$R_2$ is —H, halogen, $C_1$-$C_4$ alkyl, $C_1$-$C_4$ alkoxy or —$NO_2$;
$R_3$ is substituted pyrazolyl, substituted isoxazolyl, substituted quinolyl, substituted pyridyl,

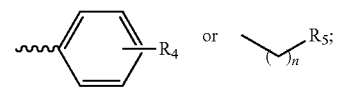

and the substituent is —H, $C_1$-$C_4$ alkyl, phenyl, —$CF_3$ or quinolyl;
$R_4$ is —H, halogen, $C_1$-$C_4$ alkyl, $C_1$-$C_4$ alkoxy, —$CF_3$, —$OCF_3$ or morpholinyl;
$R_5$ is —H, aryl or $C_3$-$C_8$ cycloalkyl; and
n=0-3.

Further preferably, X is —Cl or —Br; Y is nitrogen, oxygen or sulfur; Z is oxygen or sulfur; $R_1$ is —H, $C_1$-$C_4$ alkyl,

or substituted phenyl substituted methyl; and the substituent of the substituted phenyl is —H, halogen or $C_1$-$C_4$ alkyl;
$R_2$ is —H, halogen, $C_1$-$C_4$ alkyl, $C_1$-$C_4$ alkoxy or —$NO_2$;
$R_3$ is substituted 4-12 membered aromatic heterocyclic radical,

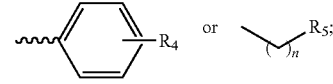

the substituent on the substituted heteroaromatic ring is —H, $C_1$-$C_6$ alkyl, aryl, —$CF_3$ or 5-10 membered aromatic heterocyclic radical; and the number of heteroatoms on the aromatic heterocyclic radical is 1 to 4, and the heteroatom is N or O;
$R_4$ is —H, —F, —Cl, —Br, $C_1$-$C_4$ alkyl, $C_1$-$C_4$ alkoxy, —$CF_3$, —$OCF_3$ or morpholinyl;
$R_5$ is —H, aryl or $C_3$-$C_8$ cycloalkyl; and
n=0-4.

Preferably, X is —Cl or —Br; Y is nitrogen, oxygen or sulfur; Z is oxygen or sulfur; $R_1$ is —H, $C_1$-$C_4$ alkyl,

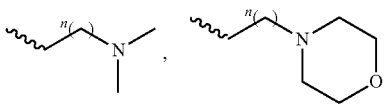

or substituted phenyl substituted methyl; and the substituent of the substituted phenyl is —H, halogen or $C_1$-$C_4$ alkyl;
$R_2$ is —H, halogen, $C_1$-$C_4$ alkyl, $C_1$-$C_4$ alkoxy or —$NO_2$;
$R_3$ is substituted 4-12 membered aromatic heterocyclic radical,

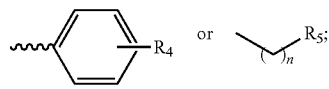

the substituent on the substituted heteroaromatic ring is —H, $C_1$-$C_6$ alkyl, aryl, —$CF_3$ or 5-10 membered aromatic heterocyclic radical; and the number of heteroatoms on the aromatic heterocyclic radical is 1 to 4, and the heteroatom is N or O;
$R_4$ is —H, —F, —Cl, —Br, methyl, isopropyl, methoxy, —$CF_3$, —$OCF_3$ or morpholinyl;
$R_5$ is —H, aryl or $C_3$-$C_8$ cycloalkyl; and
n=0-3.

Further preferably, X is —Cl or —Br; Y is nitrogen, oxygen or sulfur; Z is oxygen or sulfur; $R_1$ is —H, $C_1$-$C_4$ alkyl,

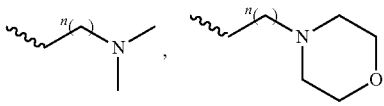

or substituted phenyl substituted methyl; and the substituent of the substituted phenyl is —H, halogen or $C_1$-$C_4$ alkyl;
$R_2$ is —H, halogen, $C_1$-$C_4$ alkyl, $C_1$-$C_4$ alkoxy or —$NO_2$;
$R_3$ is substituted 4-12 membered aromatic heterocyclic radical,

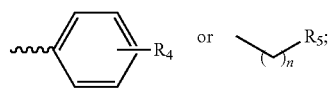

the substituent on the substituted heteroaromatic ring is —H, $C_1$-$C_6$ alkyl, aryl, —$CF_3$ or 5-10 membered aromatic heterocyclic radical; and the number of heteroatoms on the aromatic heterocyclic radical is 1 to 4, and the heteroatom is N or O;
$R_4$ is —H, halogen, $C_1$-$C_4$ alkyl, $C_1$-$C_4$ alkoxy, —$CF_3$, —$OCF_3$ or morpholinyl;
$R_5$ is —H, phenyl or $C_3$-$C_8$ cycloalkyl; and
n=0-4.

Preferably, X is —Cl or —Br; Y is nitrogen, oxygen or sulfur; Z is oxygen or sulfur; $R_1$ is —H, $C_1$-$C_4$ alkyl,

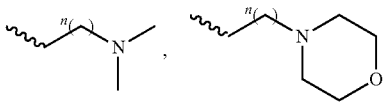

or substituted phenyl substituted methyl; and the substituent of the substituted phenyl is —H, halogen or $C_1$-$C_4$ alkyl;
$R_2$ is —H, halogen, $C_1$-$C_4$ alkyl, $C_1$-$C_4$ alkoxy or —$NO_2$;
$R_3$ is substituted 4-12 membered aromatic heterocyclic radical,

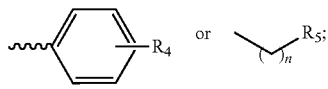

the substituent on the substituted heteroaromatic ring is —H, $C_1$-$C_6$ alkyl, aryl, —$CF_3$ or 5-10 membered aromatic heterocyclic radical; and the number of heteroatoms on the aromatic heterocyclic radical is 1 to 4, and the heteroatom is N or O;
$R_4$ is —H, halogen, $C_1$-$C_4$ alkyl, $C_1$-$C_4$ alkoxy, —$CF_3$, —$OCF_3$ or morpholinyl;
$R_5$ is —H, phenyl or cyclohexyl; and
n=0-3.

Most preferably, X is —Cl or —Br; Y is nitrogen, oxygen or sulfur; Z is oxygen or sulfur; $R_1$ is —H, methyl, isopropyl,

or p-bromobenzyl;
$R_2$ is —H, —F, —Cl, methyl, methoxy or —$NO_2$;
$R_3$ is substituted pyrazolyl, substituted isoxazolyl, substituted quinolyl, substituted pyridyl,

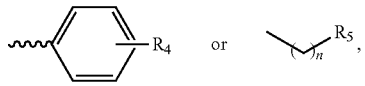

and the substituent is —H, $C_1$-$C_4$ alkyl, phenyl, —$CF_3$ or quinolyl;
$R_4$ is —H, —F, —Cl, —Br, methyl, isopropyl, methoxy, —$CF_3$, —$OCF_3$ or morpholinyl;
$R_5$ is —H, phenyl or cyclohexyl; and
n=0-3.

The invention also provides a pharmaceutically acceptable salt of the pyrazolopyrimidine derivative.

The invention also provides prodrugs of the compound. According to the invention, the prodrugs are derivatives of the compound, and have weak activity or no activity, but are transformed into biologically active forms under physiological conditions (e.g. by metabolism, solvolysis or other method) upon administration.

The invention also provides a pharmaceutically acceptable hydrate of the pyrazolopyrimidine derivative.

The invention also provides a pharmaceutical composition prepared from the pyrazolopyrimidine derivative of the invention and pharmaceutically acceptable auxiliary components. The structure of the pyrazolopyrimidine derivative of the invention is shown as formula I to IV.

The invention also provides uses of the pyrazolopyrimidine derivative and salt or hydrate thereof in preparation of kinase inhibitors.

Further, the kinase inhibitor is a drug inhibiting at least one of human Fms-like tyrosine kinase 3 (FLT3), vascular endothelial growth factor receptor 2 (VEGFR2), human Fms-like tyrosine kinase 1 (FLT1), human Fms-like tyrosine kinase 4 (FLT4), RET receptor tyrosine kinase (RET), cRAF serine/threonine protein kinase (cRAF), B-RAF serine/threonine protein kinase (B-RAF), tyrosine protein kinase KIT (c-KIT), platelet derived growth factor receptor α (PDGF$_\alpha$), platelet derived growth factor receptor β (PDGF$_\beta$), fibroblast growth factor receptor 2 (FGFR2), fibroblast growth factor receptor 1 (FGFR1), EphA2 tyrosine kinase (EphA2), EphB2 tyrosine kinase (EphB2), SRC tyrosine kinase (SRC), ABL tyrosine kinase (ABL), anaplastic lymphoma kinase (ALK) and Met tyrosine kinase (Met).

The invention also provides uses of the pyrazolopyrimidine derivative and salt or hydrate thereof in preparation of antitumor drugs.

Further, the tumor refers to leukemia or solid tumor.

Further, the solid tumor is at least one of pulmonary carcinoma, breast carcinoma, thyroid tumor, gastric carcinoma, malignant melanoma, pancreatic carcinoma, cervical carcinoma, glioma and colorectal carcinoma, wherein the leukemia is acute myeloid leukemia or mixed leukemia.

The experiments of the invention indicate that the pyrazolopyrimidine derivative shows better inhibition effect on human leukemia, human thyroid tumor, human gastric carcinoma, human malignant melanoma, human pancreatic carcinoma, human cervical carcinoma, human colorectal carcinoma, etc.

The invention also provides uses of the pyrazolopyrimidine derivative and salt or hydrate thereof in preparation of medicines for autoimmune diseases.

Further, the autoimmune disease is at least one of systemic lupus erythematosus, rheumatic arthritis, psoriasis, multiple sclerosis and inflammatory-immune disease.

The invention also provides uses of the pyrazolopyrimidine derivative and salt or hydrate thereof in preparation of tumor angiogenesis inhibitors.

The invention provides a new pyrazolopyrimidine derivative mainly having position 4 substituted and a simple, efficient and low-cost preparation method thereof. The pyrazolopyrimidine derivative of the invention has good inhibitory activity for multiple kinases; has inhibitory effect on multiple solid tumors, leukemia and autoimmune diseases; provides a new effective choice for preparation of kinase inhibitors, medicines for autoimmune diseases, angiogenesis inhibitors and antitumor drugs; and has good application prospect.

DESCRIPTION OF THE PREFERRED EMBODIMENTS

Example 1: Preparation of 4-chloro-1H-pyrazolopyrimidine (2)

Figure 1:
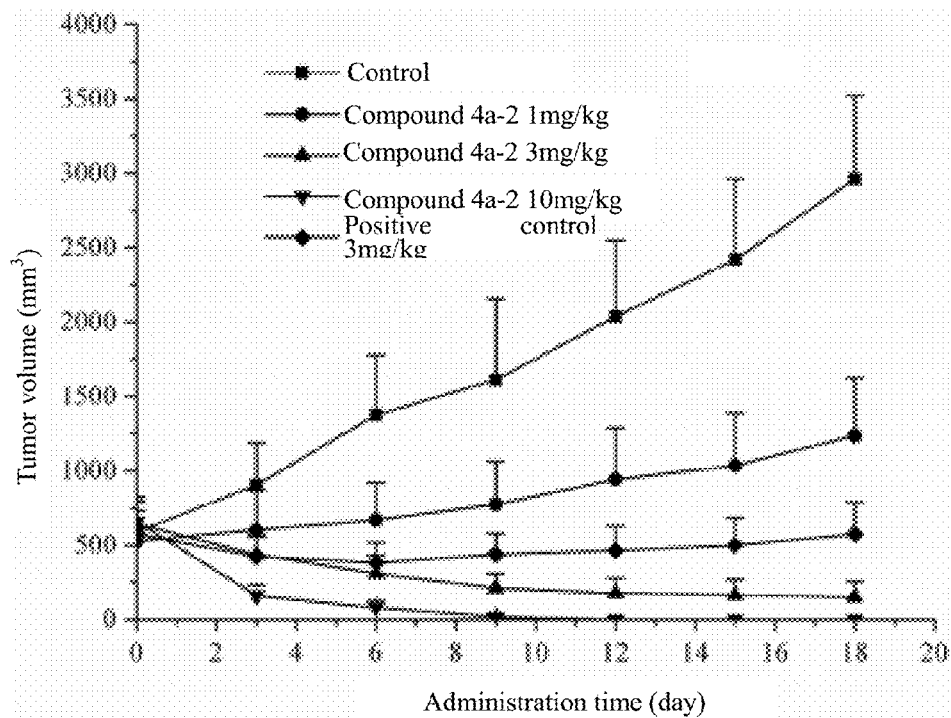
FIG. 1 shows tumor inhibition curve of compound 4a-2 in nude mice-subcutaneous human leukemia MV4-11 model.

Ten mL phosphorus oxychloride (POCl$_3$) was added to 5 g allopurinol (compound 1), and DMF (5 mL N,N-dimethylformamide) was dropwise added slowly at 0° C., then DMA (1 mL N,N-dimethylaniline) was dropwise added slowly, and temperature of the reaction system was increased to 120° C. for 5 h reaction after resulting mixture was stirred at normal temperature for several minutes. Upon thorough cooling of the reaction product, a large amount of ice water was added to quench excessive phosphorus oxychloride, then the reaction product was extracted twice with ethyl acetate, and the ethyl acetate layer was spun dry to obtain 3.2 g solid at a yield of 56.4%.

$^1$H NMR (400 MHz, DMSO-d$_6$): δ 14.12 (s, 1H), 9.32 (s, 1H), 7.55 (s, 1H) ppm.

Example 2: Preparation of 4-((1H-pyrazolopyrimidine-4-yl)oxy)aniline (3a-1)

P-aminophenol (0.55 g, 5.5 mmol) and sodium hydroxide (0.20 g, 5.5 mmol) were added to 10 mL water; potassium carbonate (0.76 g, 5.5 mmol) was added after resulting mixture was stirred for 30 minutes at normal temperature; the temperature was increased to 60° C., and tetrahydrofuran solution of 4-chloro-1H-pyrazolopyrimidine (intermediate 2) (0.94 g, 6.6 mmol) was slowly added to the reaction solution; after one hour, reaction was stopped; after the tetrahydrofuran of the reaction system was distilled to dryness, the remaining system was extracted with ethyl acetate and water twice; the ethyl acetate layer was dried with anhydrous magnesium sulfate and then spun dry, and then introduced into a column for purification to obtain 0.77 g 4-((1H-pyrazolo-4-yl)oxy)aniline (3a-1) at a yield of 62.1%.

$^1$H NMR (400 MHz, DMSO-d$_6$): δ 14.07 (s, 1H), 8.50 (s, 1H), 7.67 (s, 1H), 6.96 (d, J=8.8 Hz, 2H), 6.64 (d, J=8.8 Hz, 2H), 5.20 (s, 2H) ppm. LCMS m/z: 228.1 [M+H].

Example 3: Preparation of 4-((1H-pyrazolopyrimidine-4-yl)oxy)-2-methylaniline (3a-2)

An intermediate (3a-2) was obtained from the intermediate (2) and 4-amino-3-methylphenol by the synthesis method of the intermediate (3a-1) at a yield of 64.2%.

$^1$H NMR (400 MHz, DMSO-d$_6$): δ 14.04 (s, 1H), 8.49 (s, 1H), 7.65 (s, 1H), 6.89 (d, J=2.4 Hz, 1H), 6.85 (d, J=8.0 Hz, 1H), 6.68 (d, J=8.4 Hz, 1H), 4.94 (s, 2H), 2.08 (s, 3H) ppm.

Example 4: Preparation of 4-(1H-pyrazolopyrimidine-4-sulfydryl)-aniline (3c-3)

An intermediate (3c-3) was obtained from the intermediate (2) and p-aminothiophenol by the synthesis method of the intermediate (3a-1) at a yield of 94.2%.

¹H NMR (400 MHz, DMSO-d₆): δ 13.98 (s, 1H), 8.61 (s, 1H), 7.37 (d, J=9.2 Hz, 2H), 6.72 (d, J=8.0 Hz, 2H), 6.62 (s, 1H), 5.86 (s, 2H) ppm.

Example 5: Preparation of 1-(4-((1H-pyrazolopyrimidine-4-yl)oxy)phenyl)-3-(4-trifluoromethyl)phenyl)urea (4a-1)

4-(trifluoromethyl)aniline (1.6 g, 10 mmol) was dissolved in 50 mL tetrahydrofuran; dropwise added to the tetrahydrofuran solution of triphosgene (2.98, 10 mmol) slowly; several minutes after dropwise addition of aniline, 3 mL triethylamine was added to the reaction solution and stirred for several minutes; After tetrahydrofuran in the reaction solution was distilled to dryness, 4-(1H-(pyrazolopyrimidine-4-yl)oxy)aniline (3a-1, 1.8 g, 8 mmol) was added to allow reaction for 8 h reaction at 90° C. with acetonitrile as solvent. The acetonitrile was spun dry, and washed with water and acetone to obtain 2.3 g product (4a-1) at a yield of 71.0%.

¹H NMR (400 MHz, DMSO-d₆): δ 14.15 (s, 1H), 9.13 (s, 1H), 8.97 (s, 1H), 8.51 (s, 1H), 8.04 (s, 1H), 7.60-7.51 (m, 5H), 7.32 (d, J=7.2 Hz, 1H), 7.24 (d, J=8.8 Hz, 2H), 7.27 (d, J=8.8 Hz, 2H) ppm.

Example 6: Preparation of 1-(4-((1H-pyrazolopyrimidine-4-yl)oxy)phenyl)-3-(4-chloro-3-(trifluoromethyl)phenyl)urea (4a-2)

A compound (4a-2) was obtained from the intermediate (3a-1) and 4-chloro-3-trifluoromethyl-phenyl isocyanate by the synthesis method of the compound (4a-1) at a yield of 70.1%.

¹H NMR (400 MHz, DMSO-d₆): δ 14.14 (s, 1H), 9.26 (s, 1H), 9.02 (s, 1H), 8.50 (s, 1H), 8.12 (s, 1H), 8.05 (s, 1H), 7.64 (d, J=7.2 Hz, 2H), 7.56 (d, J=8.4 Hz, 2H), 7.25 (d, J=8.4 Hz, 2H) ppm.

Example 7: Preparation of 1-(4-((1H-pyrazolopyrimidine-4-yl)oxy)phenyl)-3-(4-bromophenyl)urea (4a-3)

A compound (4a-3) was obtained from the intermediate (3a-1) and 4-bromo-phenyl isocyanate by the synthesis method of the compound (4a-1) at a yield of 70.8%.

¹H NMR (400 MHz, DMSO-d₆): δ 14.14 (s, 1H), 8.87 (d, J=10.8 Hz, 2H), 8.89 (s, 1H), 8.50 (s, 1H), 8.04 (s, 1H), 7.54 (d, J=8.8 Hz, 2H), 7.42 (d, J=17.6 Hz, 4H), 7.24 (d, J=8.8 Hz, 2H) ppm.

Example 8: Preparation of 1-(4-((1H-pyrazolopyrimidine-4-yl)oxy)phenyl)-3-(2,3-dimethylphenyl)urea (4a-4)

A compound (4a-4) was obtained from the intermediate (3a-1) and 2.3-dimethyl-phenyl isocyanate by the synthesis method of the compound (4a-1) at a yield of 72.8%.

¹H NMR (400 MHz, DMSO-d₆): δ 14.13 (s, 1H), 9.06 (s, 1H), 8.51 (s, 1H), 8.00 (s, 1H), 7.55 (t, J=13.6 3H), 7.24 (d, J=8.8 Hz, 2H), 7.04 (t, J=15.2 Hz, 1H), 6.91 (d, J=7.2 Hz, 1H), 2.24 (s, 3H), 2.12 (s, 3H) ppm.

Example 9: Preparation of 1-(4-((1H-pyrazolopyrimidine-4-yl)oxy)phenyl)-3-(3-methoxyphenyl)urea (4a-5)

A compound (4a-5) was obtained from the intermediate (3a-1) and 3-methoxy-phenyl isocyanate by the synthesis method of the compound (4a-1) at a yield of 71.2%.

¹H NMR (400 MHz, DMSO-d₆): δ 14.14 (s, 1H), 8.79 (s, 1H), 8.73 (s, 1H), 8.51 (s, 1H), 8.03 (s, 1H), 7.60 (d, J=8.8 Hz 2H), 7.26-7.21 (m, 4H), 6.96 (d, J=8.0 Hz, 1H), 6.57 (dd, J=2.0 Hz, J=6.0 Hz, 1H), 3.74 (s, 3H) ppm.

Example 10: Preparation of 1-(4-((1H-pyrazolopyrimidine-4-yl)oxy)phenyl)-3-(3-trifluoromethyl)phenyl)urea (4a-6)

A compound (4a-6) was obtained from the intermediate (3a-1) and 3-trifluoromethyl-phenyl isocyanate by the synthesis method of the compound (4a-1) at a yield of 71.8%.

¹H NMR (400 MHz, DMSO-d₆): δ 14.14 (s, 1H), 9.12 (s, 1H), 8.95 (s, 1H), 8.51 (s, 1H), 8.04 (d, J=4.0 Hz, 2H), 7.61-7.51 (m, 4H), 7.32 (d, J=7.6 Hz, 1H), 7.26 (d, J=8.4 Hz, 2H) ppm.

Example 11: Preparation of 1-(4-((1H-pyrazolopyrimidine-4-yl)oxy)-3-fluorophenyl)-3-(3-isopropylphenyl)urea (4a-7)

A compound (4a-7) was obtained from the intermediate (3a-1) and 3-isopropyl-phenyl isocyanate by the synthesis method of the compound (4a-1) at a yield of 70.2%.

¹H NMR (400 MHz, DMSO-d₆): δ 14.13 (s, 1H), 8.77 (s, 1H), 8.66 (s, 1H), 8.51 (s, 1H), 8.01 (s, 2H), 7.55 (d, J=8.8 Hz, 2H), 7.36 (s, 1H), 7.28-7.20 (m, 4H), 6.87 (d, J=7.6 Hz, 1H), 2.87-2.83 (m, 1H), 1.20 (d, J=6.8 Hz, 6H) ppm.

Example 12: Preparation of 1-(4-((1H-pyrazolopyrimidine-4-yl)oxy)-3-fluorophenyl)-3-(3-trifluoromethoxy)phenyl)urea (4a-8)

A compound (4a-8) was obtained from the intermediate (3a-1) and 3-trifluoromethoxy-phenyl isocyanate by the synthesis method of the compound (4a-1) at a yield of 72.6%.

¹H NMR (400 MHz, DMSO-d₆): δ 14.13 (s, 1H), 9.06 (s, 1H), 8.91 (s, 1H), 8.51 (s, 1H), 8.04 (s, 1H), 7.61 (s, 1H), 7.52 (d, J=8.0 Hz, 2H), 7.32 (m, 1H), 7.18 (d, J=7.2 Hz, 1H), 6.92 (d, J=6.4 Hz, 2H), 6.82 (d, J=6.4 Hz, 1H) ppm. LCMS m/z: 431.1 [M+H].

Example 13: Preparation of 1-(4-((1H-pyrazolopyrimidine-4-yl)oxy)-3-fluorophenyl)-3-(4-(trifluoromethyl)phenyl)urea (4a-9)

A compound (4a-9) was obtained from the intermediate 4-(pyrazolopyrimidine-4-phenoxy)-3-fluoroaniline and 4-trifluoromethyl-phenyl isocyanate by the synthesis method of the compound (4a-1) at a yield of 70.0%.

¹H NMR (400 MHz, DMSO-d₆): δ 14.24 (s, 1H), 9.25 (s, 1H), 9.14 (s, 1H), 8.52 (s, 1H), 8.32 (s, 1H), 7.70-7.64 (m, 5H), 7.42 (t, J=8.4 Hz, 1H), 7.25 (d, J=8.4 Hz, 1H) ppm.

Example 14: Preparation of 1-(4-((1H-pyrazolopyrimidine-4-yl)oxy)-3-fluorophenyl)-3-(4-chloro-3-(trifluoromethyl)phenyl)urea (4a-10)

A compound (4a-10) was obtained from the intermediate 4-(pyrazolopyrimidine-4-phenoxy)-3-fluoroaniline and 4-chloro-3-trifluoromethyl-phenyl isocyanate by the synthesis method of the compound (4a-1) at a yield of 72.6%.

MS m/z 467.1[M+H].

Example 15: Preparation of 1-(4-((1H-pyrazolopyrimidine-4-yl)oxy)-2-methylphenyl)-3-(3-(trifluoromethyl)phenyl)urea (4a-11)

A compound (4a-11) was obtained from the intermediate (3a-2) and 3-trifluoromethyl-phenyl isocyanate by the synthesis method of the compound (4a-1) at a yield of 70.6%. MS m/z 429.1 [M+Na].

Example 16: Preparation of 1-(4-((1H-pyrazolopyrimidine-4-yl)oxy)phenyl)-3-(3,5-bis(trifluoromethyl)phenyl)urea (4a-12)

A compound (4a-12) was obtained from the intermediate (3a-1) and 3,5-bis(trifluoromethyl)-phenyl isocyanate by the synthesis method of the compound (4a-1) at a yield of 73.0%.

$^1$H NMR (400 MHz, DMSO-$d_6$): δ 14.14 (s, 1H), 9.46 (s, 1H), 9.13 (s, 1H), 8.51 (s, 1H), 8.16 (s, 2H), 8.05 (s, 1H), 7.65 (s, 1H), 7.60 (d, J=8.8 Hz, 2H), 7.28 (d, J=8.8 Hz, 2H) ppm. LCMS m/z: 483.2 [M+H].

Example 17: Preparation of 1-(4-((1H-pyrazolopyrimidine-4-yl)oxy)phenyl)-3-(2-chloro-4-(trifluoromethyl)phenyl)urea (4a-13)

A compound (4a-13) was obtained from the intermediate (3a-1) and 2-chloro-4-trifluoromethyl-phenyl isocyanate by the synthesis method of the compound (4a-1) at a yield of 71.7%.

$^1$H NMR (400 MHz, DMSO-$d_6$): 14.14 (s, 1H), 9.11 (s, 1H), 8.96 (s, 1H), 8.50 (s, 1H), 8.04 (s, 1H), 7.80 (s, 1H), 7.68 (d, J=7.2 Hz 1H), 7.45-7.48 (m, 4H), 6.86 (d, J=8.4 Hz, 2H) ppm.

Example 18: Preparation of 1-(4-((1H-pyrazolopyrimidine-4-yl)oxy)phenyl)-3-(3-fluorophenyl)urea (4a-14)

A compound (4a-14) was obtained from the intermediate (3a-1) and 3-fluoro-phenyl isocyanate by the synthesis method of the compound (4a-1) at a yield of 71.6%.

$^1$H NMR (400 MHz, DMSO-$d_6$): δ 14.15 (s, 1H), 8.98 (s, 1H), 8.89 (s, 1H), 8.52 (s, 1H), 8.05 (s, 1H), 7.57 (d, J=8.8 Hz, 2H), 7.52 (d, J=12.0 Hz, 1H), 7.32 (d, J=7.2 Hz, 1H), 7.27 (d, J=8.8 Hz, 2H), 7.15 (d, J=7.6 Hz, 1H), 6.80 (t, J=8.4 Hz, 1H) ppm.

Example 19: Preparation of 1-(4-((1H-pyrazolopyrimidine-4-yl)oxy)phenyl)-3-phenylurea (4a-15)

A compound (4a-15) was obtained from the intermediate (3a-1) and phenyl isocyanate by the synthesis method of the compound (4a-1) at a yield of 69.0%.

$^1$H NMR (400 MHz, DMSO-$d_6$): δ 14.14 (s, 1H), 8.81 (s, 1H), 8.73 (s, 1H), 8.51 (s, 1H), 8.03 (s, 1H), 7.56 (d, J=8.4 Hz, 2H), 7.47 (d, J=7.6 Hz, 1H), 7.31-7.24 (m, 4H), 6.98 (t, J=7.2 Hz, 1H) ppm. LCMS m/z: 347.1 [M+H].

Example 20: Preparation of 1-(4-((1H-pyrazolopyrimidine-4-yl)oxy)phenyl)-3-(4-morpholinylphenyl)urea (4a-16)

A compound (4a-16) was obtained from the intermediate (3a-1) and 4-morpholinyl-phenyl isocyanate by the synthesis method of the compound (4a-1) at a yield of 71.8%.

$^1$H NMR (400 MHz, DMSO-$d_6$): δ 14.16 (s, 1H), 9.12 (s, 1H), 8.99 (s, 1H), 8.51 (s, 1H), 8.04 (s, 1H), 7.61-7.52 (m, 4H), 7.31 (d, J=8.0 Hz, 2H), 7.28 (d, J=8.8 Hz, 2H), 3.76 (br s, 4H), 3.12 (br s, 4H) ppm. LCMS m/z: 432.2[M+H].

Example 21: Preparation of 1-(4-((1H-pyrazolopyrimidine-4-yl)oxy)phenyl)-3-(4-fluorophenyl)urea (4a-17)

A compound (4a-17) was obtained from the intermediate (3a-1) and 4-fluoro-phenyl isocyanate by the synthesis method of the compound (4a-1) at a yield of 72.8%.

$^1$H NMR (400 MHz, DMSO-$d_6$): δ 14.12 (s, 1H), 8.80 (s, 1H), 8.75 (s, 1H), 8.51 (s, 1H), 8.02 (s, 2H), 7.55 (d, J=8.0 Hz, 2H), 7.48 (t, J=8.8 Hz, 2H), 7.25 (d, J=8.0 Hz, 2H), 7.13 (t, J=8.0 Hz, 2H) ppm. LCMS m/z: 365.1 [M+H].

Example 22: Preparation of (S)-1-(4-((1H-pyrazolopyrimidine-4-yl)oxy)phenyl)-3-(1-phenethyl)urea (4a-18)

A compound (4a-18) was obtained from the intermediate (3a-1) and (S)-2-methylbenzyl isocyanate by the synthesis method of the compound (4a-1) at a yield of 74.6%.

$^1$H NMR (400 MHz, DMSO-$d_6$): δ 14.12 (s, 1H), 8.51 (d, J=8.8 Hz 1H), 7.96 (s, 1H), 7.47 (d, J=8.4 Hz, 1H), 7.36 (s, 4H), 7.26 (s, 2H), 7.18 (d, J=8.4 Hz, 2H), 6.98 (d, J=7.2 Hz, 2H), 4.86-4.83 (m, 1H), 1.41 (d, J=6.4 Hz, 3H) ppm.

Example 23: Preparation of (R)-1-(4-((1H-pyrazolopyrimidine-4-yl)oxy)phenyl)-3-(1-phenethyl)urea (4a-19)

A compound (4a-19) was obtained from the intermediate (3a-1) and (R)-2-methylbenzyl isocyanate by the synthesis method of the compound (4a-1) at a yield of 74.0%.

$^1$H NMR (400 MHz, DMSO-$d_6$): δ 14.15 (s, 1H), 8.55 (s, 1H), 8.49 (s, 1H), 7.95 (s, 1H), 7.47 (d, J=7.2 Hz, 2H), 7.36 (d, J=4.0 Hz, 4H), 7.25 (m, 1H), 7.18 (d, J=8.8 Hz, 2H), 6.68 (d, J=7.6 Hz, 1H), 4.84 (m, 1H), 1.41 (d, J=6.8 Hz, 3H) ppm. LCMS m/z: 375.4 [M+H].

Example 24: Preparation of 1-(4-((1H-pyrazolopyrimidine-4-yl)oxy)phenyl)-3-(methylcyclohexyl)urea (4a-20)

A compound (4a-20) was obtained from the intermediate (3a-1) and cyclohexanemethyl isocyanate by the synthesis method of the compound (4a-1) at a yield of 52.1%.

$^1$H NMR (400 MHz, DMSO-$d_6$): δ 14.11 (s, 1H), 8.50 (s, 1H), 8.44 (s, 2H), 7.94 (s, 1H), 7.46 (d, J=9.2 Hz, 2H), 7.17 (d, J=8.8 Hz, 2H), 6.11 (d, J=7.6 Hz, 1H), 3.50-3.45 (m, 1H), 1.83-1.80 (m, 2H), 1.68-65 (m, 2H), 1.56-1.53 (m, 1H), 1.36-1.28 (m, 2H), 1.22-1.16 (m, 3H) ppm. LCMS m/z: 353.2 [M+H].

Example 25: Preparation of 1-(4-((1H-pyrazolopyrimidine-4-yl)oxy)phenyl)-3-cyclohexylurea (4a-21)

A compound (4a-21) was obtained from the intermediate (3a-1) and cyclohexyl isocyanate by the synthesis method of the compound (4a-1) at a yield of 48.7%.

LCMS m/z 353.2[M+H].

Example 26: Preparation of 1-(4-((1H-pyrazolopyrimidine-4-yl)oxy)phenyl)-3-(6-quinolyl)urea (4a-22)

A compound (4a-22) was obtained from the intermediate (3a-1) and carbimide-6-quinolyl ester by the synthesis method of the compound (4a-1) at a yield of 69.2%.

MS m/z 398.1[M+H].

Example 27: Preparation of 1-(4-((1H-pyrazolopyrimidine-4-yl)oxy)phenyl)-3-pyridylurea (4a-23)

A compound (4a-23) was obtained from the intermediate (3a-1) and carbimide-3-pyridyl ester by the synthesis method of the compound (4a-1) at a yield of 66.2%.

$^1$H NMR (400 MHz, DMSO-$d_6$): δ 14.16 (s, 1H), 9.44 (s, 1H), 9.40 (s, 1H), 8.68 (s, 1H), 8.51 (s, 1H), 8.23 (s, 1H), 8.03-7.96 (m, 2H), 7.57 (d, J=8.0 Hz, 2H), 7.38 (s, 1H), 7.25 (d, J=8.8 Hz, 2H) ppm. LCMS m/z: 348.3 [M+H].

Example 28: Preparation of 1-(4-((1H-pyrazolopyrimidine-4-yl)oxy)phenyl)-3-(3-tert-butyl-1-phenyl-1H-pyrazol-5-yl)urea (4a-24)

A compound (4a-24) was obtained from the intermediate (3a-1) and 1-phenyl-3-tert-butyl-carbimide-5-pyrazol ester by the synthesis method of the compound (4a-1) at a yield of 68.8%.

$^1$H NMR (400 MHz, DMSO-$d_6$): δ 14.13 (s, 1H), 9.16 (s, 1H), 8.50 (s, 1H), 8.45 (s, 1H), 8.03 (s, 1H), 7.55-7.50 (m, 6H), 7.43 (d, J=4.8 Hz 1H), 7.23 (d, J=9.2 Hz, 2H), 6.40 (s, 1H), 1.29 (s, 9H) ppm.

Example 29: Preparation of 1-(4-((1H-pyrazolopyrimidine-4-yl)oxy)phenyl)-3-(3-tert-butylisoxazol-5-yl)urea (4a-25)

A compound (4a-25) was obtained from the intermediate (3a-1) and 3-tert-butyl-isocyanate-5-isoxazole ester by the synthesis method of the compound (4a-1) at a yield of 74.8%.

$^1$H NMR (400 MHz, DMSO-$d_6$): δ 14.14 (s, 1H), 9.56 (s, 1H), 8.94 (s, 1H), 8.51 (s, 1H), 8.06 (s, 1H), 7.56 (d, J=8.8 Hz, 2H), 7.27 (d, J=8.8 Hz, 2H), 6.52 (s, 1H), 1.30 (s, 9H) ppm.

Example 30: Preparation of 1-(4-(1H-pyrazolopyrimidine-4-yl)oxy)phenyl)-3-(5-tert-butylisoxazol-3-yl)urea (4a-26)

A compound (4a-26) was obtained from the intermediate (3a-1) and 5-tert-butyl-isocyanate-3-isoxazole ester by the synthesis method of the compound (4a-1) at a yield of 76.0%.

$^1$H NMR (400 MHz, DMSO-$d_6$): δ 14.15 (s, 1H), 9.57 (s, 1H), 8.95 (s, 1H), 8.51 (s, 1H), 8.06 (s, 1H), 7.56 (d, J=8.8 Hz, 2H), 7.27 (d, J=8.8 Hz, 2H), 6.52 (s, 1H), 1.30 (s, 9H) ppm.

Example 31: Preparation of 1-(4-((1H-pyrazolopyrimidine-4-yl)oxy)phenyl)-3-(3-isopropyl-1-methylpyrazol-5-yl)urea (4a-27)

A compound (4a-27) was obtained from the intermediate (3a-1) and 1-methyl-3-isopropyl-isocyanate-5-pyrazol ester by the synthesis method of the compound (4a-1) at a yield of 68.0%.

$^1$H NMR (400 MHz, DMSO-$d_6$): δ 14.12 (s, 1H), 9.01 (s, 1H), 8.55 (s, 1H), 8.50 (s, 1H), 8.02 (s, 1H), 7.56 (d, J=8.8 Hz, 2H), 7.25 (d, J=8.8 Hz, 2H), 6.02 (s, 1H), 3.61 (s, 3H), 2.71-2.82 (m, 1H), 1.17 (d, J=8.0 Hz, 6H) ppm. LCMS m/z 380.4[M+H].

Example 32: Preparation of 1-(4-((1H-pyrazolopyrimidine-4-yl)oxy)phenyl)-3-(5-trifluoromethyl)isoxazol-3-yl)urea (4a-28)

A compound (4a-28) was obtained from the intermediate (3a-1) and 5-trifluoromethyl-isocyanate-3-isoxazole ester by the synthesis method of the compound (4a-1) at a yield of 66.2%.

LCMS m/z 406.3[M+H].

Example 33: Preparation of 1-(4-((1H-pyrazolopyrimidine-4-yl)oxy)-2-methylphenyl)-3-(5-tert-butyl-isoxazol-3-yl)urea (4a-29)

A compound (4a-29) was obtained from the intermediate (3a-2) and 5-tert-butyl-isocyanate-3-isoxazole ester by the synthesis method of the compound (4a-1) at a yield of 68.4%.

$^1$H NMR (400 MHz, DMSO-$d_6$): δ 14.14 (s, 1H), 9.95 (s, 1H), 8.51 (s, 1H), 8.42 (s, 1H), 8.05 (s, 1H), 7.91 (d, J=8.8 Hz, 1H), 7.20 (d, J=2.4 Hz, 1H), 7.13 (dd, J=2.8 Hz, J=6.0 Hz, 1H), 6.47 (s, 1H), 2.28 (s, 1H), 1.30 (s, 9H) ppm.

Example 34: Preparation of 1-(4-((1H-pyrazolopyrimidine-4-yl)oxy)-2-fluorophenyl)-3-(5-tert-butyl-isoxazol-3-yl)urea (4a-30)

A compound (4a-30) was obtained from the intermediate (3a-3) and 5-tert-butyl-isocyanate-3-isoxazole ester by the synthesis method of the compound (4a-1) at a yield of 71.4%.

$^1$H NMR (400 MHz, DMSO-$d_6$): δ 14.18 (s, 1H), 9.87 (s, 1H), 8.86 (s, 1H), 8.53 (s, 1H), 8.18 (d, J=11.6 Hz, 2H), 7.44 (d, J=10.4 Hz, 1H), 7.17 (d, J=8.4 Hz, 1H), 6.51 (s, 1H) 1.30 (s, 9H) ppm.

Example 35: Preparation of 1-(4-((1H-pyrazolopyrimidine-4-yl)oxy)-3-fluorophenyl)-3-(5-tert-butyl-isoxazol-3-yl)urea (4a-31)

A compound (4a-31) was obtained from the intermediate 4-(pyrazolopyrimidine-4-phenoxyl)-3-fluoroaniline and 5-tert-butyl-isocyanate-3-isoxazole ester by the synthesis method of the compound (4a-1) at a yield of 75.4%.

$^1$H NMR (400 MHz, DMSO-$d_6$): δ 14.27 (s, 1H), 9.63 (s, 1H), 9.13 (s, 1H), 8.51 (s, 1H), 8.29 (s, 1H), 7.67 (d, J=10.4 Hz, 1H), 7.41 (t, J=8.8 Hz, 1H), 7.23 (d, J=8.8 Hz, 1H), 6.50 (s, 1H) 1.30 (s, 9H) ppm.

Example 36: Preparation of 1-(4-((1H-pyrazolopyrimidine-4-yl)oxy)-3-chlorphenyl)-3-(3-tert-butyl-1-methylpyrazol-5-yl)urea (4a-32)

A compound (4a-32) was obtained from the intermediate 4-(pyrazolopyrimidine-4-phenoxyl)-3-chloroaniline and 3-tert-butyl-1-methyl-isocyanate-5-pyrazol ester by the synthesis method of the compound (4a-1) at a yield of 71.4%.

$^1$H NMR (400 MHz, DMSO-$d_6$): δ 14.23 (s, 1H), 9.30 (s, 1H), 8.71 (s, 1H), 8.51 (s, 1H), 8.24 (s, 1H), 7.89 (d, J=1.6 Hz, 1H), 7.44-7.38 (m, 2H), 6.07 (s, 1H), 3.62 (s, 3H), 1.22 (s, 9H) ppm.

LCMS m/z 408.2[M+H].

Example 37: Preparation of 1-(4-((1H-pyrazolopyrimidine-4-yl)oxy)-3,5-difluorophenyl)-3-(5-tert-butylisoxazol-3-yl)urea (4a-33)

A compound (4a-33) was obtained from the intermediate 4-(pyrazolopyrimidine-4-phenoxyl)-3,5-difluoroaniline and 5-tert-butyl-isocyanate-3-isoxazole ester by the synthesis method of the compound (4a-1) at a yield of 68.9%.
LCMS m/z 429.4[M+H].

Example 38: Preparation of 1-(4-((1H-pyrazolopyrimidine-4-yl)oxy)phenyl)-3-(3-tert-butyl-1-methyl-1H-pyrazol-5-yl)urea (4a-34)

A compound (4a-34) was obtained from the intermediate (3a-1) and 3-tert-butyl-1-methyl-isocyanate-5-pyrazol ester by the synthesis method of the compound (4a-1) at a yield of 72.1%.
$^1$H NMR (400 MHz, DMSO-$d_6$): δ 14.13 (s, 1H), 9.19 (s, 1H), 9.03 (br s, 1H), 8.54 (s, 1H), 8.51 (s, 1H), 8.03 (s, 1H), 7.56 (d, J=8.0 Hz, 2H), 7.25 (d, J=8.0 Hz, 2H), 6.06 (s, 1H), 3.62 (s, 3H), 1.22 (s, 9H) ppm.

Example 39: Preparation of 1-(4-((1H-pyrazolopyrimidine-4-yl)oxy)phenyl)-3-(1-methyl-3-(trifluoromethyl)1H-pyrazol-5-yl)urea (4a-35)

A compound (4a-35) was obtained from the intermediate (3a-1) and 3-trifluoromethyl-1-methyl-isocyanate-5-pyrazol ester by the synthesis method of the compound (4a-1) at a yield of 70.1%.
$^1$H NMR (400 MHz, DMSO-$d_6$): δ 14.15 (s, 1H), 9.19 (s, 1H), 9.13 (br s, 1H), 8.51 (s, 1H), 8.06 (s, 1H), 7.57 (d, J=8.8 Hz, 2H), 7.27 (d, J=8.8 Hz, 2H), 6.63 (s, 1H), 3.79 (s, 3H) ppm.

Example 40: Preparation of 1-(4-((1H-pyrazolopyrimidine-4-yl)oxy)-3-fluorophenyl)-3-(1-methyl-3-(trifluoromethyl)1H-pyrazol-5-yl)urea (4a-36)

A compound (4a-36) was obtained from the intermediate 4-(pyrazolopyrimidine-4-phenoxyl)-3-chloroaniline and 3-trifluoromethyl-1-methyl-isocyanate-5-pyrazol ester by the synthesis method of the compound (4a-1) at a yield of 72.4%.
$^1$H NMR (400 MHz, DMSO-$d_6$): δ 14.23 (s, 1H), 9.41 (s, 1H), 9.13 (br s, 1H), 8.53 (s, 1H), 8.33 (s, 1H), 7.69 (d, J=12.8 Hz, 1H), 7.41 (t, J=8.8 Hz, 1H), 7.28 (d, J=8.8 Hz, 1H), 6.64 (s, 1H), 3.79 (s, 3H) ppm.

Example 41: Preparation of 1-(4-((1H-pyrazolopyrimidine-4-yl)oxy)-2-nitrophenyl)-3-(5-tert-butyl-isoxazol-3-yl)urea (4a-37)

A compound (4a-37) was obtained from the intermediate 4-(pyrazolopyrimidine-4-phenoxyl)-2-fluoro-aniline and 5-tert-butyl-isocyanate-3-isoxazole ester by the synthesis method of the compound (4a-1) at a yield of 24.4%.
LCMS m/z 439.4[M+H].

Example 42: Preparation of 1-(4-((1H-pyrazolopyrimidine-4-yl)oxy)-3-fluorophenyl)-3-(3-tert-butyl-isoxazol-5-yl)urea (4a-38)

A compound (4a-38) was obtained from the intermediate 4-(pyrazolopyrimidine-4-phenoxyl)-3-fluoro-aniline and 5-tert-butyl-isocyanate-3-isoxazole ester by the synthesis method of the compound (4a-1) at a yield of 69.1%.
LCMS m/z 412.2[M+H].

Example 43: Preparation of 1-(4-((1H-pyrazolopyrimidine-4-yl)oxy)-2-methoxyphenyl)-3-(5-tert-butylisoxazol-3-yl)urea (4a-39)

A compound (4a-39) was obtained from the intermediate 4-(pyrazolopyrimidine-4-phenoxyl)-2-methoxy-aniline and 3-tert-butyl-isocyanate-5-isoxazole ester by the synthesis method of the compound (4a-1) at a yield of 69.1%.
LCMS m/z 424.2[M+H].

Example 44: Preparation of 1-(4-((1H-pyrazolopyrimidine-4-yl)oxy)phenyl)-3-(3-tert-butyl-1-(quinolin-7-yl)-1H-pyrazol-5-yl)urea (4a-40)

A compound (4a-40) was obtained from the intermediate (3a-1) and 3-tert-butyl-1-(quinolin-7-yl)-isocyanate-5-pyrazol ester by the synthesis method of the compound (4a-1) at a yield of 69.1%.
MS m/z 520.2[M+H].

Example 45: Preparation of 1-(3-((1H-pyrazolopyrimidine-4-yl)oxy)phenyl)-3-(3-trifluoromethyl)phenyl)urea (4a-41)

A compound (4a-41) was obtained from the intermediate 3-(pyrazolopyrimidine-4-phenoxyl)-aniline and 3-trifluoromethyl-phenyl isocyanate by the synthesis method of the compound (4a-1) at a yield of 79.2%.
$^1$H NMR (400 MHz, DMSO-$d_6$): δ 14.18 (s, 1H), 9.20 (s, 1H), 9.05 (s, 1H), 8.54 (s, 1H), 8.11 (s, 1H), 7.6-7.59 (m, 5H), 7.43 (t, J=7.6 Hz, 1H), 7.34 (d, J=8.0 Hz, 2H), 6.97 (d, J=7.2 Hz, 2H) ppm.

Example 46: Preparation of 1-(3-((1H-pyrazolopyrimidine-4-yl)oxy)phenyl)-3-(4-chloro-3-(trifluoromethyl)phenyl)urea (4a-42)

A compound (4a-42) was obtained from the intermediate 3-(pyrazolopyrimidine-4-phenoxyl)-aniline and 4-trifluoromethyl-phenyl isocyanate by the synthesis method of the compound (4a-1) at a yield of 80.1%.
$^1$H NMR (400 MHz, DMSO-$d_6$): δ 14.19 (s, 1H), 9.22 (s, 1H), 9.09 (s, 1H), 8.51 (s, 1H), 8.08 (s, 1H), 7.60-7.56 (m, 3H), 7.42 (t, J=8.0 Hz, 1H), 7.32 (d, J=8.0 Hz, 1H), 6.96 (d, J=7.6 Hz, 1H) ppm.

Example 47: Preparation of 1-(3-((1H-pyrazolopyrimidine-4-yl)oxy)phenyl)-3-(4-trifluoromethyl)phenyl)urea (4a-43)

A compound (4a-43) was obtained from the intermediate 3-(pyrazolopyrimidine-4-phenoxyl)-aniline and 4-trifluoromethyl-phenyl isocyanate by the synthesis method of the compound (4a-1) at a yield of 78.2%.
$^1$H NMR (400 MHz, DMSO-$d_6$): δ 14.16 (s, 1H), 9.17 (s, 1H), 9.03 (s, 1H), 8.53 (s, 1H), 8.10 (s, 1H), 7.66-7.57 (m, 5H), 7.42 (t, J=8.0 Hz, 1H), 7.33 (d, J=8.8 Hz, 1H), 6.97 (d, J=7.2 Hz, 1H) ppm.

Example 48: Preparation of 1-(3-((1H-pyrazolopyrimidine-4-yl)oxy)phenyl)-3-(5-tert-butylisoxazol-3-yl)urea (4a-44)

A compound (4a-44) was obtained from the intermediate 3-(pyrazolopyrimidine-4-phenoxyl)-aniline and 5-tert-butyl-isocyanate-3-isoxazole ester by the synthesis method of the compound (4a-1) at a yield of 81.6%.

$^1$H NMR (400 MHz, DMSO-d$_6$): δ 14.17 (s, 1H), 9.58 (s, 1H), 8.01 (s, 1H), 8.52 (s, 1H), 8.10 (s, 1H), 7.58 (s, 1H), 7.42 (t, J=8.4 Hz, 1H), 6.99 (d, J=7.6 Hz, 1H), 6.48 (s, 1H), 1.28 (s, 9H) ppm.

Example 49: Preparation of 1-(4-((1H-pyrazolopyrimidine-4-yl)oxy)-3-fluorophenyl)-3-(3-tert-butyl-1-methylpyrazol-5-yl)urea (4a-45)

A compound (4a-45) was obtained from the intermediate 4-(pyrazolopyrimidine-4-phenoxyl)-3-fluoroaniline and 3-tert-butyl-1-methyl-isocyanate-5-pyrazol ester by the synthesis method of the compound (4a-1) at a yield of 70.4%.

$^1$H NMR (400 MHz, DMSO-d$_6$): δ 14.24 (s, 1H), 9.21 (s, 1H), 8.61 (s, 1H), 8.52 (s, 1H), 8.31 (s, 1H), 7.69 (d, J=1.2 Hz, 1H), 7.41-7.37 (m, 1H), 7.26-7.22 (m, 1H), 6.07 (s, 1H), 3.62 (s, 3H), 1.22 (s, 9H) ppm.

Example 50: Preparation of 1-(4-((1H-pyrazolopyrimidine-4-yl)oxy)-3-chlorphenyl)-3-(5-tert-butyl-isoxazol-3-yl)urea (4a-46)

A compound (4a-46) was obtained from the intermediate 4-(pyrazolopyrimidine-4-phenoxyl)-3-chloroaniline and 5-tert-butyl-isocyanate-3-isoxazole ester by the synthesis method of the compound (4a-1) at a yield of 78.4%.

$^1$H NMR (400 MHz, DMSO-d$_6$): δ 14.25 (s, 1H), 9.68 (s, 1H), 9.10 (s, 1H), 8.52 (s, 1H), 8.26 (s, 1H), 7.89 (d, J=4.0 Hz, 1H), 7.49-7.41 (m, 2H), 6.53 (s, 1H) 1.30 (s, 9H) ppm.

Example 51: Preparation of N-(4-((1H-pyrazolopyrimidine-4-yl)oxy)phenyl)-4-bromobenzamide (4a-47)

4-bromobenzoic acid (265 mg, 1.32 mmol), 1-hydroxybenzotriazole (HOBT, 178.8 mg, 1.32 mmol), 1-(3-dimethylaminopropyl)-3-ethyl carbodiimide hydrochloride (EDCI, 254.6 mg, 1.32 mmol) and N,N-diisopropylethylamine (DIEA, 0.33 mL, 2.0 mmol) were added to 25 mL tetrahydrofuran and stirred at normal temperature for 30-minute reaction, the compound (3a-1) (300 mg, 1.32 mmol) was added to increase the temperature to 60° C. to react overnight. After reaction and cooling, 5 mL ice water was added to separate out a large amount of solids, solids were subject to extracted and washed to obtain 390 mg compound (4a-47) at a yield of 72.1%.

$^1$H NMR (400 MHz, DMSO-d$_6$): δ 14.18 (s, 1H), 10.49 (s, 1H), 8.53 (s, 1H), 8.11 (br s, 1H), 7.95 (d, J=8.4 Hz, 2H), 7.88 (d, J=8.8 Hz, 2H), 7.79 (d, J=8.4 Hz, 2H), 7.34 (d, J=9.2 Hz, 2H) ppm.

Example 52: Preparation of N-(3-((1H-pyrazolopyrimidine-4-yl)oxy)phenyl)-4-bromobenzamide (4a-48)

A compound (4a-48) was obtained from the intermediate 3-(pyrazolopyrimidine-4-phenoxyl)-aniline and 4-bromobenzoic acid by the synthesis method of the compound (4a-47) at a yield of 76.6%.

$^1$H NMR (400 MHz, DMSO-d$_6$): δ 14.19 (s, 1H), 10.51 (s, 1H), 8.53 (s, 1H), 8.16 (s, 1H), 7.91 (d, J=8.4 Hz, 2H), 7.83 (s, 1H), 7.76 (d, J=8.4 Hz, 2H), 7.71 (d, J=8.0 Hz, 1H), 7.49 (t, J=8.0 Hz, 1H), 7.09 (dd, J=1.6 Hz, 6.4 Hz, 1H) ppm. LCMS m/z: 410.0 [M+H].

Example 53: Preparation of N-(3-((1H-pyrazolopyrimidine-4-yl)oxy)phenyl)-4-fluorobenzamide (4a-49)

A compound (4a-49) was obtained from the intermediate 3-(pyrazolopyrimidine-4-phenoxyl)-aniline and 3-fluorobenzoic acid by the synthesis method of the compound (4a-47) at a yield of 76.0%.

$^1$H NMR (400 MHz, DMSO-d$_6$): δ 14.18 (s, 1H), 10.50 (s, 1H), 8.53 (s, 1H), 8.15 (s, 1H), 7.84-7.70 (m, 4H), 7.62 (d, J=6.0 Hz, 1H), 7.59 (t, J=4.0 Hz, 1H), 7.57-7.46 (m, 1H), 7.09 (d, J=2.0 Hz, 1H) ppm. LCMS m/z: 350.1 [M+H].

Example 54: Preparation of N-(3-((1H-pyrazolopyrimidine-4-yl)oxy)phenyl)-4-(trifluoromethyl)benzamide (4a-50)

A compound (4a-50) was obtained from the intermediate 3-(pyrazolopyrimidine-4-phenoxyl)-aniline and 4-(trifluoromethyl)benzoic acid by the synthesis method of the compound (4a-47) at a yield of 71.2%.

$^1$H NMR (400 MHz, DMSO-d$_6$): δ 14.18 (s, 1H), 10.66 (s, 1H), 8.53 (s, 1H), 8.15 (d, J=8.4 Hz, 3H), 7.93 (d, J=8.4 Hz, 2H), 7.84 (s, 1H), 7.72 (d, J=8.8 Hz, 1H), 7.50 (t, J=8.0 Hz, 1H), 7.12 (dd, J=2.0 Hz, J=6.4 Hz, 1H) ppm. LCMS m/z: 400.3 [M+H].

Example 55: Preparation of N-(3-((1H-pyrazolopyrimidine-4-yl)oxy)phenyl)-2-(4-chlorophenyl)acetamide (4a-51)

A compound (4a-51) was obtained from the intermediate 3-(pyrazolopyrimidine-4-phenoxyl)-aniline and 4-chlorophenylacetic acid by the synthesis method of the compound (4a-47) at a yield of 67.8%.

$^1$H NMR (400 MHz, DMSO-d$_6$): δ 14.17 (s, 1H), 10.47 (s, 1H), 8.50 (s, 1H), 8.12 (s, 1H), 7.68-7.34 (m, 8H), 7.00 (d, J=1.2 Hz, 1H), 3.67 (s, 1H) ppm. LCMS m/z: 380.1 [M+H].

Example 56: Preparation of 1-(4-((1H-pyrazolopyrimidine-4-yl)oxy)phenyl)-3-phenylthiourea (4a-52)

A compound (4a-52) was obtained from the intermediate (3a-1) and phenyl isothiocyanate by the synthesis method of the compound (4a-1) at a yield of 82.0%.

$^1$H NMR (400 MHz, DMSO-d$_6$): δ 14.13 (s, 1H), 8.80 (s, 1H), 8.72 (s, 1H), 8.51 (s, 1H), 8.03 (s, 2H), 7.56 (d, J=8.8 Hz, 2H), 7.47 (d, J=8.8 Hz, 2H), 7.31-7.24 (m, 4H), 6.98 (t, J=8.0 Hz, 1H) ppm. LCMS m/z: 365.1 [M+H].

Example 57: Preparation of 1-(4-((1H-pyrazolopyrimidine-4-yl)oxy)phenyl)-3-(3-trifluoromethylphenyl)thiourea (4a-53)

A compound (4a-53) was obtained from the intermediate (3a-1) and 3-trifluoromethyl-phenyl isothiocyanate by the synthesis method of the compound (4a-1) at a yield of 79.8%.

LCMS m/z 431.02[M+H].

Example 58: Preparation of 1-(4-((1H-pyrazolopyrimidine-4-yl)oxy)-2-fluorophenyl)-3-(4-chloro-3-(trifluoromethyl)phenyl)urea (4a-54)

A compound (4a-54) was obtained from the intermediate 4-(pyrazolopyrimidine-4-phenoxyl)-2-fluoroaniline and 4-chloro-3-trifluoromethyl phenyl isocyanate by the synthesis method of the compound (4a-1) at a yield of 66%.
¹H NMR (400 MHz, DMSO-$d_6$): δ 14.19 (s, 1H), 9.55 (s, 1H), 8.74 (s, 1H), 8.53 (s, 1H), 8.21 (s, 1H), 8.13 (d, J=2.4 Hz, 2H), 7.64 (s, 2H), 7.43 (d, J=11.6 Hz, 1H), 7.17 (d, J=8.8 Hz, 1H). LCMS m/z 467.1[M+H].

Example 59: Preparation of 1-(4-((1H-pyrazolopyrimidine-4-yl)oxy)phenyl)-2-chlorophenyl)-3-(4-chloro-3-(trifluoromethyl)phenyl)urea (4a-55)

A compound (4a-55) was obtained from the intermediate 4-(pyrazolopyrimidine-4-phenoxyl)-2-chloroaniline and 4-chloro-3-trifluoromethyl phenyl isocyanate by the synthesis method of the compound (4a-1) at a yield of 68%.
¹H NMR (400 MHz, DMSO-$d_6$): δ 14.20 (s, 1H), 9.56 (s, 1H), 8.70 (s, 1H), 8.54 (s, 1H), 8.21 (s, 1H), 8.13 (d, J=4.8 Hz, 2H), 7.68 (s, 2H), 7.43 (d, J=11.6 Hz, 1H), 7.15 (d, J=8.8 Hz, 1H). LCMS m/z 483.0[M+H].

Example 60: Preparation of 1-(4-((1H-pyrazolopyrimidine-4-yl)oxy)-3-fluorophenyl)-3-(3-tert-butyl-1-phenyl-1H-pyrazol-5-yl)urea (4a-56)

A compound (4a-56) was obtained from the intermediate 4-(pyrazolopyrimidine-4-phenoxyl)-3-fluoroaniline and 1-phenyl-3-tert-butyl-isocyanate-5-pyrazol ester by the synthesis method of the compound (4a-1) at a yield of 86%.
¹H NMR (400 MHz, DMSO-$d_6$): δ 14.23 (s, 1H), 9.33 (s, 1H), 8.53 (s, 1H), 8.50 (s, 1H), 8.30 (s, 1H), 7.66 (d, J=2.4 Hz, 1H), 7.55 (d, J=4.4 Hz 4H), 7.43-7.39 (m, 2H), 7.21 (d, J=2.4 Hz, 1H), 6.40 (s, 1H), 1.29 (s, 9H) ppm. LCMS m/z 487.1[M+H].

Example 61: Preparation of 1-(4-((1H-pyrazolopyrimidine-4-yl)oxy)-3-chlorophenyl)-3-(3-tert-butyl-1-phenyl-1H-pyrazol-5-yl)urea (4a-57)

A compound (4a-57) was obtained from the intermediate 4-(pyrazolopyrimidine-4-phenoxyl)-3-chloroaniline and 1-phenyl-3-tert-butyl-isocyanate-5-pyrazol ester by the synthesis method of the compound (4a-1) at a yield of 87%.
¹H NMR (400 MHz, DMSO-$d_6$): δ 14.22 (s, 1H), 9.31 (s, 1H), 8.53 (s, 1H), 8.50 (s, 1H), 8.23 (s, 1H), 7.85 (d, J=2.0 Hz, 1H), 7.55 (d, J=4.4 Hz 4H), 7.43-7.39 (m, 2H), 7.34 (d, J=2.0 Hz, 1H), 6.40 (s, 1H), 1.29 (s, 9H) ppm.
¹³C NMR (100 MHz, DMSO-$d_6$): δ 170.3, 162.2, 160.8, 156.8, 154.8, 151.7, 142.1, 138.6, 136.8, 131.7, 129.3, 127.2, 126.0, 124.5, 124.2, 119.2, 118.1, 101.0, 96.1, 32.0, 30.1 ppm. LCMS m/z 503.1[M+H].

Example 62: Preparation of 5-(3-(4-((1H-pyrazolopyrimidine-4-yl)oxy)phenyl)carbamido)-3-tert-butyl-1H-pyrazol-1-carboxylic acid) (4a-58)

A compound (4a-58) was obtained from the intermediate (3a-1) and 1-Boc-3-tert-butyl-isocyanate-5-pyrazol ester by the synthesis method of the compound (4a-1) at a yield of 86%.
¹H NMR (400 MHz, DMSO-$d_6$): δ 14.12 (s, 1H), 11.99 (s, 1H), 9.31 (s, 1H), 8.93 (s, 1H), 8.51 (s, 1H), 8.02 (s, 1H), 7.54 (d, J=8.4 Hz, 2H), 7.24 (d, J=8.4 Hz, 2H), 6.00 (s, 1H), 1.26 (s, 9H) ppm. LCMS m/z 435.1 [M−H].

Example 63: Preparation of 5-(3-(4-((1H-pyrazolopyrimidine-4-yl)oxy)-3-fluoro-phenyl)carbamido)-3-tert-butyl-1H-pyrazol-1-carboxylic acid) (4a-59)

A compound (4a-59) was obtained from the intermediate 4-(pyrazolopyrimidine-4-phenoxyl)-3-fluoroaniline and 1-Boc-3-tert-butyl-isocyanate-5-pyrazol ester by the synthesis method of the compound (4a-1) at a yield of 84%.
¹H NMR (400 MHz, DMSO-$d_6$): δ 14.12 (s, 1H), 11.99 (s, 1H), 9.31 (s, 1H), 8.93 (s, 1H), 8.51 (s, 1H), 8.02 (s, 1H), 7.65 (dd, J=2.4 Hz, J=10.8 Hz, 1H), 7.40 (t, J=8.8 Hz, 1H), 7.22 (d, J=8.8 Hz, 1H), 6.00 (s, 1H), 1.26 (s, 9H) ppm. LCMS m/z 453.1 [M−H].

Example 64: Preparation of 5-(3-(4-((1H-pyrazolopyrimidine-4-yl)oxy)-3-fluoro-phenyl)carbamido)-3-tert-butyl-1H-pyrazol-1-carboxylic acid) (4a-60)

A compound (yll728) was obtained from the intermediate 4-(pyrazolopyrimidine-4-phenoxyl)-3-fluoroaniline and 1-(4-fluorophenyl)-3-tert-butyl-isocyanate-5-pyrazol ester by the synthesis method of the compound (4a-1) at a yield of 79%.
¹H NMR (400 MHz, DMSO-$d_6$): δ 14.23 (s, 1H), 9.29 (s, 1H), 8.51 (s, 1H), 8.49 (s, 1H), 8.30 (s, 1H), 7.65-7.56 (m, 3H), 7.38 (t, J=8.8 Hz, 3H), 7.18 (d, J=8.8 Hz, 1H), 6.38 (s, 1H), 1.29 (s, 9H) ppm. LCMS m/z 505.2[M+H].

Example 65: Preparation of 1-(4-((1H-pyrazolopyrimidine-4-yl)oxy)phenyl)-3-(3-tert-butyl-1-cyclopentyl-1H-pyrazol-5-yl)urea (4a-61)

A compound (4a-61) was obtained from the intermediate (3a-1) and 1-cyclopentyl-3-tert-butyl-isocyanate-5-pyrazol ester by the synthesis method of the compound (4a-1) at a yield of 92%.
¹H NMR (400 MHz, DMSO-$d_6$): δ 14.15 (s, 1H), 9.38 (s, 1H), 8.79 (s, 1H), 8.51 (s, 1H), 8.03 (s, 1H), 7.56 (d, J=8.0 Hz, 2H), 7.24 (d, J=8.0 Hz, 2H), 6.05 (s, 1H), 4.63-4.55 (m, 1H), 1.99-1.92 (m, 4H), 1.84-1.81 (m, 2H), 1.60-1.56 (m, 2H), 1.22 (s, 9H) ppm. LCMS m/z 461.2[M+H].

Example 66: Preparation of 1-(4-((1H-pyrazolopyrimidine-4-yl)oxy)-3-fluorophenyl)-3-(3-tert-butyl-1-cyclopentyl-1H-pyrazol-5-yl)urea (4a-62)

A compound (4a-62) was obtained from the intermediate 4-(pyrazolopyrimidine-4-phenoxyl)-3-fluoroaniline and 1-cyclopentyl-3-tert-butyl-isocyanate-5-pyrazol ester by the synthesis method of the compound (4a-1) at a yield of 94%.
¹H NMR (400 MHz, DMSO-$d_6$): δ 14.23 (s, 1H), 9.17 (s, 1H), 8.52 (s, 1H), 8.49 (s, 1H), 8.30 (s, 1H), 7.68 (dd, J=2.4 Hz, J=10.8 Hz, 1H), 7.40 (t, J=8.8 Hz, 1H), 7.24 (d, J=8.8 Hz, 1H), 6.05 (s, 1H), 4.55-4.48 (m, 1H), 1.98-1.89 (m, 4H), 1.88-1.80 (m, 2H), 1.62-1.56 (m, 2H), 1.22 (s, 9H) ppm.
¹³C NMR (100 MHz, DMSO-$d_6$): δ 162.1, 158.4, 156.7, 154.8, 152.3, 152.1, 138.9, 135.8, 132.9, 131.7, 124.2, 114.4, 106.4, 100.9, 94.7, 57.00, 31.8, 30.3, 23.9 ppm. LCMS m/z 479.2[M+H].

Example 67: Preparation of 1-(4-((1H-pyrazolopyrimidine-4-yl)oxy)phenyl)-3-(3-tert-butyl-thiazol-2-yl)urea (4a-63)

A compound (4a-63) was obtained from the intermediate (3a-1) and 4-tert-butyl-2-isocyanate thiazole ester by the synthesis method of the compound (4a-1) at a yield of 76%.
¹H NMR (400 MHz, DMSO-$d_6$): δ 14.06 (s, 1H), 10.60 (s, 1H), 8.99 (s, 1H), 8.51 (s, 1H), 8.07 (s, 1H), 7.57 (d, J=8.8 Hz, 2H), 7.28 (d, J=8.8 Hz, 2H), 6.65 (s, 1H), 1.26 (s, 9H) ppm. LCMS m/z 410.1[M+H].

Example 68: Preparation of 1-(4-((1H-pyrazolopyrimidine-4-yl)oxy)phenyl)-3-(4-phenylthiazol-2-yl) urea (4a-64)

A compound (4a-64) was obtained from the intermediate (3a-1) and 4-phenyl-2-isocyanate thiazole ester by the synthesis method of the compound (4a-1) at a yield of 71%.

$^1$H NMR (400 MHz, DMSO-d$_6$): δ 14.14 (s, 1H), 10.76 (s, 1H), 9.06 (s, 1H), 8.51 (s, 1H), 8.06 (s, 1H), 7.90 (d, J=8.8 Hz, 2H), 7.60 (d, J=8.8 Hz, 2H), 7.56 (s, 1H), 7.43 (t, J=8.0 Hz, 2H), 7.34-7.29 (m, 3H) ppm. LCMS m/z 430.1[M+H].

Example 69: Preparation of 1-(4-((1H-pyrazolopyrimidine-4-yl)oxy)phenyl)-3-(benzothiazol-2-yl)urea (4a-65)

A compound (4a-65) was obtained from the intermediate (3a-1) and 2-phenyl isocyanate benzothiazole ester by the synthesis method of the compound (4a-1) at a yield of 69%.

$^1$H NMR (400 MHz, DMSO-d$_6$): δ 14.14 (s, 1H), 10.85 (s, 1H), 9.33 (s, 1H), 8.52 (s, 1H), 8.07 (s, 1H), 7.91 (d, J=7.2 Hz, 1H), 7.64 (d, J=8.4 Hz, 3H), 7.40 (t, J=7.6 Hz, 1H), 7.30 (d, J=8.8 Hz, 2H), 7.25 (t, J=8.0 Hz, 1H) ppm. LCMS m/z 404.1[M+H].

Example 70: Preparation of 1-(3-(1H-pyrazolopyrimidine-4-amido)phenyl)-3-(3-chloro-4-(fluorophenyl)urea (4b-1)

After 60 mL n-butyl alcohol was added to 1-(3-aminophenyl)-3-(3-chloro-4-(fluorophenyl)urea (1.4 g), catalytic amount of hydrochloric acids was added and stirred at normal temperature for 20 minutes; 780 mg 4-chloro-1H-pyrazolopyrimidine (intermediate 2) was added; the temperature was increased to 100° C. for reacting for 2.5 hours, after which, solvents were spun dry; after potassium carbonate was added for proper adjustment of pH value, ethyl acetate was used to extract twice; after the ethyl acetate layer was spun dry and stirred, the reaction product was introduced into a column for purification with dichloromethane and methanol at a ratio of 24:1, thus obtaining 1.71 g solid at a yield of 86.6%.

$^1$H NMR (400 MHz, DMSO-d$_6$): δ 13.65 (s, 1H), 10.02 (s, 1H), 8.88 (d, J=11.2 Hz, 1H), 8.40 (s, 1H), 8.31 (s, 2H), 8.03 (m, 6H), 7.83 (t, J=6.4 Hz, 1H), 7.57 (d, J=7.6 Hz, 1H), 7.37-7.27 (m, 3H), 7.19 (d, J=7.6 Hz, 1H) ppm.

Example 71: Preparation of (R)-1-(4-(1H-pyrazolopyrimidine-4-amido)phenyl)-3-(1-phenethyl)urea (4b-2)

A compound (4b-2) was obtained from the intermediate (2) and (R)-1-(4-amido-phenyl)-3-(1-phenethyl)urea by the synthesis method of the compound (4b-1) at a yield of 87.9%.

$^1$H NMR (400 MHz, DMSO-d$_6$): δ 13.56 (s, 1H), 9.86 (s, 1H), 8.41 (s, 1H), 8.32 (s, 1H), 8.01 (s, 1H), 7.61 (s, 2H), 7.40-7.34 (m, 6H), 7.26-7.23 (m, 1H), 6.62 (d, J=8.0 Hz, 1H), 4.84-4.81 (m, 1H), 1.39 (d, J=6.8 Hz, 3H) ppm.

Example 72: Preparation of 1-(4-(1H-pyrazolopyrimidine-4-amido)-3-(3-methoxyphenyl)urea (4b-3)

A compound (4b-3) was obtained from the intermediate (2) and 1-(4-amido-phenyl)-3-(3-methoxyphenyl)urea by the synthesis method of the compound (4b-1) at a yield of 87.6%.

$^1$H NMR (400 MHz, DMSO-d$_6$): δ 13.59 (s, 1H), 9.93 (s, 1H), 8.69 (d, J=5.6 Hz, 2H), 8.35 (s, 1H), 8.15 (s, 1H), 7.71 (d, J=8.0 Hz, 2H), 7.47 (d, J=8.8 Hz, 2H), 7.21-7.16 (m, 2H), 6.93 (d, J=8.0 Hz, 1H), 6.56-6.53 (m, 1H), 3.74 (s, 3H) ppm.

Example 73: Preparation of (S)-1-(4-(1H-pyrazolopyrimidine-4-amido)phenyl)-3-(1-phenethyl)urea (4b-4)

A compound (4b-4) was obtained from the intermediate (2) and (S)-1-(4-amido-phenyl)-3-(1-phenethyl)urea by the synthesis method of the compound (4b-1) at a yield of 85.6%.

$^1$H NMR (400 MHz, DMSO-d$_6$): δ 13.55 (s, 1H), 9.85 (s, 1H), 8.40 (s, 1H), 8.32 (s, 1H), 8.01 (s, 1H), 7.61 (s, 2H), 7.40-7.34 (m, 6H), 7.26-7.22 (m, 1H), 6.61 (d, J=8.0 Hz, 1H), 4.84-4.81 (m, 1H), 1.39 (d, J=6.8 Hz, 3H) ppm.

Example 74: Preparation of 1-(4-(1H-pyrazolopyrimidine-4-amido)phenyl)-3-(4-chloro-3-(trifluoromethyl)phenyl)urea (4b-5)

A compound (4b-5) was obtained from the intermediate (2) and 1-(4-amido-phenyl)-3-(4-chloro-3-trifluoromethylphenyl)urea by the synthesis method of the compound (4b-1) at a yield of 88.6%.

$^1$H NMR (400 MHz, DMSO-d$_6$): δ 13.60 (s, 1H), 9.95 (s, 1H), 9.17 (s, 1H) H), 8.86 (s, 1H), 8.36 (s, 1H), 8.15 (b, 1H), 8.14 (s, 1H), 7.75 (d, J=8.4 Hz, 2H), 7.67-7.61 (m, 2H), 7.49 (d, J=8.8 Hz, 2H) ppm.

Example 75: Preparation of 1-(4-(1H-pyrazolopyrimidine-4-amido)phenyl)-3-(4-methoxyphenyl)urea (4b-6)

A compound (4b-6) was obtained from the intermediate (2) and 1-(4-amido-phenyl)-3-(4-methoxyphenyl)urea by the synthesis method of the compound (4b-1) at a yield of 88.0%.

$^1$H NMR (400 MHz, DMSO-d$_6$): δ 13.57 (s, 1H), 9.90 (s, 1H), 8.58 (s, 1H), 8.46 (s, 1H), 8.34 (s, 1H), 8.15 (b, 1H), 7.68 (s, 2H), 7.45 (d, J=8.0 Hz, 2H), 7.35 (d, J=8.0 Hz, 2H), 6.86 (d, J=8.4 Hz, 2H), 3.71 (s, 3H) ppm.

Example 76: Preparation of 1-(4-(1H-pyrazolopyrimidine-4-amido)phenyl)-3-(2,4,6-trimethylphenyl) urea (4b-7)

A compound (4b-7) was obtained from the intermediate (2) and 1-(4-amido-phenyl)-3-(2,4,6-trimethylphenyl)urea by the synthesis method of the compound (4b-1) at a yield of 87.2%.

$^1$H NMR (400 MHz, DMSO-d$_6$): δ 13.62 (s, 1H), 10.14 (s, 1H), 8.86 (s, 1H), 8.37 (s, 2H), 8.34 (s, 1H), 8.11 (b, 1H), 7.67-7.62 (m, 3H), 7.46 (d, J=8.0 Hz, 2H), 6.89 (s, 2H), 2.23 (s, 3H), 2.18 (s, 6H) ppm.

Example 77: Preparation of 1-(4-(1H-pyrazolopyrimidine-4-amido)phenyl)-3-(5-tert-butylisoxazol-3-yl)urea (4b-8)

A compound (4b-8) was obtained from the intermediate N$^1$-(pyrazolopyrimidine-4-yl)phenyl-1,4-diamine and 3-tert-butyl-isocyanate-5-isoxazole ester by the synthesis method of the compound (4b-1) at a yield of 52.7%.

¹H NMR (400 MHz, DMSO-d₆): δ 13.57 (s, 1H), 10.04 (s, 1H), 9.74 (s, 1H), 8.42 (s, 1H), 8.24 (s, 1H), 8.14 (s, 1H), 7.32 (d, J=6.8 Hz, 2H), 7.12 (t, J=7.6 Hz, 1H), 6.45 (s, 1H), 1.26 (s, 9H) ppm.

Example 78: Preparation of 1-(4-(1H-pyrazolopyrimidine-4-sulfydryl)phenyl)-3-(4-trifluoromethyl)phenyl)urea (4c-1)

A compound (4c-1) was obtained from the intermediate (3c-1) and p-trifluoromethyl phenyl isocyanate by the synthesis method of the compound (4a-1) at a yield of 46.6%.
LCMS m/z 431.0[M+H].

Example 79: Preparation of 1-(4-(1H-pyrazolopyrimidine-4-sulfydryl)phenyl)-3-(3-trifluoromethyl)phenyl)urea (4c-2)

A compound (4c-2) was obtained from the intermediate (3c-1) and 2-(trifluoromethyl)phenyl isocyanate by the synthesis method of the compound (4a-1) at a yield of 42.3%.
¹H NMR (400 MHz, DMSO-d₆): δ 14.09 (s, 1H), 9.22 (s, 2H), 8.64 (s, 1H), 8.04 (s, 2H), 7.62-7.54 (m, 4H), 7.36 (d, J=7.2 Hz, 1H), 7.27 (d, J=8.4 Hz, 2H) ppm.
LCMS m/z 431.0[M+H].

Example 80: Preparation of 1-(4-(1H-pyrazolopyrimidine-4-sulfydryl)phenyl)-3-(5-tert-butylisoxazol-3-yl)urea (4c-3)

A compound (4c-3) was obtained from the intermediate (3c-1) and 5-tert-butyl-isocyanate-3-isoxazole ester by the synthesis method of the compound (4a-1) at a yield of 42.6%.
LCMS m/z 410.2[M+H].

Example 81: Preparation of 1-(4-(1 methyl-(1H-pyrazolopyrimidine-4-yl)oxyl)phenyl)-3-(4-(trifluoromethyl)phenyl)urea (5a-1)

Up to 70 mg potassium hydroxide (1.21 mmol) was added to DMF (20 mL) solution of 500 mg (1.21 mmol) compound (4a-1), stirred at normal temperature for 30 minutes, and then methyl iodide (0.07 mL, 1.21 mmol) was added and stirred overnight at normal temperature; upon reaction, water and ethyl acetate were used to extract for 3 times, and the ethyl acetate layer was spun dry and introduced into a column for purification to obtain 320 mg product at a yield of 71.4%.
¹H NMR (400 MHz, DMSO-d₆): δ 9.17 (s, 1H), 8.96 (s, 1H), 8.55 (s, 1H), 8.07 (s, 2H), 7.70-7.64 (m, 4H), 7.57 (d, 1H), 7.67-7.62 (m, J=8.4 Hz, 2H), 7.26 (d, J=8.8 Hz, 2H) 4.05 (s, 3H) ppm.

Example 82: Preparation of 1-(4-(1-methyl-(1H-pyrazolopyrimidine-4-yl)oxyl)phenyl)-3-(3-methoxyphenyl)urea (5a-2)

A compound (5a-2) was obtained from the compound (4a-5) and methyl iodide by the synthesis method of the compound (5a-1) at a yield of 78.6%.
¹H NMR (400 MHz, DMSO-d₆): δ 8.82 (s, 1H), 8.75 (s, 1H), 8.55 (s, 1H), 8.05 (s, 1H), 7.55 (d, J=8.8 Hz, 2H), 7.26-7.17 (m, 4H), 6.95 (d, J=8.4 Hz, 1H), 6.57 (d, J=8.4 Hz, 1H) ppm.
LCMS m/z: 391.4 [M+H].

Example 83: Preparation of 1-(5-tert-butylisoxazol-3-yl)-3-(4-(1-methyl-(1H-pyrazolopyrimidine-4-yl)oxy)phenyl)urea (5a-3)

A compound (5a-3) was obtained from the compound (4a-26) and methyl iodide by the synthesis method of the compound (5a-1) at a yield of 76.0%.
¹H NMR (400 MHz, DMSO-d₆): δ 9.57 (s, 1H), 8.95 (s, 1H), 8.55 (s, 1H), 8.08 (s, 1H), 7.56 (d, J=9.2 Hz, 2H), 7.27 (d, J=8.8 Hz, 2H), 6.52 (s, 1H), 4.05 (s, 3H), 1.30 (s, 9H) ppm.

Example 84: Preparation of 1-(5-tert-butylisoxazol-3-yl)-3-(4-(1-isopropyl-(1H-pyrazolopyrimidine-4-yl)oxy)phenyl)urea (5a-4)

A compound (5a-4) was obtained from the compound (4a-26) and 2-bromopropane by the synthesis method of the compound (5a-1) at a yield of 69.0%.
LCMS m/z: 436.2 [M+H].

Example 85: Preparation of 1-(5-tert-butylisoxazol-3-yl)-3-(4-(1-(2-morpholinoethyl)-(1H-pyrazolopyrimidine-4-yl)oxy)phenyl)urea (5a-5)

Potassium hydroxide (70 mg, 1.21 mmol) was added to DMF (20 mL) solution of 275 mg (1.21 mmol) compound (3a-1) and stirred at normal temperature for 30 minutes, and then 4-(2-chloroethyl)morpholine hydrochloride (224 mg, 1.21 mmol) was added for reaction for 6 hours at 80° C., then the reaction solution was extracted with a large amount of water and ethyl acetate; upon reaction, the reaction solution was extracted with water and ethyl acetates for 3 times, and the ethyl acetate layer was spun dry and introduced into a column for purification to obtain 280 mg 4-(1-(2-morpholinoethyl)-pyrazolopyrimidine-4-phenoxy) aniline at a yield of 68.1%.
A compound (5a-5) was obtained from the intermediate 4-(1-(2-(morpholineethyl)-pyrazolopyrimidine-4-phenoxyl) aniline and 3-tert-butyl-isocyanate-5-isoxazole ester by the synthesis method of the compound (4a-1) at a yield of 72.1%.
¹H NMR (400 MHz, DMSO-d₆): δ 9.60 (s, 1H), 9.06 (s, 1H), 8.54 (s, 1H), 8.11 (s, 1H), 7.56 (d, J=8.4 Hz, 2H), 7.27 (d, J=8.4 Hz, 2H), 6.52 (s, 1H), 4.56 (br s, 1H), 3.46 (s, 4H), 2.80 (s, 2H), 2.43 (s, 4H), 1.30 (s, 9H) ppm.

Example 86: Preparation of 1-(5-tert-butylisoxazol-3-yl)-3-(4-(1-(3-dimethylaminopropyl)-(1H-pyrazolopyrimidine-4-yloxy)phenyl)urea (5a-6)

A compound (5a-6) was obtained from the intermediate (3a-1) and 3-chloro-N,N-dimethylpropyl-1-amine by the synthesis method of the compound (5a-5) at a yield of 49.1%.
¹H NMR (400 MHz, DMSO-d₆): δ 9.77 (s, 1H), 9.59 (s, 1H), 8.57 (s, 1H), 8.11 (s, 1H), 7.58 (d, J=9.2 Hz, 2H), 7.26 (d, J=8.8 Hz, 2H), 6.52 (s, 1H), 4.52 (t, J=6.4 Hz, 2H), 2.98 (t, J=7.6 Hz, 2H), 2.64 (s, 6H), 2.24 (t, J=7.6 Hz, 2H), 1.30 (s, 9H) ppm.

Example 87: Preparation of 1-(5-tert-butyl-1H-pyrazol-3-yl)-3-(4-(1-isopropyl-(1H-pyrazolopyrimidine-4-yl)oxy)phenyl)urea (5a-7)

A compound (5a-7) was obtained from the intermediate (3a-1) and 3-bromopropane and 5-tert-butyl-3-aminopyrazole by the synthesis method of the compound (5a-5) at a yield of 54.2%.

¹H NMR (400 MHz, DMSO-d₆): δ 12.00 (s, 1H), 9.31 (br s, 1H), 8.95 (s, 1H), 8.53 (s, 1H), 8.03 (s, 1H), 7.55 (d, J=8.8 Hz, 2H), 7.24 (d, J=8.8 Hz, 2H), 6.00 (s, 1H), 5.17-5.11 (m, 1H), 1.50 (d, J=6.0 Hz 6H), 1.26 (s, 9H) ppm.
LCMS m/z: 435.2 [M+H].

Example 88: Preparation of 1-(5-tert-butylisoxazol-3-yl)-3-(4-(1-(2-morpholinoethyl)-(1H-pyrazolopyrimidine-4-yl)oxy)phenyl)urea (5a-8)

A compound (5a-8) was obtained from the intermediate (3a-1) and 4-(2-chloroethyl)morpholine hydrochloride and 5-tert-butyl-3-aminopyrazole by the synthesis method of the compound (5a-5) at a yield of 51.0%.
$^1$H NMR (400 MHz, DMSO-d₆): δ 11.99 (s, 1H), 9.30 (br s, 1H), 8.94 (s, 1H), 8.54 (s, 1H), 8.07 (s, 1H), 7.50 (d, J=8.8 Hz, 2H), 7.25 (d, J=8.8 Hz, 2H), 6.00 (s, 1H), 4.56 (t, J=6.4 Hz 2H), 3.46 (s, 4H), 2.80 (t, J=6.0 Hz 2H), 2.42 (s, 4H), 1.26 (s, 9H) ppm.

Example 89: Preparation of 1-(4-((1-(4-bromophenyl)-pyrazolopyrimidine-4-yl)oxy)phenyl)-3-(5-tert-butylisoxazol-3-yl)urea (5a-9)

A compound (5a-9) was obtained from the compound (4a-26) and 4-bromobenzyl bromide by the synthesis method of the compound (5a-1) at a yield of 86.7%.
LCMS m/z: 562.2[M+H].

Example 90: Kinase Inhibition Activity Test of the Pyrazolopyrimidine Derivative of the Invention The purpose of this experiment was to test the inhibitory activity of the compound of the invention for in vitro kinase with the isotope labeling method (the γ phosphate group on ATP was labeled). In this experiment, the in vitro activity inhibition of such kinases as FLT3, VEGFR2, FLT1, FLT4, RET, c-RAF, B-RAF, c-KIT, PDGF$_α$, PDGF$_β$, FGFR2, FGFR1, EphA2, EphB2, SRC, ABL, ALK and Met was tested respectively. Staurosporine was reference molecule (or referred to as positive control). The kinase inhibition activity of the test compound was expressed by half-inhibitory concentration (IC$_{50}$) or the kinase activity inhibition rate of the test compound at a concentration of 10 μM. The IC$_{50}$ value could be obtained by calculating the kinase activity inhibition rate of the test compound at different concentrations.
1) Experimental Materials:
20 mM 3-(N-morpholinyl)propanesulfonic acid (MOPS); 1 mM ethylenediaminetetraacetic acid (EDTA), 0.01% Brij 35 (Brij-35), 5% glycerol, 0.1% mercaptoethanol, 1 mg/mL bovine serum albumin (BSA), 10 mM manganous dichloride solution (MnCl₂), 0.1 mg/mL glutamic acid/tyrosine (4:1) polypeptide (poly(Glu, Tyr)4:1), 50 μM EAIYAAPFAKKK (substrate of FLT3), 0.33 mg/mL myelin basic protein (substrate of VEGFR2), 250 μM KKKSPGEYVNIEFG (substrate of FLT1(h)), 500 μM GGEEEEYFELVKKKK (substrate of FLT4(h)), 250 μM KKKSPGEYVNIEFG (substrate of RET), 0.66 mg/mL myelin basic protein (substrate of C-RAF), 250 μM GGMEDIYFEFMGGKKK (substrate of c-Kit), 250 μM GGMEDIYFEFMGGKKK (substrate of PDGFα), 250 μM KKKSPGEYVNIEFG (substrate of FGFR1), 500 mM GGEEEEYFELVKKKK (substrate of SRC), 50 μM EAIYAAPFAKKK (substrate of ABL), 250 μM KKKSPGEYVNIEFG (substrate of ALK), 250 μM KKKSPGEYVNIEFG (substrate of Met(h)), 10 mM magnesium acetate and γ-$^{33}$ P-ATP solution, stop buffer (3% phosphate buffer), washing buffer (75 mM phosphate solution), methanol, Filtermat A membrane, FLT3, VEGFR2, FLT3, VEGFR2, FLT1, FLT4, RET, c-RAF, B-RAF, c-KIT, PDGFR$_α$, PDGFR$_β$, FGFR2, FGFR1, EphA2, EphB2, SRC, ABL, ALK, Met and other kinases, and the test compounds.
2) Experimental Method:
Buffers (8 mM MOPS with pH value of 7.0, 0.2 mM EDTA and 10 mM MnCl₂), (5-10 mU) kinases to be tested (FLT3, VEGFR2, FLT1, FLT4, RET, c-RAF, B-RAF, c-KIT, PDGFR$_α$, PDGFR$_β$, FGFR2, FGFR1, EphA2, EphB2, SRC, ABL, ALK and Met), substrates of kinases to be tested (refer to experimental materials), 10 mM magnesium acetate and γ-$^{33}$ P-ATP solution, and test compounds at different concentrations were added to a reaction tube orderly. Reaction started from addition of MgATP (the concentration of ATP was the Km value of corresponding kinase, i.e. the concentration of FLT3 was 200 μM, that of VEGFR2 was 90 μM, that of FLT1 was 200 μM, that of FLT4 was 200 μM, that of RET was 70 μM, that of c-RAF was 45 μM, that of B-RAF was 200 μM, that of c-KIT was 200 μM, that of PDGFRα was 120 μM, that of PDGFRβ was 200 μM, that of FGFR2 was 90 μM, that of FGFR1 was 200 μM, that of EphA2 was 155 μM, that of EphB2 was 10 μM, that of SRC was 45 μM, that of ABL was 45 μM, that of ALK was 200 μM and that of Met was 45 μM), and the reaction was incubated at room temperature for 40 minutes. Reaction was terminated with 5 μL 3% phosphate buffer finally, and 10 μL reaction solution was titrated to the Filtermat A membrane; solution was washed for 3 times with 75 mM phosphate solution with each time lasting 5 minutes, and then washed once with methanol. Finally, the Filtermat A membrane was dried, and scintillation counting was performed on the membrane, with scintillation count reflecting the phosphorylation degree of the substrates, so that the activity inhibition of kinase could be characterized.
3) Experimental Results:
The inhibitory activity of the compound in the invention for kinases (FLT3, VEGFR2, FLT1, FLT4, RET, c-RAF, B-RAF, c-KIT, PDGFR$_α$, PDGFR$_β$, FGFR2, FGFR1, EphA2, EphB2, SRC, ABL, ALK and Met) was tested by the experimental method.
IC$_{50}$ values (inhibitory activity value) of the test compounds (4a-2, 4a-6, 4a-25 and 4a-31) for several kinases are shown in Table 1.
IC$_{50}$ values (inhibitory activity value) of several test compounds for kinases (FLT3 and VEGFR2) are shown in Table 2.
Activity inhibition rates (%) of several test compounds for kinases (FLT3, VEGFR2, c-KIT, PDGFR$_α$, FGFR2, FGFR1, EphA2, EphB2, ABL, ALK and Met) at a concentration of 10 μM are shown in Table 3. ("--" in each table represents that test is not performed.)

TABLE 1

Inhibitory activity of test compounds for several kinases

| Kinase under test | IC$_{50}$ value (inhibitory activity value, μM) of test compounds for kinases | | | |
| --- | --- | --- | --- | --- |
|  | 4a-2 | 4a-6 | 4a-25 | 4a-31 |
| FLT3 | 0.039 | 0.009 | 0.016 | 0.005 |
| VEGFR2 | 0.012 | 0.011 | 0.012 | 0.011 |
| c-RAF | 0.072 | 0.082 | 0.053 | 0.046 |
| c-KIT | 0.507 | 0.313 | 0.911 | 0.087 |
| PDGFR$_α$ | 0.223 | 0.322 | 1.400 | <10.000 |
| PDGFR$_β$ | 0.408 | 0.184 | <10.000 | <10.000 |

TABLE 1-continued

Inhibitory activity of test compounds for several kinases

IC$_{50}$ value (inhibitory activity value, μM) of test compounds for kinases

| Kinase under test | 4a-2 | 4a-6 | 4a-25 | 4a-31 |
|---|---|---|---|---|
| FLT1 | <10.000 | 0.005 | <10.000 | <10.000 |
| FLT4 | <10.000 | 0.005 | <10.000 | <10.000 |
| RET | <10.000 | 0.004 | <10.000 | <10.000 |
| FGFR1 | <10.000 | 2.248 | <10.000 | <10.000 |
| FGFR2 | 1.805 | <10.000 | <10.000 | <10.000 |
| EphA2 | <10.000 | 0.056 | <10.000 | <10.000 |
| EphB2 | <10.000 | 0.138 | <10.000 | <10.000 |
| SRC | <10.000 | 3.012 | <10.000 | <10.000 |

TABLE 2

Inhibitory activity of test compounds for FLT3 and VEGFR2

| Test compound | VEGFR2 (IC$_{50}$/μM) | FLT3 (IC$_{50}$/μM) |
|---|---|---|
| 4a-1 | 0.030 | 0.027 |
| 4a-2 | 0.012 | 0.039 |
| 4a-6 | 0.011 | 0.009 |
| 4a-7 | 0.032 | 0.036 |
| 4a-8 | 0.029 | 0.038 |
| 4a-9 | 0.019 | 0.018 |
| 4a-10 | 0.021 | 0.025 |
| 4a-12 | 0.024 | 0.061 |
| 4a-13 | 0.037 | 0.024 |
| 4a-15 | 0.028 | 0.089 |
| 4a-24 | 0.014 | 0.017 |
| 4a-25 | 0.012 | 0.016 |
| 4a-26 | 0.012 | 0.008 |
| 4a-31 | 0.011 | 0.005 |

TABLE 3

Inhibition rate of test compounds for multiple kinases at a concentration of 10 μM Activity inhibition rate of test compounds for kinases at a concentration of 10 μM

| Test compound | VEGFR2 (h) | Flt3 (h) | c-Kit (h) | Abl/Abl (T315I)(h) | PDGFRα (h) | FGFR2 (h) |
|---|---|---|---|---|---|---|
| 4a-1 | 100 | 100 | 100 | 17 | 63 | 22 |
| 4a-2 | 100 | 100 | 100 | 86 | 93 | 80 |
| 4a-3 | 95 | 76 | 98 | 13 | 66 | 0 |
| 4a-4 | 91 | 57 | 80 | 0 | 49 | 0 |
| 4a-5 | 95 | 85 | 100 | 43 | 97 | 22 |
| 4a-6 | 100 | 100 | 100 | 79 | 97 | 56 |
| 4a-7 | 100 | 100 | 98 | 60 | 89 | 51 |
| 4a-8 | 100 | 100 | 95 | 34 | 64 | 6 |
| 4a-9 | 100 | 100 | 29 | 15 | 24 | 18 |
| 4a-10 | 100 | 100 | 49 | 67 | 52 | 53 |
| 4a-11 | 78 | 64 | 52 | — | — | — |
| 4a-12 | 100 | 100 | 58 | 78 | 52 | 71 |
| 4a-13 | 100 | 100 | 85 | 27 | 63 | 13 |
| 4a-14 | 100 | 100 | 92 | 14 | 90 | 9 |
| 4a-15 | 100 | 100 | 66 | 99 | 48 | 100 |
| 4a-16 | 91 | 76 | 77 | — | — | — |
| 4a-17 | 95 | 87 | 62 | 11 | 46 | 4 |
| 4a-18 | 95 | 81 | 100 | 45 | 96 | 22 |
| 4a-19 | 92 | 73 | 93 | 21 | 84 | 17 |
| 4a-20 | 64 | 66 | 98 | 19 | 93 | 19 |
| 4a-21 | 72 | 68 | 92 | 26 | 85 | 9 |
| 4a-23 | 100 | 100 | >90 | >30 | >50 | >50 |
| 4a-24 | 100 | 100 | >90 | >50 | >50 | >50 |
| 4a-25 | 100 | 100 | >90 | >50 | >50 | >50 |
| 4a-26 | 100 | 100 | >90 | >50 | >50 | >50 |
| 4a-27 | 100 | 100 | >90 | >50 | >50 | >50 |
| 4a-28 | 100 | 100 | >90 | >50 | >50 | >50 |
| 4a-30 | 100 | 100 | >90 | >50 | >50 | >50 |
| 4a-31 | 100 | 100 | >90 | >50 | >50 | >50 |
| 4a-31 | 100 | 100 | >90 | >50 | >50 | >50 |
| 4a-34 | 100 | 100 | >90 | >50 | >50 | >50 |
| 4a-35 | 100 | 100 | >90 | >50 | >50 | >50 |
| 4a-36 | 100 | 100 | >90 | >50 | >50 | >50 |
| 4a-38 | 100 | 100 | 100 | 78 | 98 | 97 |
| 4a-40 | >90 | 100 | >90 | 100 | >50 | >50 |
| 4a-44 | >90 | >90 | >90 | >30 | >30 | >30 |
| 4a-51 | 100 | >90 | >90 | >50 | >50 | >50 |
| 4b-1 | 93 | 30 | >30 | — | >30 | 22 |
| 4b-2 | 88 | 0 | >30 | — | >30 | 66 |
| 4b-3 | 96 | 72 | >30 | — | >30 | 45 |
| 4b-4 | 94 | 59 | >30 | — | >30 | 32 |
| 4b-5 | 97 | 95 | >30 | — | >30 | 52 |
| 4b-6 | 95 | 81 | >30 | — | >30 | 32 |
| 4b-7 | 92 | 91 | >30 | — | >30 | 69 |
| 4b-8 | >90 | >90 | >90 | — | >30 | >30 |
| 4c-1 | 100 | >90 | >90 | >30 | >50 | >50 |
| 4c-2 | 100 | >90 | >90 | >30 | >50 | >50 |
| 4c-3 | 100 | >90 | >90 | >30 | >50 | >50 |
| 5a-1 | >90 | >90 | >90 | — | >30 | >50 |
| 5a-3 | 100 | 100 | >90 | >30 | >30 | >30 |
| 5a-4 | >90 | >90 | >30 | — | >30 | >30 |
| 5a-8 | >30 | >90 | >30 | — | >30 | >30 |
| 5a-9 | >50 | >50 | — | — | >30 | >30 |

Experimental results show that the test compounds have strong inhibitory activity for FLT3 and VEGFR2, and some of test compounds also have good inhibitory activity for kinases (FLT1, FLT4, RET, c-RAF, B-RAF, c-KIT, PDGFRα, PDGFRβ, FGFR2, FGFR1, EphA2, EphB2, SRC, ABL, ALK and Met).

Example 91: Experiment on In Vitro Human Tumor Cell Proliferation Inhibition for Pyrazolopyrimidine Derivative of the Invention The purpose of the experiment was to test the inhibition activity of the compounds of the invention for in vitro human tumor cell proliferation by the methyl thiazolyl tetrazolium (MTT) colorimetry.

1) Experimental Materials:

Main reagents: RPMI-1640, fetal bovine serum, pancreatin, etc. were purchased from Gibco BRL Company (Invitrogen Corporation, USA) and IMDM medium that was purchased from American Type Culture Collection (ATCC). Methyl thiazolyl tetrazolium (MTT) and dimethyl sulfoxide (DMSO) were products from Sigma Company (USA). Pyrazolopyrimidine derivatives were composed by the inventor. During in vitro experiment, 100% DMSO was prepared into 10 mM storage solution, the solution was stored in a refrigerator at −20° C. for future use, and was diluted to the required concentration with complete culture solution before use.

Cell line and culture: Human leukemia cell line MV4-11, Jurkat, K562, human thyrophyma cell line TT, human gastric carcinoma cell line MKN-45, human malignant melanoma cell lines A375 and A875, human pancreatic carcinoma cell line panc-1, human cervical carcinoma cell line HELA, human colorectal carcinoma cell line HCT116, etc. were purchased from American type culture collection and were preserved by this laboratory. All leukemia cell lines (except MV4-11), gastric carcinoma cell lines and thyrophyma cell lines were cultured in RPMI-1640 complete medium containing 10% fetal bovine serum, 100 U/mL penicillin and 100 μg/mL streptomycin at 37° C. in 5% $CO_2$. The remaining cell lines were cultured in DMEM complete medium containing 10% fetal bovine serum (containing 20% MV4-11 cell), 100 U/mL penicillin and 100 g/mL streptomycin at 37° C. in 5% $CO_2$.

2) Experimental Method:

Cell suspension with cell concentration of $1-2\times10^4$/mL was adjusted with the complete cell medium and inoculated in a 96-well plate, with each well filled with 200 μl cell suspension that was cultured overnight. On the next day, supernatant was sucked and abandoned (supernatant was sucked upon centrifugation of suspension cells), and then cells were processed with test compounds at gradient concentrations respectively. Meanwhile, a negative control group free from drug and a solvent control group with equal volume were set, and the DMSO concentration was 0.1%. Each dose group was provided with three wells and cultured at 37° C. in 5% $CO_2$. After 72 hours, 20 μl 5 mg/mL MTT reagent was added to each well, and cultured for another 2 to 4 hours, the supernatant was abandoned; 150 μL DMSO was added to each well again, vibrated and mixed evenly for 15 minutes; the absorbance (A) values (proportional to living cell amount) were determined with a microplate reader (λ=570 nm) and averaged. Relative cell proliferation inhibition rate=(control group A570−experimental group A570)/control group A 570×100%. Experiment was repeated for 3 times at least. Experimental data were expressed with means, data statistics were tested by t, and $P<0.05$ means that difference has a statistical significance. The cell proliferation inhibition effects of all compounds as follows are expressed by $IC_{50}$ or inhibition rate.

3) Experimental Results:

Proliferation inhibition activities for human leukemia cell lines (MV4-11, Jurkat and K562), human thyrophyma cell line (TT), human gastric carcinoma cell line (MKN-45), human malignant melanoma cell lines (A375 and A875), human pancreatic carcinoma cell line (panc-1), human cervical carcinoma cell line (HELA), human colorectal carcinoma cell line (HCT116), etc. were tested by the method.

Proliferation inhibition activities ($IC_{50}$) of test compounds for various cell lines are shown in Table 4.

TABLE 4

Proliferation inhibition activities ($IC_{50}$: μM) of test compounds for various cell lines

| Test compound | MV4-11 | MKN 45 | A375 | A875 | Panc-1 | Jurkat | K562 | HCT 116 | TT | HELA |
|---|---|---|---|---|---|---|---|---|---|---|
| 4a-1 | 0.005 | <50 | <50 | 3-10 | <50 | <50 | <50 | <50 | <50 | <50 |
| 4a-2 | 0.003 | 8.235 | 2.121 | 4.123 | <50 | 8.723 | <50 | <50 | 3.423 | <50 |
| 4a-3 | 0.083 | <50 | 4.704 | <50 | 7.761 | 3.229 | <50 | <50 | 3-10 | <50 |
| 4a-4 | 0.037 | <50 | 3.205 | 8.013 | 1.068 | <50 | <50 | <50 | — | <50 |
| 4a-5 | 0.019 | <50 | <50 | <50 | <50 | 6.477 | <50 | <50 | — | <50 |
| 4a-6 | 0.004 | 9.708 | 3.452 | 6.239 | <50 | 4.279 | <50 | <50 | 0.312 | <50 |
| 4a-7 | 0.011 | <50 | <50 | <50 | <50 | <50 | <50 | <50 | — | <50 |
| 4a-8 | 0.053 | 7.653 | 4.648 | 6.972 | 4.648 | <50 | <50 | 5.696 | — | 8.487 |
| 4a-9 | 0.043 | 7.633 | <50 | <50 | 2.313 | <50 | 2.704 | 4.561 | 1.634 | 4.984 |
| 4a-10 | 0.009 | 5.281 | <50 | <50 | <50 | 9.929 | <50 | <50 | — | <50 |
| 4a-11 | 9.587 | <50 | 3-10 | <50 | — | — | <50 | — | 3-10 | — |
| 4a-12 | 0.017 | 8.293 | <50 | <50 | <50 | <50 | 9.122 | <50 | — | <50 |
| 4a-13 | 0.018 | 6.684 | <50 | <50 | <50 | <50 | <50 | <50 | 3-10 | <50 |
| 4a-14 | 0.059 | <50 | <50 | <50 | <50 | <50 | 3.513 | <50 | — | <50 |
| 4a-15 | 0.320 | <50 | <50 | <50 | <50 | <50 | <50 | <50 | — | <50 |
| 4a-16 | 0.089 | 3.224 | <50 | <50 | <50 | <50 | <50 | <50 | — | <50 |
| 4a-17 | 0.082 | <50 | 6.578 | <50 | 2.142 | 8.671 | <50 | <50 | 3-10 | <50 |
| 4a-18 | 0.112 | <50 | <50 | <50 | <50 | 3-10 | <50 | <50 | — | <50 |
| 4a-19 | 0.124 | <50 | <50 | <50 | <50 | — | <50 | <50 | — | <50 |
| 4a-20 | 0.363 | <50 | <50 | <50 | <50 | <50 | <50 | <50 | — | <50 |
| 4a-21 | 1.371 | <50 | <50 | <50 | <50 | <50 | <50 | <50 | — | <50 |
| 4a-22 | 0.932 | 3-10 | 3-10 | 3-10 | — | 3-10 | <50 | — | <50 | — |
| 4a-23 | 0.449 | <50 | <50 | <50 | <50 | <50 | <50 | <50 | 3-10 | <50 |
| 4a-24 | 0.0004 | 2.837 | 6.941 | 4.269 | <50 | — | <50 | 6.749 | 1.546 | 5.506 |
| 4a-25 | 0.0003 | 1.298 | 3-10 | 3-10 | 3-10 | <50 | 3-10 | 3-10 | 1.021 | 3-10 |
| 4a-26 | 0.0003 | 1.123 | 3-10 | 3-10 | 3-10 | 3-10 | 3-10 | 3-10 | 2.124 | 3-10 |
| 4a-27 | 0.0005 | 2.081 | 3-10 | 3-10 | <50 | <50 | <50 | 3-10 | 3-10 | 3-10 |
| 4a-28 | 0.0012 | 3-10 | <50 | <50 | <50 | 3-10 | 3-10 | <50 | 3-10 | <50 |
| 4a-29 | 1.754 | <50 | <50 | <50 | <50 | <50 | 3-10 | — | 3-10 | — |
| 4a-30 | 0.005 | <50 | <50 | <50 | — | <50 | — | — | 3-10 | — |
| 4a-31 | 0.0004 | <50 | 3-10 | 3-10 | 3-10 | 6.096 | 3-10 | — | 0.943 | 3-10 |
| 4a-32 | 0.001 | 3-10 | 3-10 | 3-10 | 3-10 | 3-10 | — | <50 | — | — |
| 4a-33 | 0.001 | 3-10 | 3-10 | 3-10 | — | — | — | — | 1.236 | — |
| 4a-34 | 0.001 | <50 | 3-10 | 3-10 | 3-10 | 3-10 | <50 | <50 | 3-10 | — |
| 4a-35 | 0.025 | <50 | <50 | <50 | — | — | — | <50 | <50 | 3-10 |
| 4a-36 | 0.008 | <50 | <50 | <50 | — | — | <50 | <50 | 3-10 | — |
| 4a-37 | 0.072 | <50 | <50 | <50 | <50 | — | — | <50 | <50 | <50 |
| 4a-38 | 0.0008 | 3-10 | 3-10 | 3-10 | 3-10 | <50 | 3-10 | <50 | 3-10 | <50 |
| 4a-39 | <1.000 | <50 | <50 | <50 | <50 | — | <50 | <50 | — | <50 |
| 4a-40 | <1.000 | 3-10 | 3-10 | 3-10 | — | — | <0.100 | <50 | — | — |
| 4a-41 | 7.822 | <50 | <50 | <50 | <50 | <50 | <50 | <50 | <50 | <50 |
| 4a-42 | 6.207 | <50 | <50 | <50 | <50 | <50 | <50 | <50 | <50 | <50 |
| 4a-43 | <5.000 | <50 | <50 | <50 | <50 | <50 | <50 | <50 | 4.567 | <50 |
| 4a-44 | 1.114 | <50 | <50 | <50 | <50 | <50 | <50 | <50 | <50 | — |
| 4a-45 | 0.003 | <50 | <10 | <10 | 1-3 | 1-3 | 3-10 | <10 | 1-3 | <50 |
| 4a-46 | 0.003 | <50 | <10 | <10 | 1-3 | 1-3 | 3-10 | <10 | 1-3 | <50 |

TABLE 4-continued

Proliferation inhibition activities (IC$_{50}$: μM) of test compounds for various cell lines

| Test compound | MV4-11 | MKN 45 | A375 | A875 | Panc-1 | Jurkat | K562 | HCT 116 | TT | HELA |
|---|---|---|---|---|---|---|---|---|---|---|
| 4a-47 | <50 | <50 | <50 | <50 | <50 | <50 | <50 | <50 | <50 | <50 |
| 4a-48 | 0.066 | <50 | <50 | <50 | — | <50 | <50 | <50 | <50 | — |
| 4a-49 | 6.369 | <50 | <50 | <50 | — | — | <50 | <50 | <50 | — |
| 4a-50 | <50 | <50 | <50 | <50 | — | — | <50 | <50 | <50 | — |
| 4a-51 | 7.422 | — | <50 | <50 | — | <50 | — | — | <50 | — |
| 4a-52 | 0.128 | <50 | — | — | — | — | — | — | <50 | — |
| 4a-53 | — | — | <50 | <50 | <50 | <50 | <50 | <50 | — | — |
| 4b-1 | <50 | <50 | <50 | <50 | <50 | <50 | 3.446 | <50 | — | <50 |
| 4b-2 | 8.034 | <50 | <50 | <50 | <50 | <50 | <50 | <50 | — | <50 |
| 4b-3 | 1.651 | <50 | <50 | <50 | <50 | <50 | <50 | <50 | — | <50 |
| 4b-4 | 2.050 | <50 | <50 | <50 | <50 | <50 | <50 | <50 | — | <50 |
| 4b-5 | 0.050 | 7.642 | — | — | — | — | — | — | 9.478 | — |
| 4b-6 | 0.729 | <50 | <50 | <50 | <50 | <50 | <50 | <50 | — | — |
| 4b-7 | 0.667 | <50 | <50 | <50 | <50 | <50 | <50 | <50 | — | — |
| 4b-8 | 0.219 | <50 | — | — | — | <50 | — | — | <50 | — |
| 4c-1 | 0.012 | — | <50 | <50 | <50 | <50 | — | — | — | — |
| 4c-2 | 0.039 | 8.712 | <50 | <50 | <50 | <50 | — | — | 7.891 | — |
| 4c-3 | <1.000 | 3-10 | <50 | <50 | <50 | <50 | <50 | <50 | 3-10 | <50 |
| 5a-1 | 0.078 | 8.641 | <50 | <50 | <50 | — | <50 | — | — | — |
| 5a-2 | 1.585 | <50 | — | — | — | — | — | — | — | — |
| 5a-3 | 0.002 | <50 | — | — | <50 | <50 | — | — | 1.672 | <50 |
| 5a-4 | <1.000 | <50 | <50 | <50 | <50 | <50 | <50 | <50 | 9.890 | — |
| 5a-5 | 0.019 | <50 | — | — | <50 | <50 | — | — | <50 | — |
| 5a-6 | 0.028 | <50 | — | — | — | <50 | — | — | 4.127 | <50 |
| 5a-7 | — | <50 | <50 | <50 | <50 | <50 | — | — | <50 | — |
| 5a-8 | 0.173 | <50 | — | — | — | <50 | — | — | 1.547 | — |
| 5a-9 | <3.000 | <50 | <50 | <50 | <50 | <50 | <50 | <50 | — | <50 |
| 4a-54 | 0.07974 | — | — | — | 20.12 | — | <50 | 14.86 | <50 | — |
| 4a-55 | 0.0542 | — | — | — | <50 | <50 | <50 | <50 | — | — |
| 4a-56 | 0.0000354 | — | — | — | — | — | — | — | — | 4.3 |
| 4a-57 | 0.0004371 | — | — | — | — | — | — | — | — | 3.2 |
| 4a-58 | 0.0000146 | — | — | — | — | — | — | — | — | <50 |
| 4a-59 | 0.00000984 | — | — | — | — | — | — | — | — | <50 |
| 4a-60 | 0.000348 | — | — | — | <50 | — | — | 7.306 | — | 5.0 |
| 4a-61 | 0.00198 | — | — | — | <50 | — | — | 21.03 | — | <50 |
| 4a-62 | 0.00367 | — | — | — | <50 | — | — | 14.73 | — | <50 |
| 4a-63 | 0.03905 | — | — | — | <50 | — | — | 22.53 | — | <50 |
| 4a-64 | 1.862 | — | — | — | <50 | — | <50 | <50 | — | <50 |
| 4a-65 | 0.080 | — | — | — | <50 | — | <50 | <50 | — | <50 |

Results show that test compounds have very strong inhibitory activity for the mutant cell line MV4-11 of FLT3-ITD, several test compounds have good inhibitory activity for the RET mutant cell line TT, and several test compounds also have inhibitory activity for other tumor cell lines including MKN45 and A375, etc.

Example 92: In Vivo Anti-Leukemia Tumor Experiment of Compound 4a-2

The purpose of the experiment was to test the in vivo anti-tumor effect of the compound of the invention. In this experiment, NOD-SCID mice-subcutaneous human Leukemia tumor model were used to test the in vivo anti-tumor activity of the compound 4a-2. The cell line used was human leukemia cell line MV4-11. The drug (Sorafenib) undergoing anti-leukemia clinical trial was used as the positive control.

1) Experimental Materials:
IMDM, fetal bovine serum, pancreatin, etc. were purchased from Gibco BRL company (Invitrogen Corporation, USA); IMDM medium was purchased from American Type Culture Collection (ATCC); human leukemia cell line MV4-11 was purchased from American Type Culture Collection; NOD-SCID mice were purchased from Beijing HFK Bioscience Co., Ltd.; and sorafenib was purchased from Nanjing Dirise Chemical Co., Ltd.

2) Experimental Method:
NOD-SCID mice at age of 6 to 8 weeks were used, and MV4-11 cells were inoculated at the subcutaneous posterior ribs of the mice at a concentration of $1 \times 10^7/0.1$ mL/mouse; after the tumors grew to 400-500 mm$^3$ (for about 20 days), mice (n=6) were grouped and subject to oral intragastric administration.

Experiment grouping: drug solvent control group (12.5% castor oil+12.5% ethanol+75% water)
Compound 4a-2: 1 mg/kg q.d.;
Compound 4a-2: 3 mg/kg q.d.;
Compound 4a-2: 10 mg/kg q.d.;
Positive control sorafenib: 3 mg/kg q.d.;
Each group of drug was dissolved in 12.5% castor oil+12.5% ethanol+75% water.

Observation targets: Mouse weight and long and short diameters of tumor were measured every 3 days, and tumor volume (length×width$^2$×0.52) was calculated to observe for diarrhea, convulsion, rash, significant weight loss and other reactions.

3) Experimental Results:
Tumor growth curves of different groups measured in the experiments are shown in FIG. 1.
Experimental results show that the test compound (4a-2) has obvious in vivo growth inhibition effect on the mutant human leukemia cell line MV4-11 of FLT3-ITD, can obviously inhibit tumor growth or extinct tumor completely at a daily dose of 3 mg/kg or above, and presents the inhibition effect superior to the positive control (sorafenib). Weight loss, rash, diarrhea and other adverse reactions were not found in mice during administration, which indicates that the test compound (4a-2) has very low toxicity within the administration dosage range at the test dose.

Example 93: In Vivo Anti-Leukemia Tumor Experiment of Compound 4a-31

Figure 2:
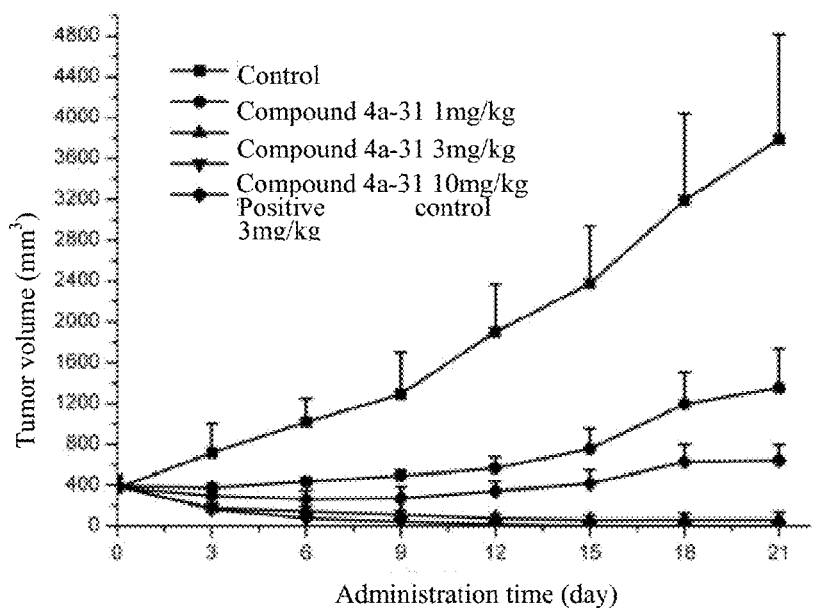
FIG. 2 shows tumor inhibition curve of compound 4a-31 in nude mice-subcutaneous human leukemia MV4-11 model.

The purpose of the experiment was to test the in vivo anti-tumor effect of the compound of the invention. In this experiment, NOD-SCID mice-subcutaneous human leukemia tumor model in mouse was used to test the in vivo anti-tumor activity of the compound 4a-31. The cell line used was human leukemia cell line MV4-11. The drug (Sorafenib) undergoing anti-leukemia clinical trial was used as the positive control.
1) Experimental Materials:
 IMDM, fetal bovine serum, pancreatin, etc. were purchased from Gibco BRL company (Invitrogen Corporation, USA); IMDM medium was purchased from American Type Culture Collection (ATCC); human leukemia cell line MV4-11 was purchased from American Type Culture Collection; and NOD-SCID mice were purchased from Beijing HFK Bioscience Co., Ltd.
2) Experimental Method
 NOD-SCID mice at age of 6 to 8 weeks were used, and MV4-11 cells were inoculated at the subcutaneous posterior ribs of the mice at a concentration of $1\times10^7/0.1$ mL/mouse; after the tumors grew to 400-500 mm$^3$ (for about 20 days), mice (n=6) were grouped and subject to oral intragastric administration.
 Experiment grouping: drug solvent control group (12.5% castor oil+12.5% ethanol+75% water)
 Compound 4a-31: 1 mg/kg q.d.;
 Compound 4a-31: 3 mg/kg q.d.;
 Compound 4a-31: 10 mg/kg q.d.;
 Positive control (sorafenib): 3 mg/kg q.d.;
 Each group of drug was dissolved in 12.5% castor oil+12.5% ethanol+75% water.
 Observation targets: Mouse weight and long and short diameters of tumor were measured every 3 days, and tumor volume (length×width$^2$×0.52) was calculated to observe for diarrhea, convulsion, rash, significant weight loss and other reactions.
3) Experimental Results
 Tumor growth curves of different groups measured in the experiment are shown in FIG. 2.
 Experimental results show that the test compound 4a-31 has obvious in vivo growth inhibition effect on the mutant human leukemia cell line MV4-11 of FLT3-ITD, can obviously inhibit tumor growth at daily dose of 1 mg/kg and extinct tumor completely at daily dose of 3 mg/kg or above, and presents the inhibition effect superior to the positive control (sorafenib). Weight loss, rash, diarrhea and other adverse reactions were not found in mice during administration, which indicates that the test compound 4a-31 has very low toxicity within the administration dosage range at the test dose.

Example 94: In Vivo Anti-Melanoma Experiment of Compound 4a-2

Figure 3:
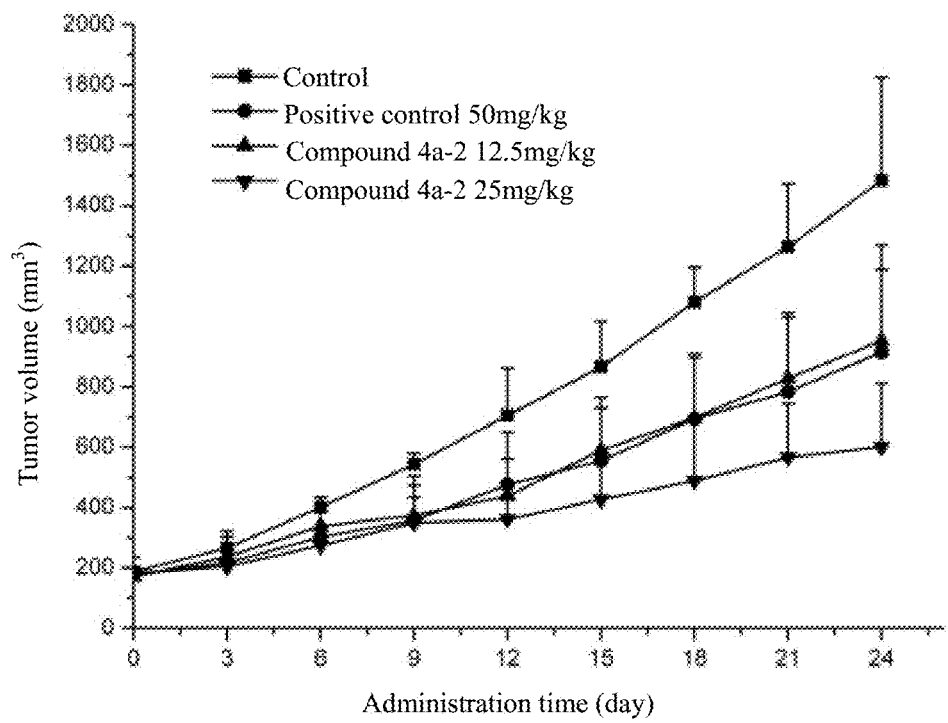
FIG. 3 shows tumor inhibition curve of compound 4a-2 in nude mice-subcutaneous human malignant melanoma WM2664 model.

The purpose of the experiment was to test the in vivo anti-tumor effect of the compound of the invention. In this experiment, nude mice-subcutaneous malignant melanoma model was used to test the in vivo anti-tumor activity of the compound 4a-2 of the invention. The cell line used was human malignant melanoma cell line WM2664. The drug (sorafenib) undergoing anti-melanoma clinical trial was used as the positive control.
1) Experimental Materials:
 DMEM, fetal bovine serum, pancreatin, etc. were purchased from Gibco BRL Company (Invitrogen Corporation, USA); human malignant melanoma cell line WM2664 was purchased from American Type Culture Collection (ATCC); BALB/C nude mice were purchased from Beijing HFK Bioscience Co., Ltd.; and castor oil (C5135-500G) was product of Sigma Company.
2) Experimental Method:
 BALB/C nude mice at age of 6 to 8 weeks were used, and WM2664 cells were inoculated at the subcutaneous posterior ribs of the mice at a concentration of $5\times106/0.1$ mL/mouse; after the tumors grew to 200-300 mm$^3$ (for about 15 days), mice (n=6) were grouped and subject to oral intragastric administration.
 Experiment grouping: drug solvent control group (12.5% castor oil+12.5% ethanol+75% water)
 Positive control (sorafenib) group: 50 mg/kg q.d.;
 Compound 4a-2: 12.5 mg/kg q.d.;
 Compound 4a-2: 25 mg/kg q.d.;
 Each group of drug was dissolved in 12.5% castor oil+12.5% ethanol+75% water.
 Observation targets: Mouse weight and long and short diameters of tumor were measured every 3 days, and tumor volume (length×width$^2$×0.52) was calculated to observe for diarrhea, convulsion, rash, significant weight loss and other reactions.
3) Experimental Results:
 Tumor growth curves of different groups measured in the experiment are shown in FIG. 3.
 Experimental results show that the test compound 4a-2 has obvious in vivo growth inhibition effect on the mutant human malignant melanoma cell line WM2664 of BRAF$^{V600D}$, can obviously inhibit tumor growth at the dose of 25 mg/kg/d, and is more effective than sorafenib at daily dose of 50 mg/kg. Weight loss, rash, diarrhea and other adverse reactions were not found in nude mice during administration, which indicates that the test compound 4a-2 has very low toxicity within the administration dosage range at the test dose.

Example 95: In Vivo Anti-Tumor Experiment of Compound 4a-6

The purpose of the experiment was to test the in vivo anti-tumor effect of the compound of the invention. In this experiment, nude mouse-subcutaneous inoculation human colorectal carcinoma model and human glioma model were respectively used to test the in vivo anti-tumor activity of the compound (4a-6) of the invention. The cell lines used were human colorectal carcinoma cell line HT29 and human glioma cell line U251.
1) Experimental Materials:
 DMEM, fetal bovine serum, pancreatin, etc. were purchased from Gibco BRL Company (Invitrogen Corporation, USA); DMEM medium was purchased from American Type Culture Collection (ATCC); human colorectal carcinoma cell line HT29 and human glioma cell line U251 BALB/C were purchased from American Type Culture Collection; BALB/C nude mice were purchased from Institute of Zoology, Chinese Academy of Science; and cremopher (C5135-500G) was purchased from Sigma Company.

2) Experimental Method:

BALB/C nude mice at age of 6 to 8 weeks were used, and in the human colorectal carcinoma cell model, HT29 cells were inoculated at the subcutaneous posterior ribs of the mice at a concentration of $1\times10^7/0.1$ mL/mouse; after the tumors grew to 150-200 mm$^3$ (for about 10 days), mice (n=6) were grouped and subject to oral intragastric administration. For the human glioma model, U251 cells were inoculated at the subcutaneous posterior ribs of the mice at a concentration of $5\times10^6/0.1$ mL/mouse; after the tumors grew to 150-200 mm$^3$ (for about 14 days), mice (n=6) were grouped and subject to oral intragastric administration.

Experiment grouping: drug solvent control group (12.5% castor oil+12.5% ethanol+75% water)

Compound 4a-6: 15 mg/kg q.d.;
Compound 4a-6: 30 mg/kg q.d.;
Compound 4a-6: 60 mg/kg q.d.;
Positive control (sorafenib) group: 30 mg/kg q.d.;

Each group of drug was dissolved in 12.5% castor oil+12.5% ethanol+75% water.

Observation targets: mouse weight and long and short diameters of tumor were measured every 3 days, and tumor volume (length×width$^2$×0.52) was calculated to observe for diarrhea, convulsion, rash, significant weight loss and other reactions.

Figure 4:
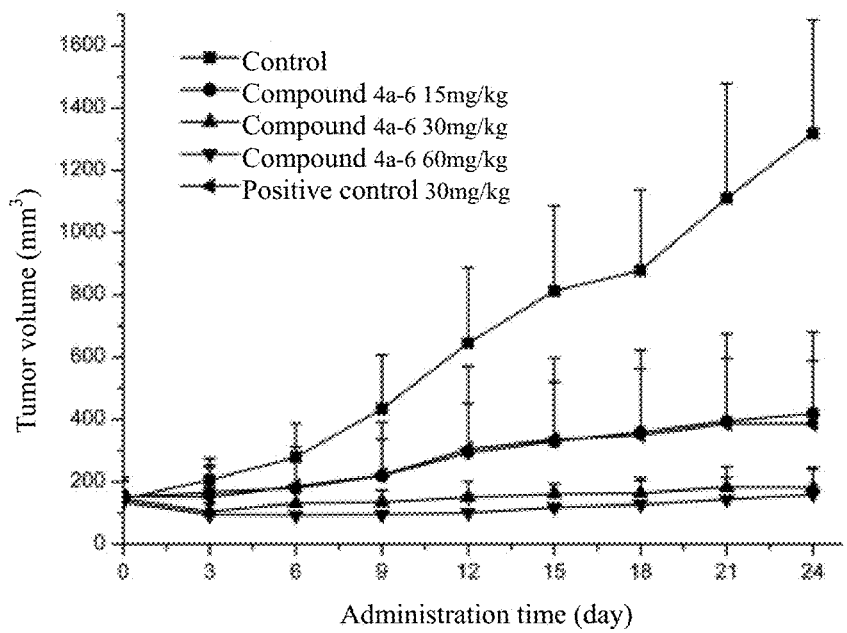
FIG. 4 shows tumor inhibition curve of compound 4a-6 in nude mice-subcutaneous human colorectal carcinoma HT29 model.
Figure 5:
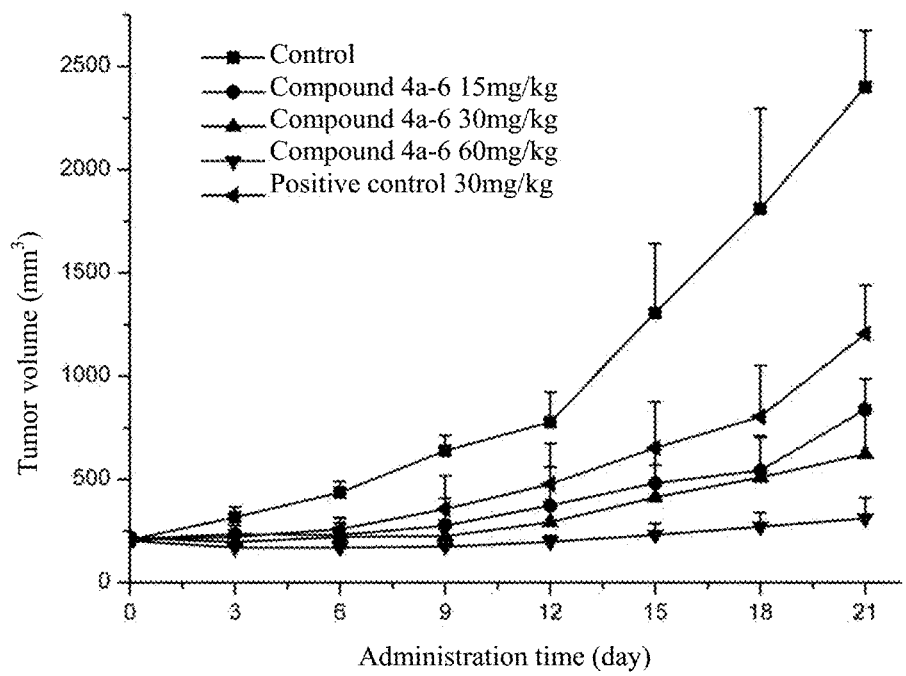
FIG. 5 shows tumor inhibition curve of compound 4a-6 in nude mice-subcutaneous human glioma U251 model.

3) Experimental Results:

The tumor growth curves of different groups of human colorectal carcinoma model HT29 measured in the experiment are shown in FIG. 4, and the tumor growth curves of different groups of human glioma model U251 measured in the experiment are shown in FIG. 5.

Experimental results show that test compound 4a-6 has obvious in vivo growth inhibition effect on the two tumor models, and can obviously inhibit tumor growth at daily dose of 30 mg/kg or above. Weight loss, rash, diarrhea and other adverse reactions were not found in nude mice during administration, which indicates that the test compound 4a-6 has very low toxicity within the administration dosage range at the test dose.

Experiment 96

Test on Angiogenesis Inhibition Activity of Compounds 4a-6 and 4a-31 for Transgenic Zebrafish The purpose of the experiment was to test the in vivo new blood vessel inhibition activity of the compounds of the invention by observing the inhibition of the compounds of the invention on inter segmental blood vessels of transgenic zebrafish (FLK1-GFP) at different concentrations. The new blood vessel inhibition activity of the test compounds was expressed by the inhibition degree of the test compounds for the inter segmental blood vessels of zebrafish at concentrations of 10 ug/mL, 3 ug/mL and 1 ug/mL.

1) Experimental Materials:

Transgenic zebrafish (FLK1-GFP): cultivated by this laboratory

Experiment reagents: dimethyl sulfoxide (DMSO), test compounds

Major experimental apparatus: fluorescence microscope, stereomicroscope, CCD camera, etc.

2) Experimental Method:

Acquisition of zebrafish embryos: The zebrafish used by this laboratory was fluorescent transgenic zebrafish (FLK1: GFP). Refer to Westerfield method for breeding and cultivation of zebrafish. The day before spawns were obtained, male and female zebrafish were paired at the ratio of 1:1. On the second day, the male and female zebrafish naturally mated and spawned at a temperature of about 28° C. under sufficient illumination. Enough zebrafish embryos were collected, washed, placed into embryo culture media, and put into a 28° C. incubator for culture. The survival of embryos was identified by morphological and phylogenetic standards, and dead embryos were white and taken out timely to prevent deterioration of water quality.

Medication: Ten hours after zebrafish embryos were fertilized (a microscopy was used to observe the process that the zebrafish embryos developed to bud period), healthy embryos were selected at random for grouping, a 24-well plate was added with 10 zebrafish embryos in each well, all culture media were removed by sucking, and compound solutions at different concentrations were added; The concentrations of each compound were set to be 10 ug/mL, 3 ug/mL and 1 ug/mL respectively. A blank control was set without addition of any compound, and was put into a 28° C. incubator for culture.

Result observation: Thirty one hours after the zebrafish embryos were fertilized, spawns were taken out and hatched zebrafish was peeled off; and then the hatched zebrafish was put onto slide, 1‰ tricaine solution was added to narcotize the fish body, and 1.5% methylcellulose was used to fix the fish body; and the inter segmental vessels (ISV) were observed, counted and photographed under a fluorescence microscope.

Figure 6:
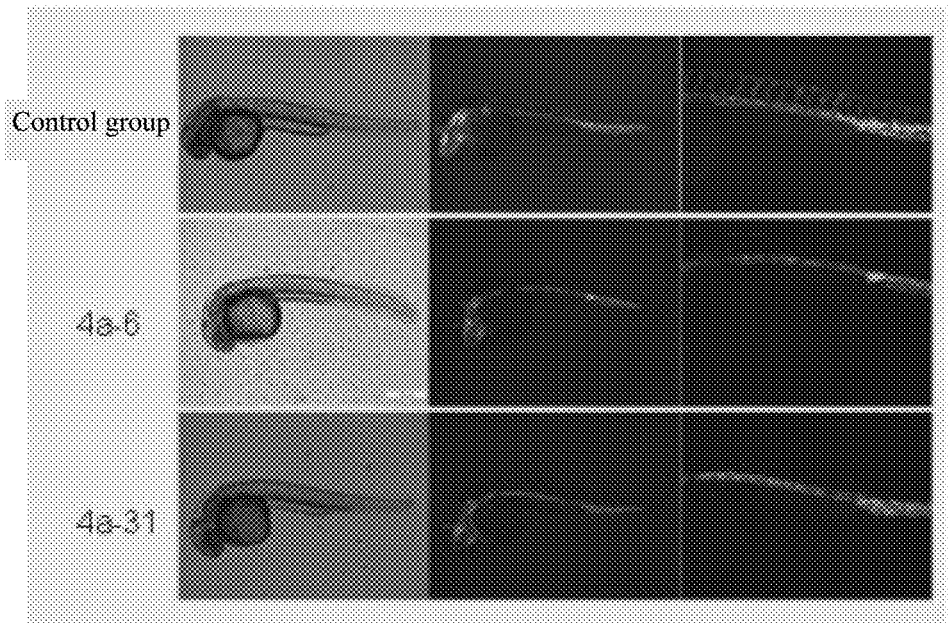
FIG. 6 shows angiogenesis inhibition of compounds 4a-6 and 4a-31 for FLK1 transgenic zebrafish at a concentration of 1 μg/mL.

3) Experimental Results:

FIG. 6 shows the angiogenesis inhibition of compounds 4a-6 and 4a-31 for FLK1 transgenic zebrafish at a concentration of 1 g/mL. Results show that compounds 4a-6 and 4a-31, compared with the control group, can inhibit angiogenesis of zebrafish very well. The experimental results show that most compounds prepared in the examples of the invention have very good inhibitory activity for new blood vessel of FLK1 transgenic zebrafish, which reflects that these compounds have very good inhibitory activity for VEGFR2.

Example 97: In Vivo Anti-Leukemia Tumor Experiment of Compound 4a-58

The purpose of the experiment was to test the in vivo anti-tumor effect of the compound of the invention. In this experiment, NOD-SCID mice-subcutaneous human leukemia solid tumor model was used to test the in vivo anti-tumor activity of the compound 4a-58. The cell line used was human acute myeloid leukemia cell line MV4-11, with anti-leukemia drug Quizartinib (AC220) as a positive control.

1) Experimental Materials:

IMDM, fetal bovine serum, pancreatin, etc. were purchased from Gibco BRL company (Invitrogen Corporation, USA); IMDM medium was purchased from American Type Culture Collection (ATCC); human leukemia cell line MV4-11 was purchased from American Type Culture Collection; and NOD-SCID mice were purchased from Beijing HFK Bioscience Co., Ltd.

2) Experimental Method

NOD-SCID mice at age of 6 to 8 weeks were used, and MV4-11 cells were inoculated at the subcutaneous posterior ribs of the mice at a concentration of $1\times10^7/0.1$ mL/mouse; and after the tumors grew to be more than 2000 mm$^3$, mice (n=3) were grouped and subject to oral intragastric administration.

Experiment grouping: compound 4a-58: 3 mg/kg q.d.;
Compound 4a-58: 10 mg/kg q.d.;
Positive control AC220: 3 mg/kg q.d.;
Positive control AC220: 10 mg/kg q.d.;
Each group of drug was dissolved in 12.5% castor oil+ 12.5% ethanol+75% water.

Observation targets: Mouse weight and long and short diameters of tumor were measured every 3 days, and tumor volume (length×width$^2$×0.52) was calculated to observe for diarrhea, convulsion, rash, significant weight loss and other reactions.

3) Experimental Results

Figure 7:
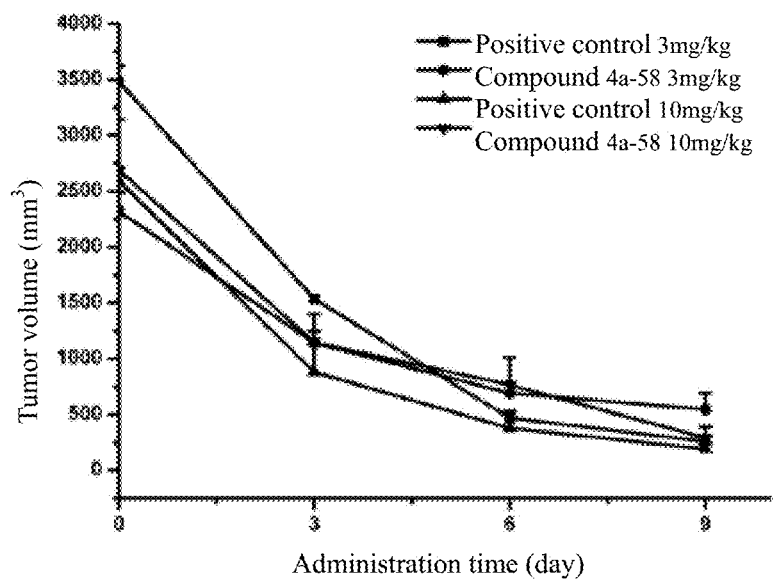
FIG. 7 shows tumor inhibition curve of compound 4a-58 in nude mice-subcutaneous human leukemia MV4-11 model.
Figure 8:
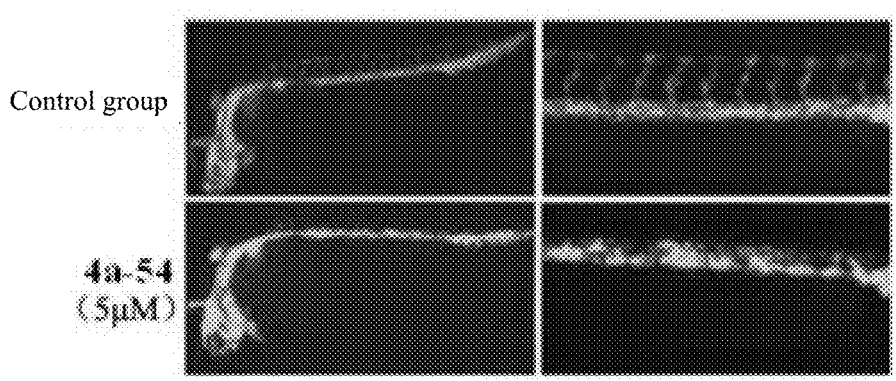
FIG. 8 shows test on angiogenesis inhibition activity of compound 4a-54 for transgenic zebrafish.

Tumor growth curves of different groups measured in the experiment are shown in FIG. 7.

Experimental results show that the test compound 4a-58 test has obvious in vivo growth inhibition effect on the mutant human acute myeloid leukemia cell line MV4-11 of FLT3-ITD; and even through tumor volume is very large, the compound can completely inhibit tumor growth at daily dose of 3 mg/kg or above. Weight loss, rash, diarrhea and other adverse reactions were not found in mice during administration, which indicates that the test compound 4a-58 has very low toxicity within the administration dosage range at the test dose.

Example 98: Test on Angiogenesis Inhibition Activity of Compound 4a-54 for Transgenic Zebrafish The purpose of the experiment was to test the inhibitory activity of the compound of the invention for new in vivo blood vessel by observing the inhibition of the compound of the invention for inter segmental vessels of transgenic zebrafish FLK1-GFP at a single concentration. The inhibitory activity of compound 4a-54 for new blood vessels was expressed by the inhibition degree of the compound for inter segmental vessel of zebrafish.

1) Experimental Materials:

Transgenic zebrafish (FLK1-GFP): cultivated by this laboratory

Experiment reagents: dimethyl sulfoxide (DMSO), test compound

Major experimental apparatus: fluorescence microscope, stereomicroscope, CCD camera, etc.

2) Experimental Method:

Acquisition of zebrafish embryos: The zebrafish used by this laboratory was fluorescent transgenic zebrafish (FLK1: GFP). Refer to Westerfield method for breeding and cultivation of zebrafish. The day before spawns were obtained, male and female zebrafish were paired at a ratio of 1:1. On the second day, the male and female zebrafish naturally mated and spawned at a temperature of about 28° C. under sufficient illumination. Enough zebrafish embryos were collected, washed, placed into embryo culture media, and put into a 28° C. incubator for culture. The survival of embryos was identified by morphological and phylogenetic standards, and dead embryos were white and taken out timely to prevent deterioration of water quality.

Medication: Ten hours after zebrafish embryos were fertilized (a microscopy was used to observe the process that the zebrafish embryos developed to bud period), healthy embryos were selected at random for grouping, a 24-well plate was added with 6 zebrafish embryos in each well, all culture media were removed by sucking, and compound solutions at different concentrations were added; a blank control was set without addition of any compound, and then the blank control was put into a 28° C. incubator for culture.

Result observation: Thirty one hours after the zebrafish embryos were fertilized, spawns were taken out and hatched zebrafish was peeled off, and then the hatched zebrafish was put onto slide, 1‰ tricaine solution was added to narcotize the fish body, and 1.5% methylcellulose was used to fix the fish body; and the inter segmental vessels (ISV) was observed, counted and photographed under a fluorescence microscope.

3) Experimental Results:

FIG. 6 shows the angiogenesis inhibition of compound 4a-54 for FLK1 transgenic zebrafish at a concentration of 5 μm. The compound 4a-54 at a concentration of 5 μm, compared with the blank control group, can completely inhibit angiogenesis of zebrafish.

Experimental results show that the compound prepared in the example of the invention has very good inhibitory activity for new blood vessels of FLK1 transgenic zebrafish.

Structural formulae of specific compounds involved in the examples of the invention are as follows:

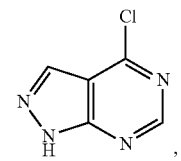

2

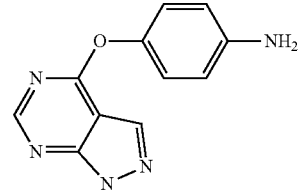

3a-1

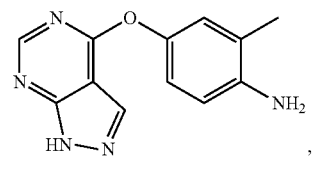

3a-2

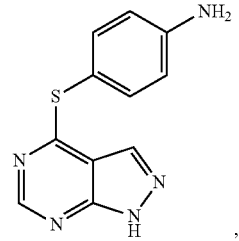

3c-3

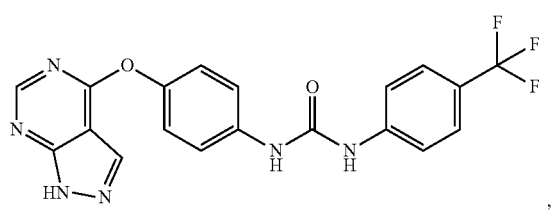

4a-1

4a-2 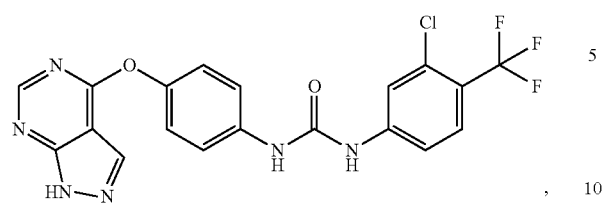
4a-3 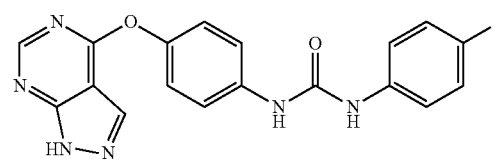
4a-4 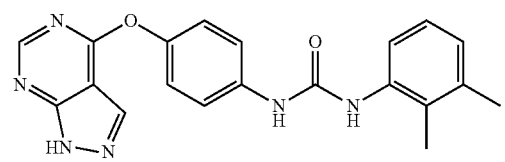
4a-5 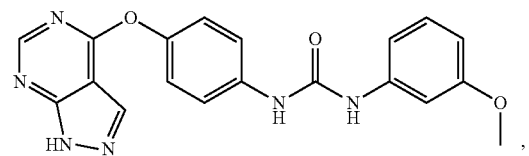
4a-6 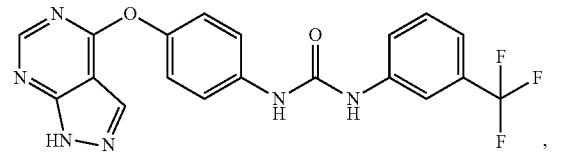
4a-7 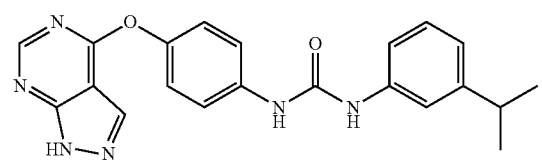
4a-8 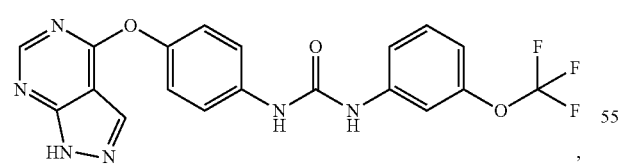
4a-9
4a-10 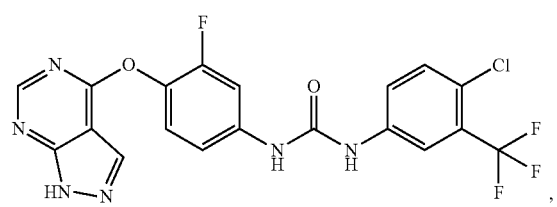
4a-11 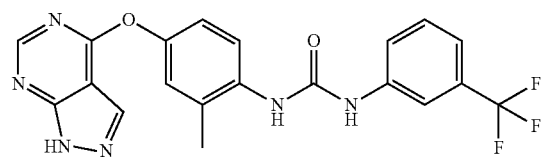
4a-12 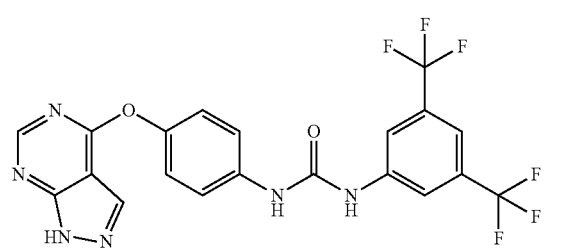
4a-13 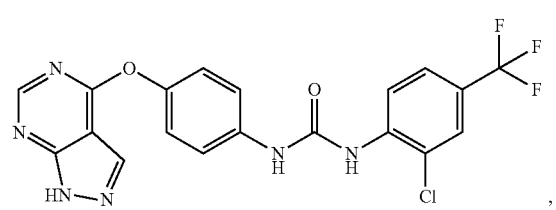
4a-14 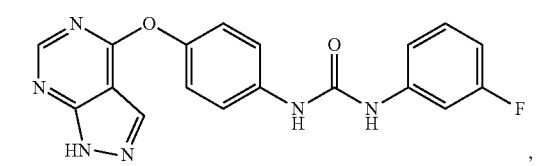
4a-15 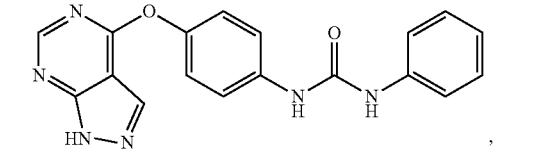
4a-16 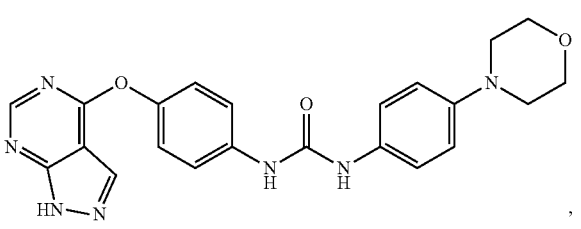

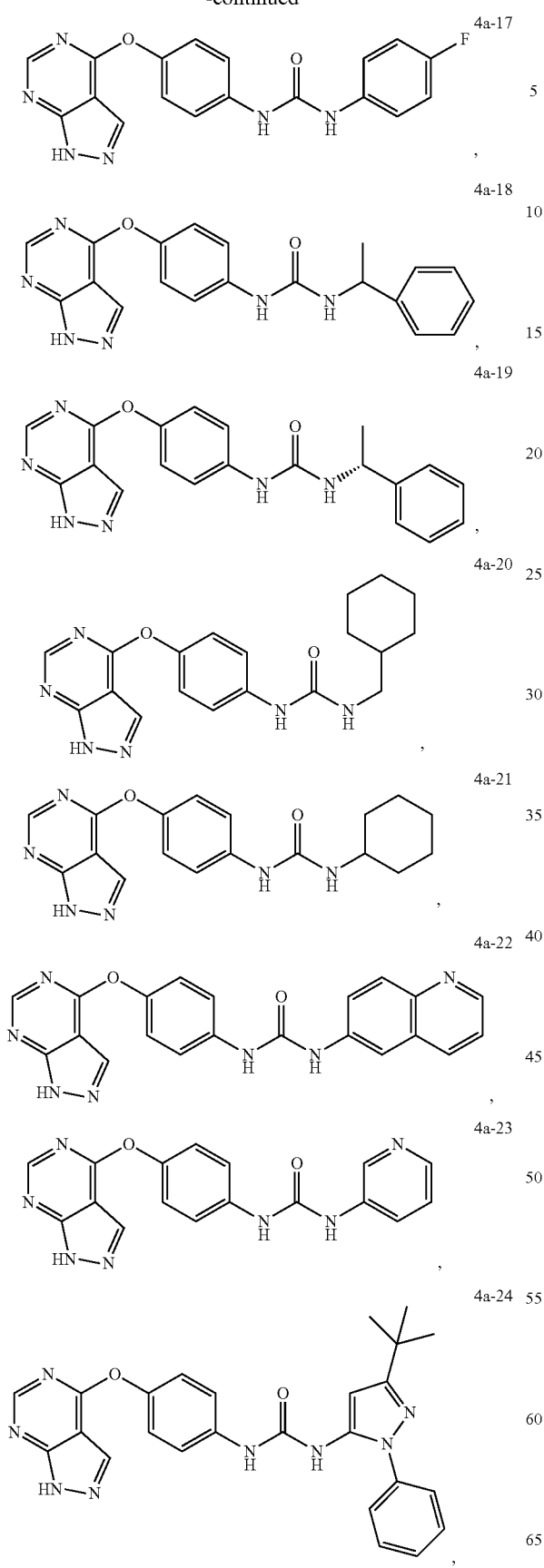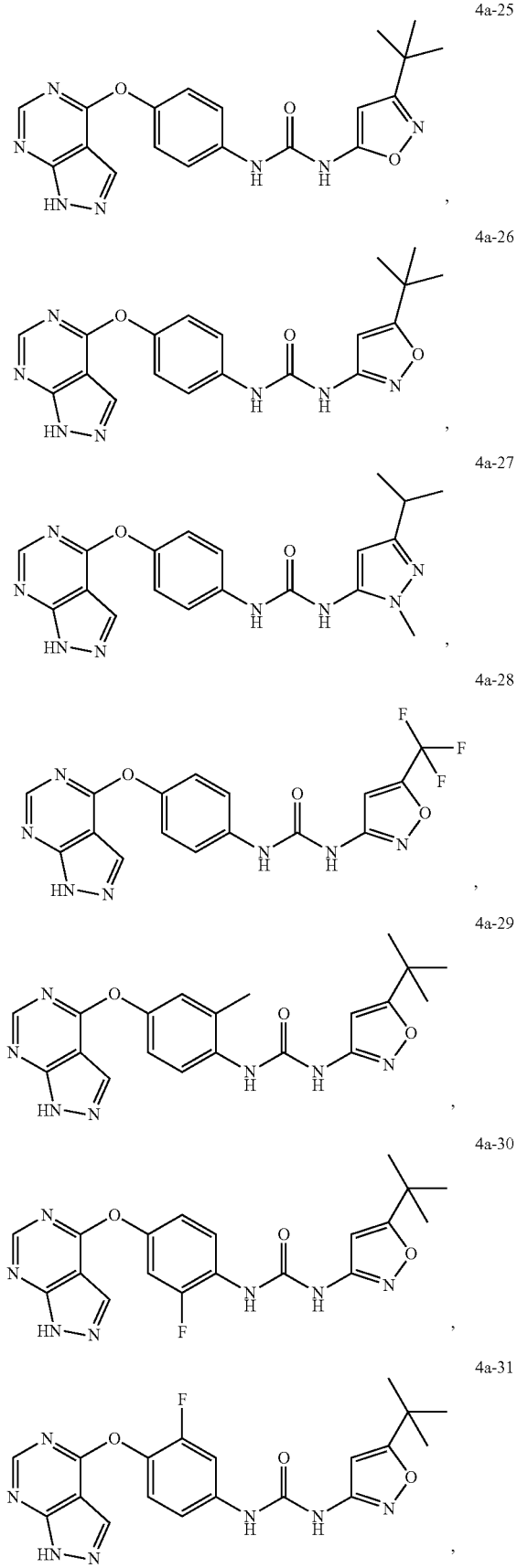

-continued
4a-32
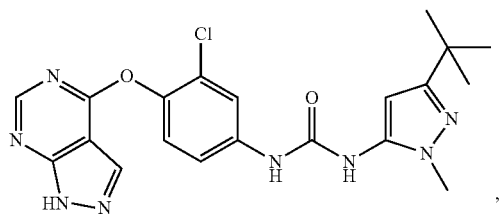
4a-33
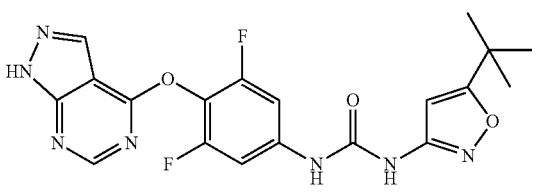
4a-34
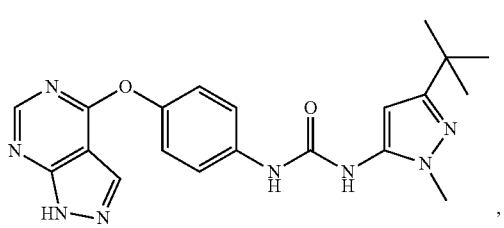
4a-35
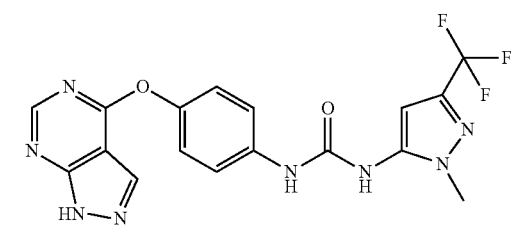
4a-36
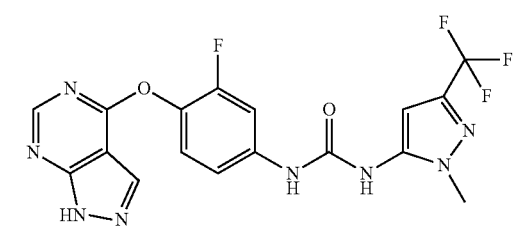
4a-37
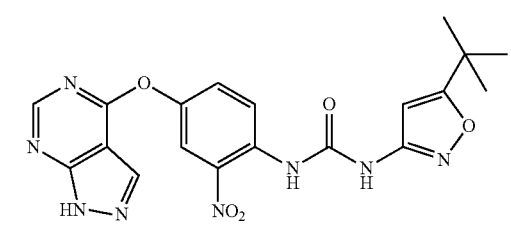
4a-38
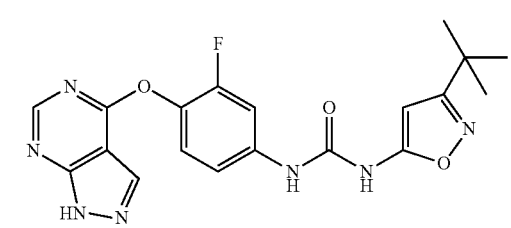
-continued
4a-39
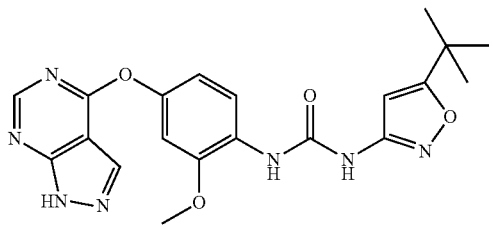
4a-40
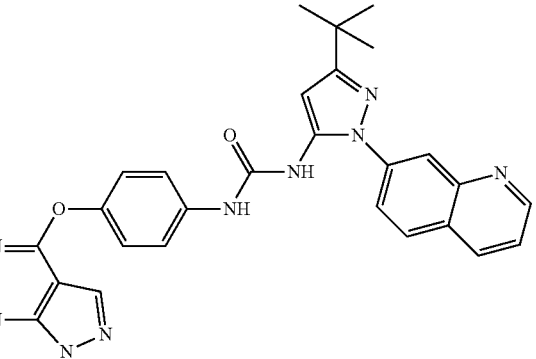
4a-41
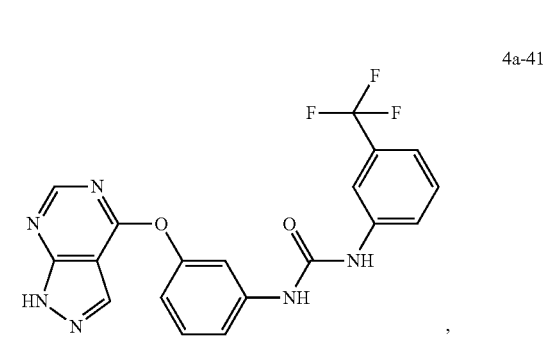
4a-42
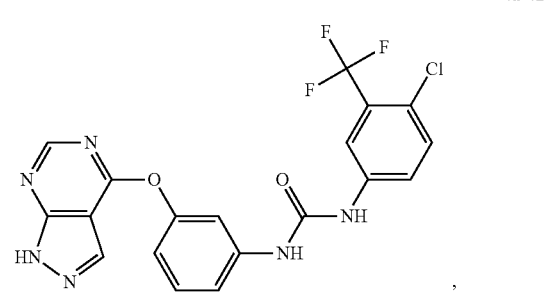
4a-43
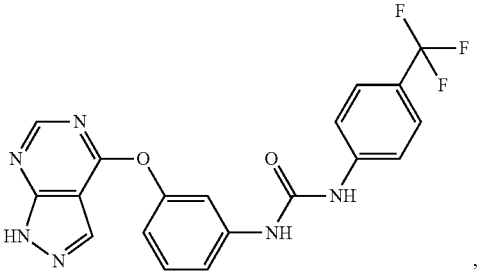

4a-44
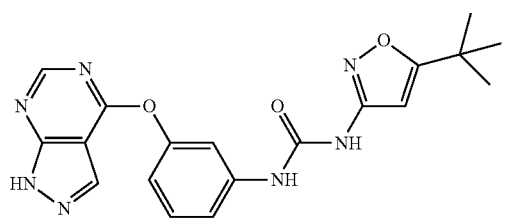
4a-45
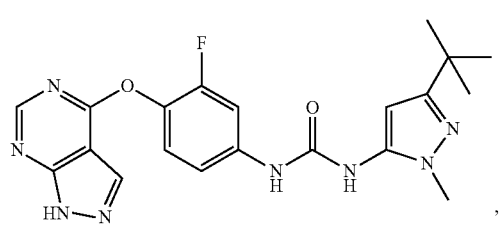
4a-46
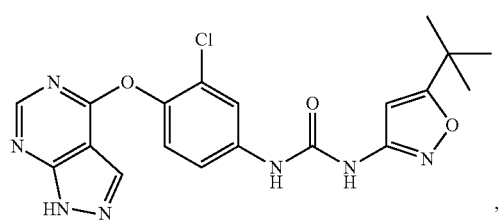
4a-47
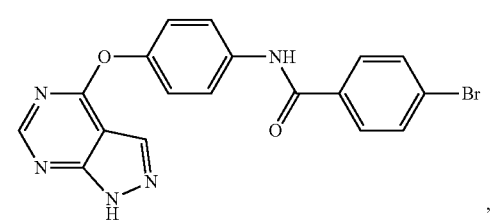
4a-48
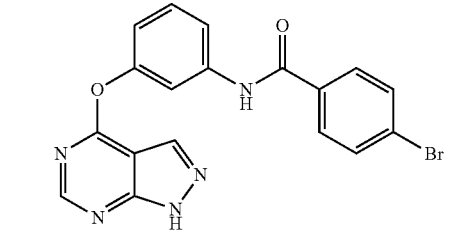
4a-49
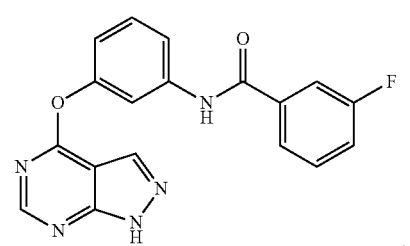
4a-50
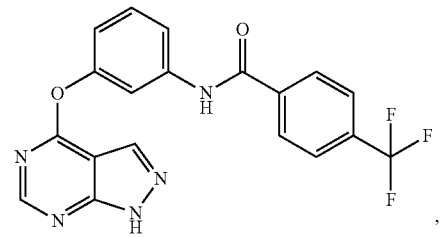
4a-51
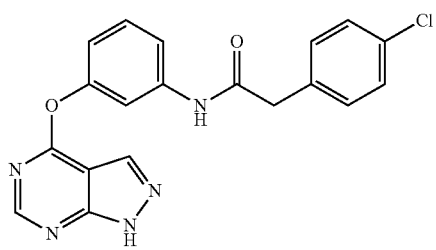
4a-52
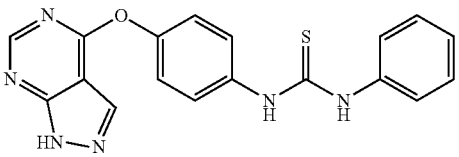
4a-53
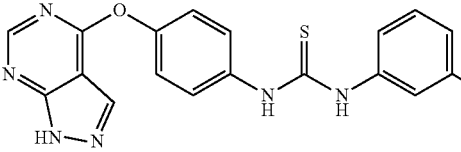
4a-54
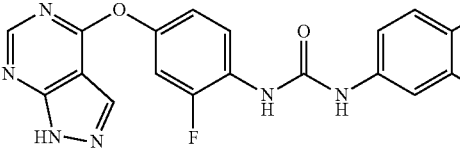
4a-55
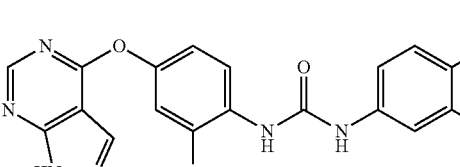
4a-56
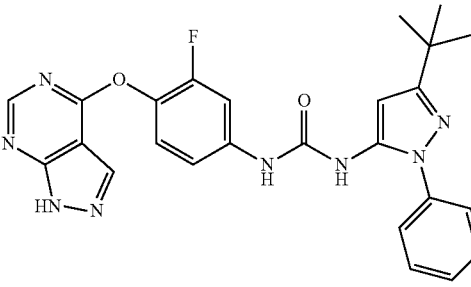

-continued
4a-57
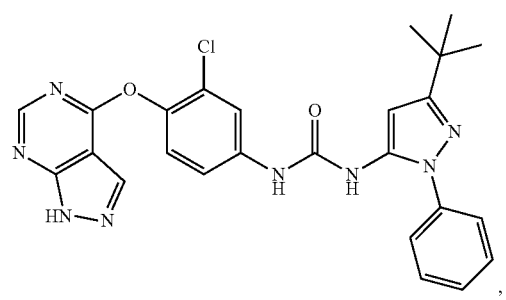
4a-58
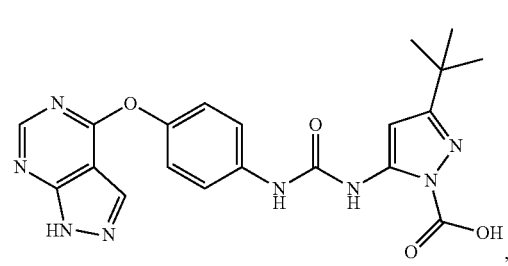
4a-59
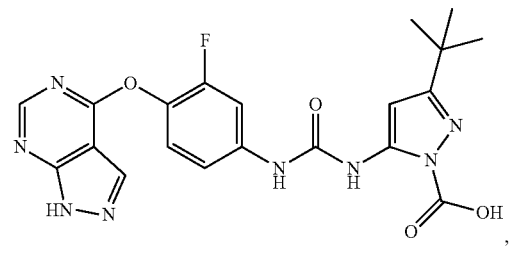
4a-60
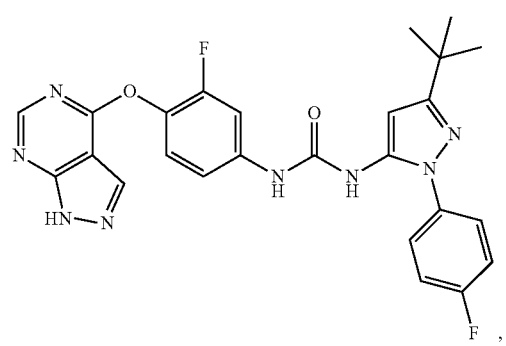
4a-61
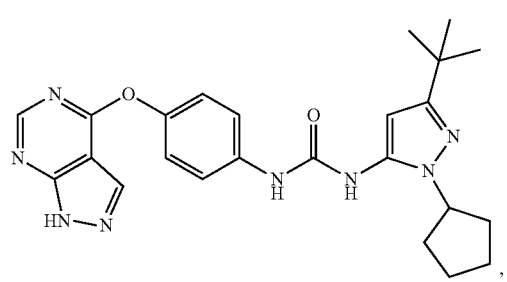
4a-62
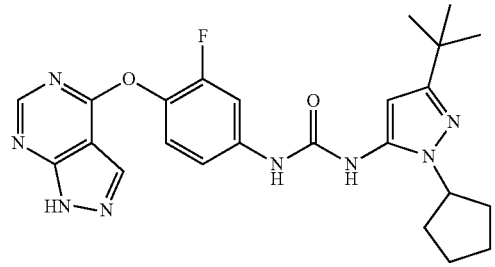
4a-63
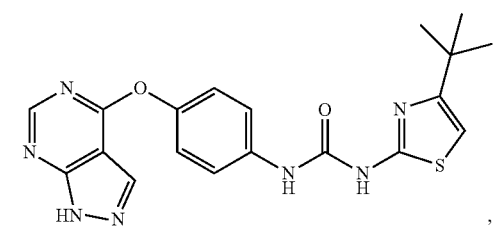
4a-64
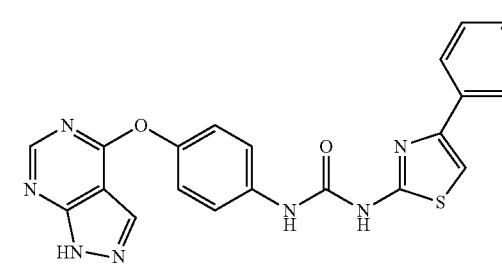
4a-65
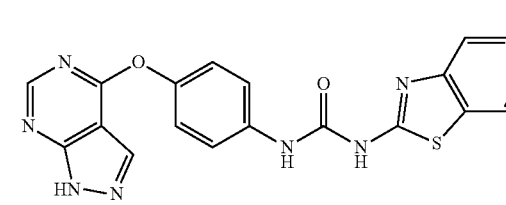
4b-1
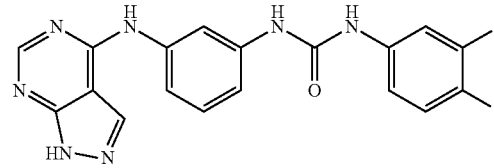
4b-2
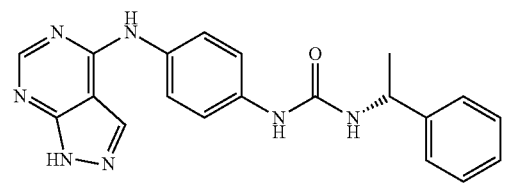
4b-3
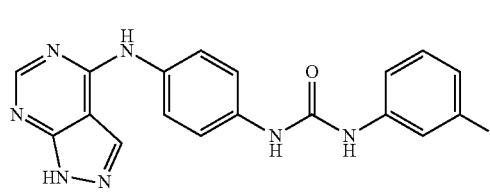

-continued 4b-4, 4b-5, 4b-6, 4b-7, 4b-8, 4c-1, 4c-2, 4c-3, 5a-1, 5a-2, 5a-3, 5a-4

The invention claimed is:

1. A pyrazolopyrimidine derivative of structural formula I:

or a pharmaceutically acceptable salt or hydrate thereof;
wherein, Y is oxygen or sulfur;
L is substituted at 3-position or 4-position on the benzene ring, wherein one end of atom N is connected with the benzene ring;

$R_1$ is —H, $C_1$-$C_6$ alkyl, or substituted 6-10 membered aromatic ring substituted methyl; and the substituent of the substituted aromatic ring is —H, halogen or $C_1$-$C_4$ alkyl;

$R_2$ is —H, halogen, $C_1$-$C_4$ alkyl, $C_1$-$C_4$ alkoxy, $C_1$-$C_4$ alkyl sulfenyl or —NO$_2$;

R₃ is substituted 4-12 membered aromatic heterocyclic radical,

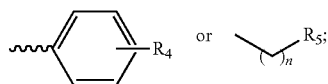

the number of heteroatoms on the substituted aromatic heterocyclic radical is 1 to 4, the heteroatom is N, O or S; the substituent on the substituted 4-12 membered aromatic heterocyclic radical is —H, $C_1$-$C_6$ alkyl, substituted or unsubstituted aryl, —$CF_3$, 5-10 membered aromatic heterocyclic radical, carboxyl or $C_3$-$C_6$ cycloalkyl; and the substituent on the substituted aryl is halogen;

R₄ is —H, halogen, $C_1$-$C_4$ alkyl, $C_1$-$C_4$ alkoxy, —$CF_3$, —$OCF_3$, morpholinyl or $C_1$-$C_4$ phenylalkyl;

R₅ is —H, aryl or $C_3$-$C_8$ cycloalkyl; and wherein when L is

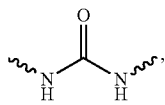

and R₃ is

then R₅ is aryl or $C_3$-$C_8$ cycloalkyl;

wherein when L is

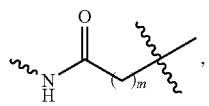

then R₃ is substituted 4-12 membered aromatic heterocyclic radical or

and R₅ is aryl or $C_3$-$C_8$ cycloalkyl;

m=0-2; and n=0-4.

2. The pyrazolopyrimidine derivative or a pharmaceutically acceptable salt or hydrate thereof of claim 1, characterized in that: Y is oxygen or sulfur;

L is

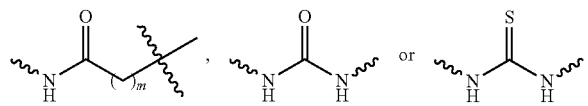

substituted at 3-position or 4-position on the benzene ring, wherein one end of atom N is connected with the benzene ring;

R₁ is —H, $C_1$-$C_6$ alkyl,

or substituted 6-10 membered aromatic ring substituted methyl; and the substituent of the substituted aromatic ring is —H, halogen or $C_1$-$C_4$ alkyl;

R₂ is —H, halogen, $C_1$-$C_4$ alkyl, $C_1$-$C_4$ alkoxy, $C_1$-$C_4$ alkyl sulfenyl or —$NO_2$;

R₃ is substituted 4-12 membered aromatic heterocyclic radical,

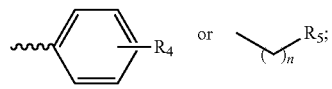

the substituent on the substituted 4-12 membered aromatic heterocyclic radical is —H, $C_1$-$C_6$ alkyl, unsubstituted aryl, —$CF_3$ or 5-10 membered aromatic heterocyclic radical; and the number of heteroatoms on the substituted 4-12 membered aromatic heterocyclic radical is 1 to 4, and the heteroatom is N, O or S;

R₄ is —H, halogen, $C_1$-$C_4$ alkyl, $C_1$-$C_4$ alkoxy, —$CF_3$, —$OCF_3$, morpholinyl or $C_1$-$C_4$ phenylalkyl;

R₅ is —H, aryl or $C_3$-$C_8$ cycloalkyl; and wherein when L is

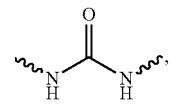

and R₃ is

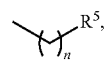

then R₅ is aryl or $C_3$-$C_8$ cycloalkyl;

wherein when L is

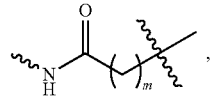

then R₃ is substituted 4-12 membered aromatic heterocyclic radical or

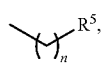

and $R_5$ is aryl or $C_3$-$C_8$ cycloalkyl;
m=0-2; and n=0-4.

3. The pyrazolopyrimidine derivative or a pharmaceutically acceptable salt or hydrate thereof of claim 2, characterized in that: Y is oxygen or sulfur;

L is

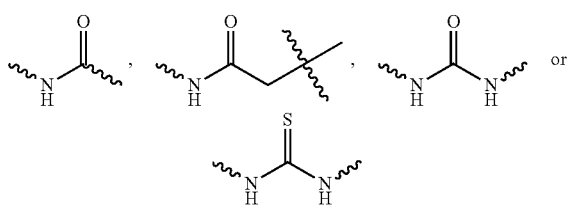

substituted at 3-position or 4-position on the benzene ring, wherein one end of atom N is connected with the benzene ring;

$R_1$ is —H, $C_1$-$C_4$ alkyl,

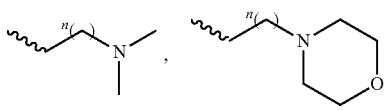

or substituted 6-10 membered aromatic ring substituted methyl; and the substituent of the substituted aromatic ring is —H, halogen or $C_1$-$C_4$ alkyl;

$R_2$ is —H, halogen, $C_1$-$C_4$ alkyl, $C_1$-$C_4$ alkoxy, $C_1$-$C_4$ alkyl sulfenyl or —NO$_2$;

$R_3$ is substituted 4-12 membered aromatic heterocyclic radical,

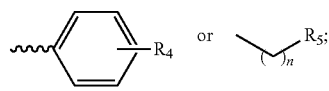

the substituent on the substituted 4-12 membered aromatic heterocyclic radical is —H, $C_1$-$C_6$ alkyl, unsubstituted aryl, —CF$_3$ or 5-10 membered aromatic heterocyclic radical; and the number of heteroatoms on the substituted 4-12 membered aromatic heterocyclic radical is 1 to 4, and the heteroatom is N, O or S;

$R_4$ is —H, halogen, $C_1$-$C_4$ alkyl, $C_1$-$C_4$ alkoxy, —CF$_3$, —OCF$_3$, morpholinyl or $C_1$-$C_4$ phenylalkyl;

$R_5$ is —H, aryl or $C_3$-$C_8$ cycloalkyl; and wherein when L is

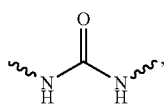

and $R_3$ is

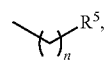

then $R_5$ is aryl or $C_3$-$C_8$ cycloalkyl;
wherein when L is

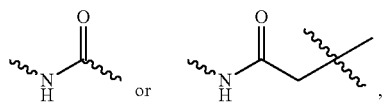

then $R_3$ is substituted 4-12 membered aromatic heterocyclic radical or

and $R_5$ is aryl or $C_3$-$C_8$ cycloalkyl;
n=0-4.

4. The pyrazolopyrimidine derivative or a pharmaceutically acceptable salt or hydrate thereof of claim 3, characterized in that: Y is oxygen or sulfur;

L is

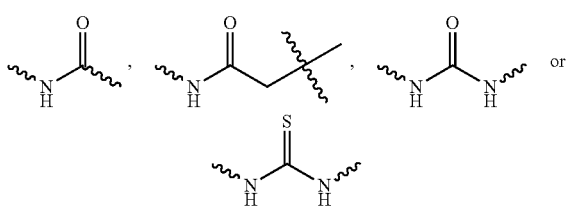

substituted at 3-position or 4-position on the benzene ring, wherein one end of atom N is connected with the benzene ring;

$R_1$ is —H, $C_1$-$C_4$ alkyl,

or substituted 6-10 membered aromatic ring substituted methyl; and the substituent of the substituted aromatic ring is —H, halogen or $C_1$-$C_4$ alkyl;

$R_2$ is —H, halogen, $C_1$-$C_4$ alkyl, $C_1$-$C_4$ alkoxy or —NO$_2$;

$R_3$ is substituted 4-12 membered aromatic heterocyclic radical,

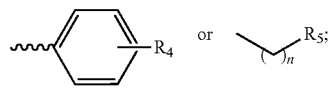

the substituent on the substituted 4-12 membered aromatic heterocyclic radical is —H, $C_1$-$C_6$ alkyl, unsubstituted aryl, —CF$_3$ or 5-10 membered aromatic heterocyclic radical; and the number of heteroatoms on the substituted 4-12 membered aromatic heterocyclic radical is 1 to 4, and the heteroatom is N, O or S;

R$_4$ is —H, halogen, C$_1$-C$_4$ alkyl, C$_1$-C$_4$ alkoxy, —CF$_3$, —OCF$_3$, morpholinyl or C$_1$-C$_4$ phenylalkyl;

R$_5$ is H, aryl or C$_3$-C$_8$ cycloalkyl; and wherein when L is

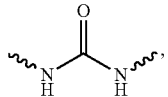

and R$_3$ is

then R$_5$ is aryl or C$_3$-C$_8$ cycloalkyl;

wherein when L is

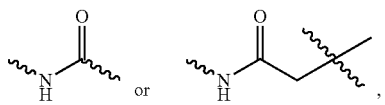

then R$_3$ is substituted 4-12 membered aromatic heterocyclic radical or

and R$_5$ is aryl or C$_3$-C$_8$ cycloalkyl;

n=0-4.

5. The pyrazolopyrimidine derivative or a pharmaceutically acceptable salt or hydrate thereof of claim 4, characterized in that: Y is oxygen or sulfur;

L is

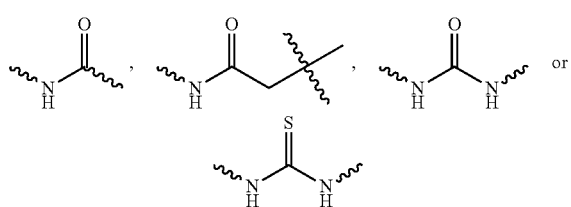

substituted at 3-position or 4-position on the benzene ring, wherein one end of atom N is connected with the benzene ring;

R$_1$ is —H, C$_1$-C$_4$ alkyl,

or substituted phenyl substituted methyl; and the substituent of the substituted phenyl is —H, halogen or C$_1$-C$_4$ alkyl;

R$_2$ is —H, halogen, C$_1$-C$_4$ alkyl, C$_1$-C$_4$ alkoxy or —NO$_2$;

R$_3$ is substituted 4-12 membered aromatic heterocyclic radical,

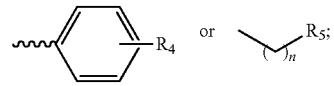

the substituent on the substituted 4-12 membered aromatic heterocyclic radical is —H, C$_1$-C$_6$ alkyl, unsubstituted aryl, —CF$_3$ or 5-10 membered aromatic heterocyclic radical; and the number of heteroatoms on the substituted 4-12 membered aromatic heterocyclic radical is 1 to 4, and the heteroatom is N, O or S;

R$_4$ is —H, halogen, C$_1$-C$_4$ alkyl, C$_1$-C$_4$ alkoxy, —CF$_3$, —OCF$_3$, morpholinyl or C$_1$-C$_4$ phenylalkyl;

R$_5$ is —H, aryl or C$_3$-C$_8$ cycloalkyl; and wherein when L is

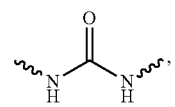

and R$_3$ is

then R$_5$ is aryl or C$_3$-C$_8$ cycloalkyl;

wherein when L is

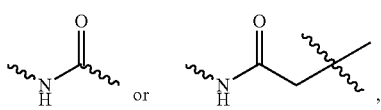

then R$_3$ is substituted 4-12 membered aromatic heterocyclic radical or

and R$_5$ is aryl or C$_3$-C$_8$ cycloalkyl;

n=0-3.

6. The pyrazolopyrimidine derivative or a pharmaceutically acceptable salt or hydrate thereof of claim 5, characterized in that: Y is oxygen or sulfur;

L is

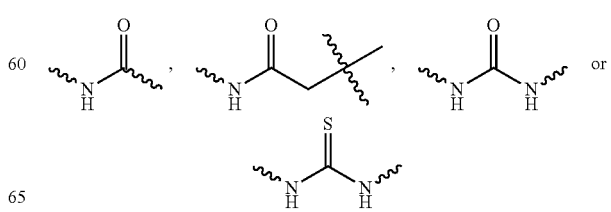

substitute at 3-position or 4-position on the benzene ring, wherein one end of atom N is connected with the benzene ring;

R$_1$ is —H, C$_1$-C$_4$ alkyl,

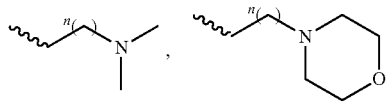

or substituted phenyl substituted methyl; and
the substituent of the substituted phenyl is —H, —F, —Cl or —Br;

R$_2$ is —H, halogen, C$_1$-C$_4$ alkyl, C$_1$-C$_4$ alkoxy or —NO$_2$;

R$_3$ is substituted 4-12 membered aromatic heterocyclic radical,

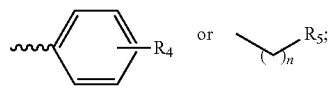

the substituent on the substituted 4-12 membered aromatic heterocyclic radical is —H, C$_1$-C$_6$ alkyl, unsubstituted aryl, —CF$_3$ or 5-10 membered aromatic heterocyclic radical; and the number of heteroatoms on the substituted 4-12 membered aromatic heterocyclic radical is 1 to 4, and the heteroatom is N, O or S;

R$_4$ is —H, halogen, C$_1$-C$_4$ alkyl, C$_1$-C$_4$ alkoxy, —CF$_3$, —OCF$_3$, morpholinyl or C$_1$-C$_4$ phenylalkyl;

R$_5$ is —H, aryl or C$_3$-C$_8$ cycloalkyl; and
wherein when L is

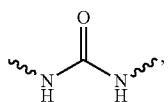

and R$_3$ is

then R$_5$ is aryl or C$_3$-C$_8$ cycloalkyl;
wherein when L is

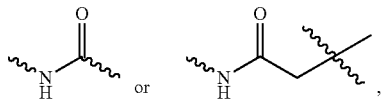

then R$_3$ is substituted 4-12 membered aromatic heterocyclic radical or

and R$_5$ is aryl or C$_3$-C$_8$ cycloalkyl;
n=0-3.

7. The pyrazolopyrimidine derivative or a pharmaceutically acceptable salt or hydrate thereof of claim 6, characterized in that: Y is oxygen or sulfur;

L is

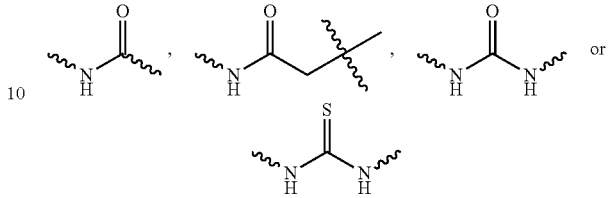

substituted at 3-position or 4-position on the benzene ring, wherein one end of atom N is connected with the benzene ring;

R$_1$ is —H, C$_1$-C$_4$ alkyl,

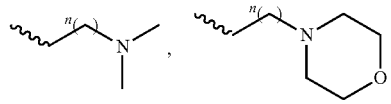

or substituted phenyl substituted methyl; and
the substituent of the substituted phenyl is —H or —Br;

R$_2$ is —H, halogen, C$_1$-C$_4$ alkyl, C$_1$-C$_4$ alkoxy or —NO$_2$;

R$_3$ is substituted 4-12 membered aromatic heterocyclic radical

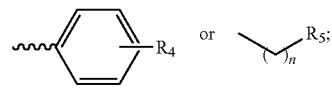

the substituent on the substituted 4-12 membered aromatic heterocyclic radical is —H, C$_1$-C$_6$ alkyl, unsubstituted aryl, —CF$_3$ or 5-10 membered aromatic heterocyclic radical; and the number of heteroatoms on the substituted 4-12 membered aromatic heterocyclic radical is 1 to 4, and the heteroatom is N, O or S;

R$_4$ is —H, halogen, C$_1$-C$_4$ alkyl, C$_1$-C$_4$ alkoxy, —CF$_3$, —OCF$_3$, morpholinyl or C$_1$-C$_4$ phenylalkyl;

R$_5$ is —H, aryl or C$_3$-C$_8$ cycloalkyl; and
wherein when L is

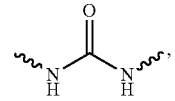

and R$_3$ is

then R$_5$ is aryl or C$_3$-C$_8$ cycloalkyl;
wherein when L is

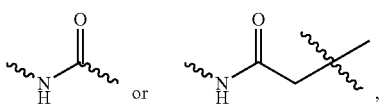

then R₃ is substituted 4-12 membered aromatic heterocyclic radical or

and R₅ is aryl or $C_3$-$C_8$ cycloalkyl;
n=0-3.

8. The pyrazolopyrimidine derivative or a pharmaceutically acceptable salt or hydrate thereof of claim 7, characterized in that: Y is oxygen or sulfur;
L is

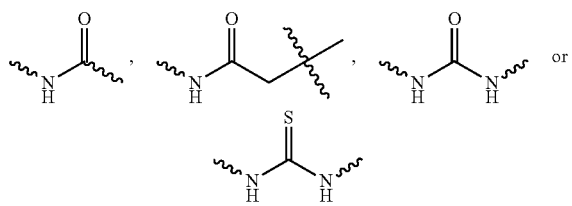

substituted at 3-position or 4-position on the benzene ring, wherein one end of atom N is connected with the benzene ring;
$R_1$ is —H, $C_1$-$C_4$ alkyl,

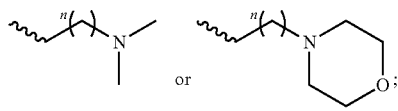

$R_2$ is —H, halogen, $C_1$-$C_4$ alkyl, $C_1$-$C_4$ alkoxy or —NO₂;
$R_3$ is substituted 4-12 membered aromatic heterocyclic radical,

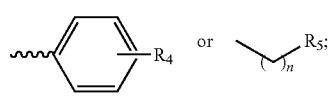

the substituent on the substituted 4-12 membered aromatic heterocyclic radical is —H, $C_1$-$C_6$ alkyl, unsubstituted aryl, —CF₃ or 5-10 membered aromatic heterocyclic radical; and the number of heteroatoms on the substituted 4-12 membered aromatic heterocyclic radical is 1 to 4, and the heteroatom is N, O or S;
$R_4$ is —H, halogen, $C_1$-$C_4$ alkyl, $C_1$-$C_4$ alkoxy, —CF₃, —OCF₃, morpholinyl or $C_1$-$C_4$ phenylalkyl;
$R_5$ is —H, aryl or $C_3$-$C_8$ cycloalkyl; and
wherein when L is

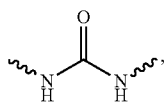

and R₃ is

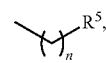

then R₅ is aryl or $C_3$-$C_8$ cycloalkyl;
wherein when L is

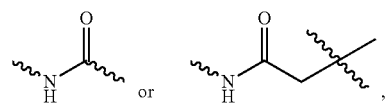

then R₃ is substituted 4-12 membered aromatic heterocyclic radical or

and R₅ is aryl or $C_3$-$C_8$ cycloalkyl;
n=0-3.

9. The pyrazolopyrimidine derivative or a pharmaceutically acceptable salt or hydrate thereof of claim 8, characterized in that: Y is oxygen or sulfur;
L is

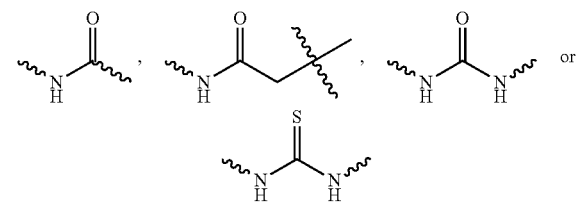

substituted at 3-position or 4-position on the benzene ring, wherein one end of atom N is connected with the benzene ring;
$R_1$ is —H,

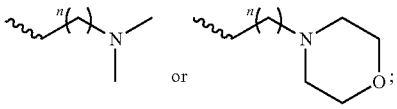

$R_2$ is —H, halogen, $C_1$-$C_4$ alkyl, $C_1$-$C_4$ alkoxy or —NO₂;
$R_3$ is substituted 4-12 membered aromatic heterocyclic radical,

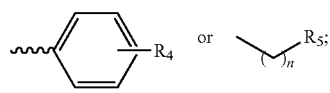

the substituent on the substituted 4-12 membered aromatic heterocyclic radical is —H, $C_1$-$C_6$ alkyl, unsubstituted aryl, —CF₃ or 5-10 membered aromatic heterocyclic radical; and the number of heteroatoms on the substituted 4-12 membered aromatic heterocyclic radical is 1 to 4, and the heteroatom is N, O or S;

R₄ is —H, halogen, $C_1$-$C_4$ alkyl, $C_1$-$C_4$ alkoxy, —CF₃, —OCF₃, morpholinyl or $C_1$-$C_4$ phenylalkyl;
R₅ is —H, aryl or $C_3$-$C_8$ cycloalkyl; and
wherein when L is

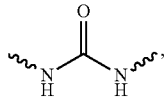

and R₃ is

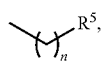

then R₅ is aryl or $C_3$-$C_8$ cycloalkyl;
wherein when L is

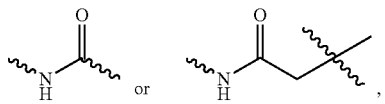

then R₃ is substituted 4-12 membered aromatic heterocyclic radical or

and R₅ is aryl or $C_3$-$C_8$ cycloalkyl;
n=0-3.

10. The pyrazolopyrimidine derivative or a pharmaceutically acceptable salt or hydrate thereof of claim 9, characterized in that: Y is oxygen or sulfur;
L is

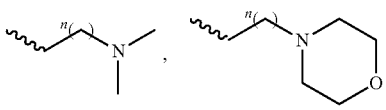

substituted at 3-position or 4-position on the benzene ring, wherein one end of atom N is connected with the benzene ring;
R₁ is —H;
R₂ is —H, halogen, $C_1$-$C_4$ alkyl, $C_1$-$C_4$ alkoxy or —NO₂;
R₃ is substituted 4-12 membered aromatic heterocyclic radical,

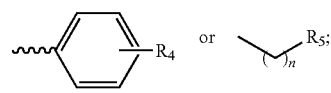

the substituent on the substituted 4-12 membered aromatic heterocyclic radical is —H, $C_1$-$C_6$ alkyl, unsubstituted aryl, —CF₃ or 5-10 membered aromatic heterocyclic radical; and the number of heteroatoms on the substituted 4-12 membered aromatic heterocyclic radical is 1 to 4, and the heteroatom is N, O or S;

R₄ is —H, halogen, $C_1$-$C_4$ alkyl, $C_1$-$C_4$ alkoxy, —CF₃, —OCF₃, morpholinyl or $C_1$-$C_4$ phenylalkyl;
R₅ is —H, aryl or $C_3$-$C_8$ cycloalkyl; and
wherein when L is

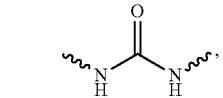

and R₃ is

then R₅ is aryl or $C_3$-$C_8$ cycloalkyl;
wherein when L is

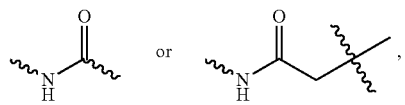

then R₃ is substituted 4-12 membered aromatic heterocyclic radical or

and R₅ is aryl or $C_3$-$C_8$ cycloalkyl;
n=0-3.

11. The pyrazolopyrimidine derivative or a pharmaceutically acceptable salt or hydrate thereof of claim 3, characterized in that: Y is oxygen or sulfur;
L is

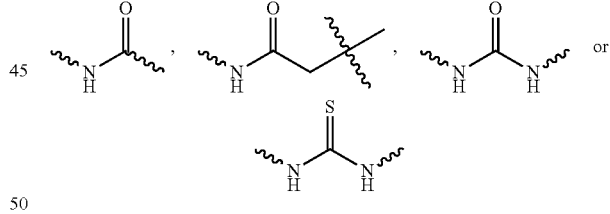

substituted at 3-position or 4-position on the benzene ring, wherein one end of atom N is connected with the benzene ring;
R₁ is —H, $C_1$-$C_4$ alkyl,

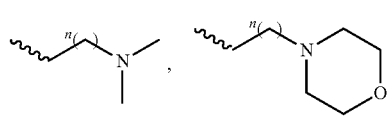

or substituted phenyl substituted methyl; and
the substituent of the substituted phenyl is —H, halogen or $C_1$-$C_4$ alkyl;
R₂ is —H, —F, —Cl, —Br, $C_1$-$C_4$ alkyl, $C_1$-$C_4$ alkoxy or —NO₂;

R$_3$ is substituted 4-12 membered aromatic heterocyclic radical,

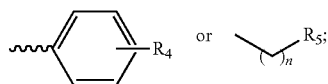

the substituent on the substituted 4-12 membered aromatic heterocyclic radical is —H, C$_1$-C$_6$ alkyl, unsubstituted aryl, —CF$_3$ or 5-10 membered aromatic heterocyclic radical; and the number of heteroatoms on the substituted 4-12 membered aromatic heterocyclic radical is 1 to 4, and the heteroatom is N, O or S;

R$_4$ is —H, halogen, C$_1$-C$_4$ alkyl, C$_1$-C$_4$ alkoxy, —CF$_3$, —OCF$_3$, morpholinyl or C$_1$-C$_4$ phenylalkyl;

R$_5$ is —H, aryl or C$_3$-C$_8$ cycloalkyl; and wherein when L is

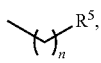

and R$_3$ is

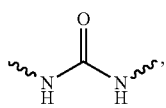

then R$_5$ is aryl or C$_3$-C$_8$ cycloalkyl;

wherein when L is

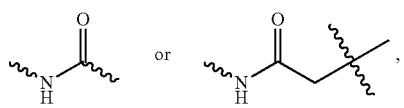

then R$_3$ is substituted 4-12 membered aromatic heterocyclic radical or

and R$_5$ is aryl or C$_3$-C$_8$ cycloalkyl;

n=0-4.

12. The pyrazolopyrimidine derivative or a pharmaceutically acceptable salt or hydrate thereof of claim 11, characterized in that: Y is oxygen or sulfur;

L is

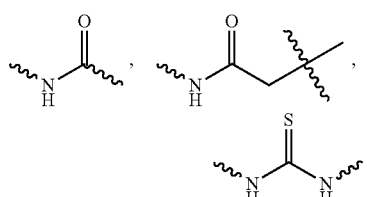

substituted at 3-position or 4-position on the benzene ring, wherein one end of atom N is connected with the benzene ring;

R$_1$ is —H, C$_1$-C$_4$ alkyl,

or substituted phenyl substituted methyl; and the substituent of the substituted phenyl is —H, halogen or C$_1$-C$_4$ alkyl;

R$_2$ is —H, —F, —Cl, C$_1$-C$_4$ alkyl, C$_1$-C$_4$ alkoxy or —NO$_2$;

R$_3$ is substituted 4-12 membered aromatic heterocyclic radical,

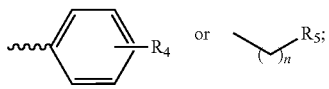

the substituent on the substituted 4-12 membered aromatic heterocyclic radical is —H, C$_1$-C$_6$ alkyl, unsubstituted aryl, —CF$_3$ or 5-10 membered aromatic heterocyclic radical; and the number of heteroatoms on the substituted 4-12 membered aromatic heterocyclic radical is 1 to 4, and the heteroatom is N, O or S;

R$_4$ is —H, halogen, C$_1$-C$_4$ alkyl, C$_1$-C$_4$ alkoxy, —CF$_3$, —OCF$_3$, morpholinyl or C$_1$-C$_4$ phenylalkyl;

R$_5$ is H, aryl or C$_3$-C$_8$ cycloalkyl; and wherein when L is

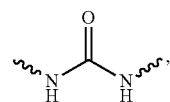

and R$_3$ is

then R$_5$ is aryl or C$_3$-C$_8$ cycloalkyl;

wherein when L is

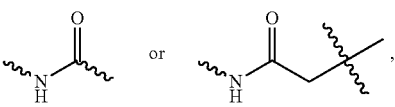

then R$_3$ is substituted 4-12 membered aromatic heterocyclic radical or

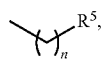

and R$_5$ is aryl or C$_3$-C$_8$ cycloalkyl;

n=0-4.

13. The pyrazolopyrimidine derivative or a pharmaceutically acceptable salt or hydrate thereof of claim 12, characterized in that: Y is oxygen or sulfur;

L is

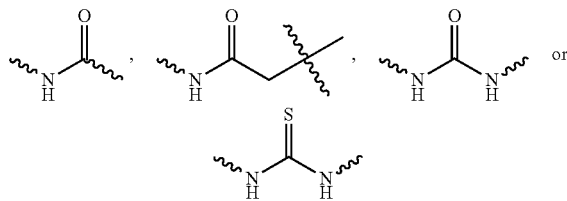

substituted at 3-position or 4-position on the benzene ring, wherein one end of atom N is connected with the benzene ring;

$R_1$ is —H, $C_1$-$C_4$ alkyl,

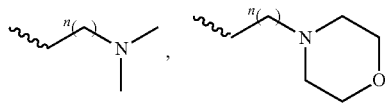

or substituted phenyl substituted methyl; and
    the substituent of the substituted phenyl is —H, halogen or $C_1$-$C_4$ alkyl;

$R_2$ is —H, —F, —Cl, methyl, methoxy or —NO$_2$;

$R_3$ is substituted 4-12 membered aromatic heterocyclic radical,

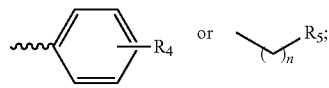

the substituent on the substituted 4-12 membered aromatic heterocyclic radical is —H, $C_1$-$C_6$ alkyl, unsubstituted aryl, —CF$_3$ or 5-10 membered aromatic heterocyclic radical; and the number of heteroatoms on the substituted 4-12 membered aromatic heterocyclic radical is 1 to 4, and the heteroatom is N, O or S;

$R_4$ is —H, halogen, $C_1$-$C_4$ alkyl, $C_1$-$C_4$ alkoxy, —CF$_3$, —OCF$_3$, morpholinyl or $C_1$-$C_4$ phenylalkyl;

$R_5$ is —H, aryl or $C_3$-$C_8$ cycloalkyl; and wherein when L is

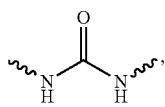

and $R_3$ is

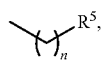

then $R_5$ is aryl or $C_3$-$C_8$ cycloalkyl;

wherein when L is

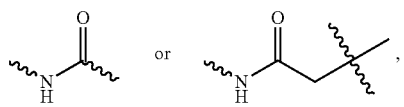

then $R_3$ is substituted 4-12 membered aromatic heterocyclic radical or

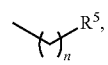

and $R_5$ is aryl or $C_3$-$C_8$ cycloalkyl;

n=0-3.

14. The pyrazolopyrimidine derivative or a pharmaceutically acceptable salt or hydrate thereof of claim 3, characterized in that: Y is oxygen or sulfur;

L is

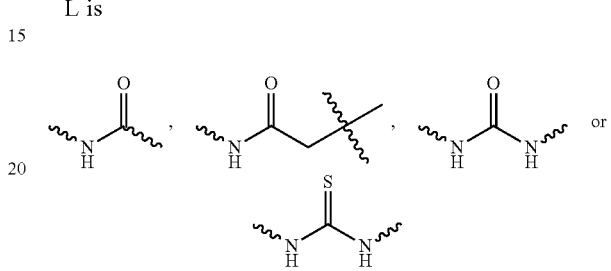

substituted at 3-position or 4-position on the benzene ring, wherein one end of atom N is connected with the benzene ring;

$R_1$ is —H, $C_1$-$C_4$ alkyl,

or substituted phenyl substituted methyl; and
    the substituent of the substituted phenyl is —H, halogen or $C_1$-$C_4$ alkyl;

$R_2$ is —H, halogen, $C_1$-$C_4$ alkyl, $C_1$-$C_4$ alkoxy or —NO$_2$;

$R_3$ is substituted 5-10 membered aromatic heterocyclic radical,

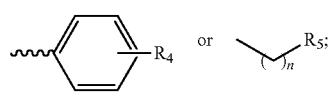

the substituent on the substituted 5-10 membered aromatic heterocyclic radical is —H, $C_1$-$C_4$ alkyl, unsubstituted aryl, —CF$_3$ or 5-10 membered aromatic heterocyclic radical; and the number of heteroatoms on the substituted 5-10 membered aromatic heterocyclic radical is 1 to 3, and the heteroatom is N or O;

$R_4$ is —H, halogen, $C_1$-$C_4$ alkyl, $C_1$-$C_4$ alkoxy, —CF$_3$, —OCF$_3$, morpholinyl or $C_1$-$C_4$ phenylalkyl;

$R_5$ is —H, aryl or $C_3$-$C_8$ cycloalkyl; and wherein when L is

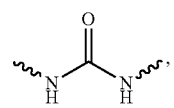

and $R_3$ is

then $R_5$ is aryl or $C_3$-$C_8$ cycloalkyl;
wherein when L is

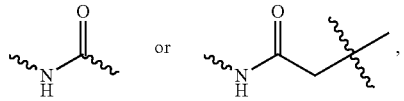

then $R_3$ is substituted 5-10 membered aromatic heterocyclic radical or

and $R_5$ is aryl or $C_3$-$C_8$ cycloalkyl;
n=0-4.

15. The pyrazolopyrimidine derivative or a pharmaceutically acceptable salt or hydrate thereof of claim 14, characterized in that: Y is oxygen or sulfur;
L is

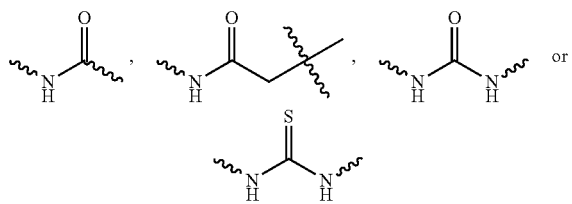

substituted at 3-position or 4-position on the benzene ring, wherein one end of atom N is connected with the benzene ring;
$R_1$ is —H, $C_1$-$C_4$ alkyl,

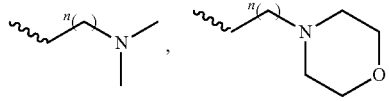

or substituted phenyl substituted methyl; and
the substituent of the substituted phenyl is —H, halogen or $C_1$-$C_4$ alkyl;
$R_2$ is —H, halogen, $C_1$-$C_4$ alkyl, $C_1$-$C_4$ alkoxy or —NO$_2$;
$R_3$ is substituted 5-10 membered aromatic heterocyclic radical,

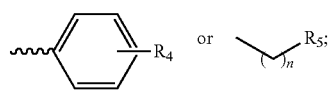

the substituent on the substituted 5-10 membered aromatic heterocyclic radical is —H, $C_1$-$C_4$ alkyl, unsubstituted aryl, —CF$_3$ or quinolyl; and the number of heteroatoms on the substituted 5-10 membered aromatic heterocyclic radical is 1 to 3, and the heteroatom is N or O;

$R_4$ is —H, halogen, $C_1$-$C_4$ alkyl, $C_1$-$C_4$ alkoxy, —CF$_3$, —OCF$_3$, morpholinyl or $C_1$-$C_4$ phenylalkyl;
$R_5$ is —H, aryl or $C_3$-$C_8$ cycloalkyl; and
wherein when L is

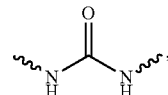

and $R_3$ is

the $R_5$ is aryl or $C_3$-$C_8$ cycloalkyl;
wherein when L is

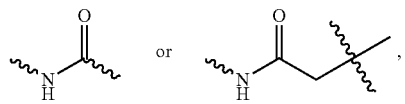

then $R_3$ is substituted 5-10 membered aromatic heterocyclic radical or

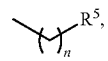

and $R_5$ is aryl or $C_3$-$C_8$ cycloalkyl;
n=0-4.

16. The pyrazolopyrimidine derivative or a pharmaceutically acceptable salt or hydrate thereof of claim 15, characterized in that: Y is oxygen or sulfur;
L is

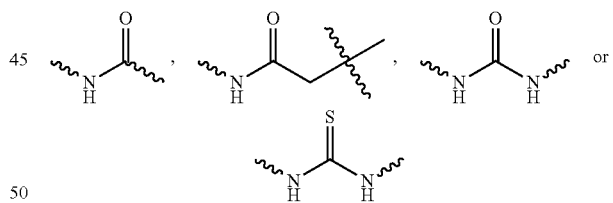

substituted at 3-position or 4-position on the benzene ring, wherein one end of atom N is connected with the benzene ring;
$R_1$ is —H, $C_1$-$C_4$ alkyl,

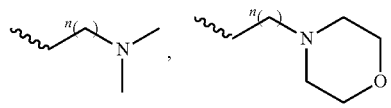

or substituted phenyl substituted methyl; and
the substituent of the substituted phenyl is —H, halogen or $C_1$-$C_4$ alkyl;
$R_2$ is —H, halogen, $C_1$-$C_4$ alkyl, $C_1$-$C_4$ alkoxy or —NO$_2$;

R₃ is substituted 5-10 membered aromatic heterocyclic radical,

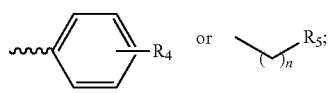

the substituent on the substituted 5-10 membered aromatic heterocyclic radical is —H, C₁-C₄ alkyl, unsubstituted phenyl, —CF₃ or quinolyl; and the number of heteroatoms on the substituted 5-10 membered aromatic heterocyclic radical is 1 to 3, and the heteroatom is N or O;
R₄ is —H, halogen, C₁-C₄ alkyl, C₁-C₄ alkoxy, —CF₃, —OCF₃, morpholinyl or C₁-C₄ phenylalkyl;
R₅ is —H, aryl or C₃-C₈ cycloalkyl; and
wherein when L is

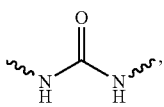

and R₃ is

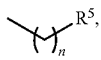

then R₅ is aryl or C₃-C₈ cycloalkyl;
wherein when L is

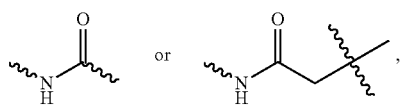

then R₃ is substituted 5-10 membered aromatic heterocyclic radical or

and R₅ is aryl or C₃-C₈ cycloalkyl;
n=0-4.

17. The pyrazolopyrimidine derivative or a pharmaceutically acceptable salt or hydrate thereof of claim 16, characterized in that: Y is oxygen or sulfur;
L is

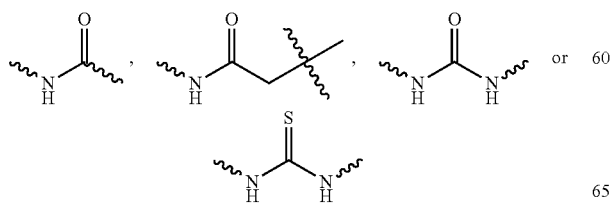

substituted at 3-position or 4-position on the benzene ring, wherein one end of atom N is connected with the benzene ring;
R₁ is —H, C₁-C₄ alkyl,

or substituted phenyl substituted methyl; and
the substituent of the substituted phenyl is —H, halogen or C₁-C₄ alkyl;
R₂ is —H, halogen, C₁-C₄ alkyl, C₁-C₄ alkoxy or —NO₂;
R₃ is substituted 5-10 membered aromatic heterocyclic radical,

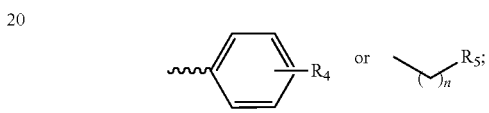

the substituent on the substituted 5-10 membered aromatic heterocyclic radical is —H, C₁-C₄ alkyl, unsubstituted phenyl, —CF₃ or quinolyl; and the number of heteroatoms on the substituted 5-10 membered aromatic heterocyclic radical is 1 to 2, and the heteroatom is N or O;
R₄ is —H, halogen, C₁-C₄ alkyl, C₁-C₄ alkoxy, —CF₃, —OCF₃, morpholinyl or C₁-C₄ phenylalkyl;
R₅ is —H, aryl or C₃-C₈ cycloalkyl; and
wherein when L is

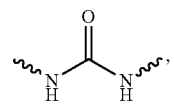

and R₃ is

then R₅ is aryl or C₃-C₈ cycloalkyl;
wherein when L is

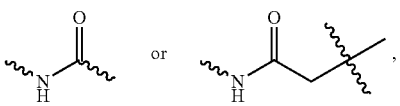

then R₃ is substituted 5-10 membered aromatic heterocyclic radical or

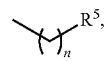

and R₅ is aryl or C₃-C₈ cycloalkyl;
n=0-3.

18. The pyrazolopyrimidine derivative or a pharmaceutically acceptable salt or hydrate thereof of claim 17, characterized in that: Y is oxygen or sulfur;

L is

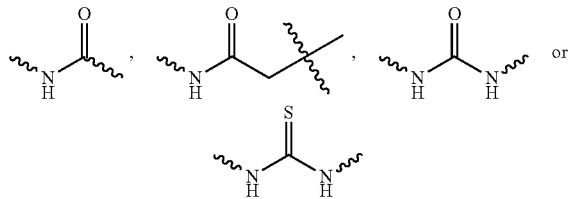

substituted at 3-position or 4-position on the benzene ring, wherein one end of atom N is connected with the benzene ring;

$R_1$ is —H, $C_1$-$C_4$ alkyl,

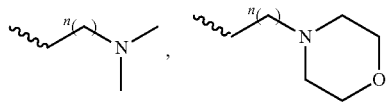

or substituted phenyl substituted methyl; and
  the substituent of the substituted phenyl is —H, halogen or $C_1$-$C_4$ alkyl;
$R_2$ is —H, halogen, $C_1$-$C_4$ alkyl, $C_1$-$C_4$ alkoxy or —$NO_2$;
$R_3$ is substituted pyrazolyl, substituted isoxazolyl, substituted quinolyl, substituted pyridyl,

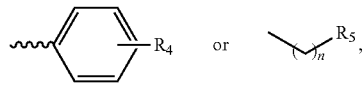

and the substituent is —H, $C_1$-$C_4$ alkyl, unsubstituted phenyl, —$CF_3$ or quinolyl;
$R_4$ is —H, halogen, $C_1$-$C_4$ alkyl, $C_1$-$C_4$ alkoxy, —$CF_3$, —$OCF_3$, morpholinyl or $C_1$-$C_4$ phenylalkyl;
$R_5$ is —H, aryl or $C_3$-$C_8$ cycloalkyl; and
wherein when L is

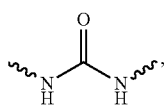

and $R_3$ is

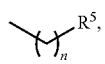

then $R_5$ is aryl or $C_3$-$C_8$ cycloalkyl;
wherein when L is

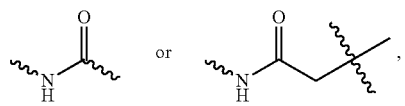

then $R_3$ is substituted pyrazolyl, substituted isoxazolyl, substituted quinolyl, substituted pyridyl, or

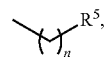

and $R_5$ is aryl or $C_3$-$C_8$ cycloalkyl;
n=0-3.

19. The pyrazolopyrimidine derivative or a pharmaceutically acceptable salt or hydrate thereof of claim 3, characterized in that: Y is oxygen or sulfur;

L is

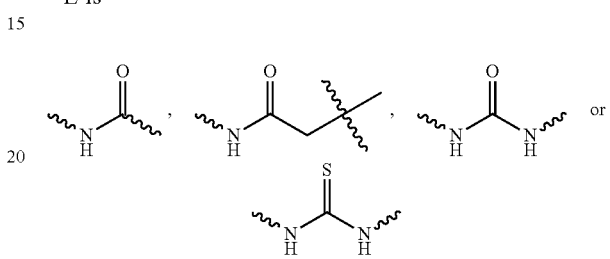

substituted at 3-position or 4-position on the benzene ring, wherein one end of atom N is connected with the benzene ring;

$R_1$ is —H, $C_1$-$C_4$ alkyl,

or substituted phenyl substituted methyl; and
  the substituent of the substituted phenyl is —H, halogen or $C_1$-$C_4$ alkyl;
$R_2$ is —H, halogen, $C_1$-$C_4$ alkyl, $C_1$-$C_4$ alkoxy or —$NO_2$;
$R_3$ is substituted 4-12 membered aromatic heterocyclic radical,

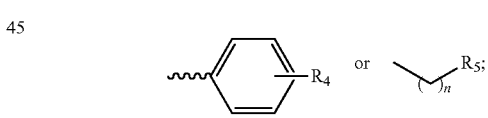

the substituent on the substituted 4-12 membered aromatic heterocyclic radical is —H, $C_1$-$C_6$ alkyl, unsubstituted aryl, —$CF_3$ or 5-10 membered aromatic heterocyclic radical; and the number of heteroatoms on the substituted 4-12 membered aromatic heterocyclic radical is 1 to 4, and the heteroatom is N or O;
$R_4$ is —H, halogen, $C_1$-$C_4$ alkyl, $C_1$-$C_4$ alkoxy, —$CF_3$, —$OCF_3$ or morpholinyl;
$R_5$ is —H, aryl or $C_3$-$C_8$ cycloalkyl; and
wherein when L is

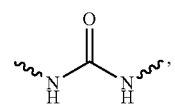

and R₃ is

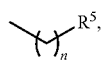

then R₅ is aryl or $C_3$-$C_8$ cycloalkyl;
wherein when L is

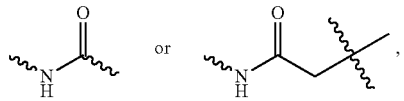

then R₃ is substituted 4-12 membered aromatic heterocyclic radical or

and R₅ is aryl or $C_3$-$C_8$ cycloalkyl;
n=0-4.

20. The pyrazolopyrimidine derivative or a pharmaceutically acceptable salt or hydrate thereof of claim 19, characterized in that: Y is oxygen or sulfur;
L is

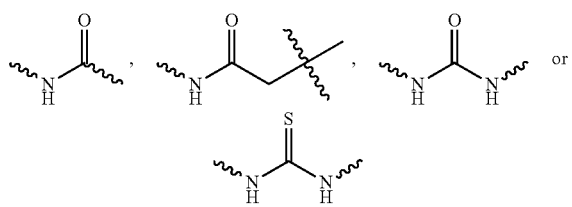

substituted at 3-position or 4-position on the benzene ring, wherein one end of atom N is connected with the benzene ring;
R₁ is —H, $C_1$-$C_4$ alkyl,

or substituted phenyl substituted methyl; and
the substituent of the substituted phenyl is —H, halogen or $C_1$-$C_4$ alkyl;
R₂ is —H, halogen, $C_1$-$C_4$ alkyl, $C_1$-$C_4$ alkoxy or —NO₂;
R₃ is substituted 4-12 membered aromatic heterocyclic radical,

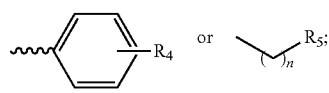

the substituent on the substituted 4-12 membered aromatic heterocyclic radical is —H, $C_1$-$C_6$ alkyl, unsubstituted aryl, —CF₃ or 5-10 membered aromatic heterocyclic radical; and the number of heteroatoms on the substituted 4-12 membered aromatic heterocyclic radical is 1 to 4, and the heteroatom is N or O;

R₄ is —H, —F, —Cl, —Br, $C_1$-$C_4$ alkyl, $C_1$-$C_4$ alkoxy, —CF₃, —OCF₃ or morpholinyl;
R₅ is —H, aryl or $C_3$-$C_8$ cycloalkyl; and
wherein when L is

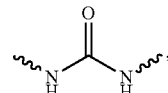

and R₃ is

then R₅ is aryl or $C_3$-$C_8$ cycloalkyl;
wherein when L is

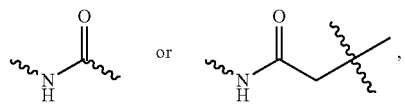

then R₃ is substituted 4-12 membered aromatic heterocyclic radical or

and R₅ is aryl or $C_3$-$C_8$ cycloalkyl;
n=0-4.

21. The pyrazolopyrimidine derivative or a pharmaceutically acceptable salt or hydrate thereof of claim 20, characterized in that: Y is oxygen or sulfur;
L is

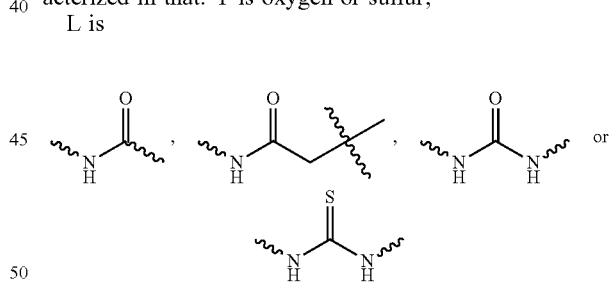

substituted at 3-position or 4-position on the benzene ring, wherein one end of atom N is connected with the benzene ring;
R₁ is —H, $C_1$-$C_4$ alkyl,

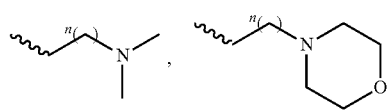

or substituted phenyl substituted methyl; and
the substituent of the substituted phenyl is —H, halogen or $C_1$-$C_4$ alkyl;
R₂ is —H, halogen, $C_1$-$C_4$ alkyl, $C_1$-$C_4$ alkoxy or —NO₂;

R₃ is substituted 4-12 membered aromatic heterocyclic radical,

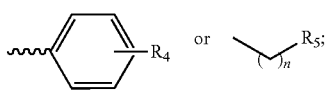

the substituent on the substituted 4-12 membered aromatic heterocyclic radical is —H, $C_1$-$C_6$ alkyl, unsubstituted aryl, —$CF_3$ or 5-10 membered aromatic heterocyclic radical; and the number of heteroatoms on the substituted 4-12 membered aromatic heterocyclic radical is 1 to 4, and the heteroatom is N or O;

$R_4$ is —H, —F, —Cl, —Br, $C_1$-$C_4$ alkyl, methoxyl, —$CF_3$, —$OCF_3$ or morpholinyl;

$R_5$ is —H, aryl or $C_3$-$C_8$ cycloalkyl; and wherein when L is

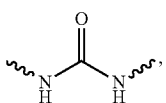

and $R_3$ is

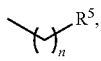

then $R_5$ is aryl or $C_3$-$C_8$ cycloalkyl;

wherein when L is

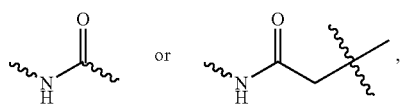

then $R_3$ is substituted 4-12 membered aromatic heterocyclic radical or

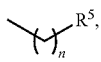

and $R_5$ is aryl or $C_3$-$C_8$ cycloalkyl;

n=0-4.

22. The pyrazolopyrimidine derivative or a pharmaceutically acceptable salt or hydrate thereof of claim 21, characterized in that: Y is oxygen or sulfur;

L is

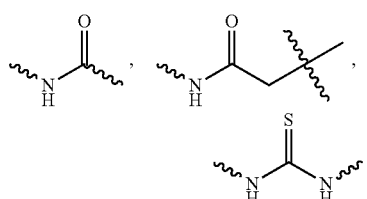

substituted at 3-position or 4-position on the benzene ring, wherein one end of atom N is connected with the benzene ring;

$R_1$ is —H, $C_1$-$C_4$ alkyl,

or substituted phenyl substituted methyl; and the substituent of the substituted phenyl is —H, halogen or $C_1$-$C_4$ alkyl;

$R_2$ is —H, halogen, $C_1$-$C_4$ alkyl, $C_1$-$C_4$ alkoxy or —$NO_2$;

$R_3$ is substituted 4-12 membered aromatic heterocyclic radical,

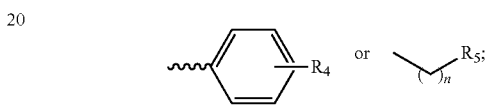

the substituent on the substituted 4-12 membered aromatic heterocyclic radical is —H, $C_1$-$C_6$ alkyl, unsubstituted aryl, —$CF_3$ or 5-10 membered aromatic heterocyclic radical; and the number of heteroatoms on the substituted 4-12 membered aromatic heterocyclic radical is 1 to 4, and the heteroatom is N or O;

$R_4$ is —H, —F, —Cl, —Br, methyl, isopropyl, methoxyl, —$CF_3$, —$OCF_3$ or morpholinyl;

$R_5$ is —H, aryl or $C_3$-$C_8$ cycloalkyl; and wherein when L is

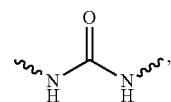

and $R_3$ is

then $R_5$ is aryl or $C_3$-$C_8$ cycloalkyl;

wherein when L is

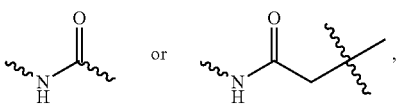

then $R_3$ is substituted 4-12 membered aromatic heterocyclic radical or

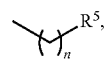

and $R_5$ is aryl or $C_3$-$C_8$ cycloalkyl;

n=0-3.

23. The pyrazolopyrimidine derivative or a pharmaceutically acceptable salt or hydrate thereof of claim 3, characterized in that: Y is oxygen or sulfur;

L is

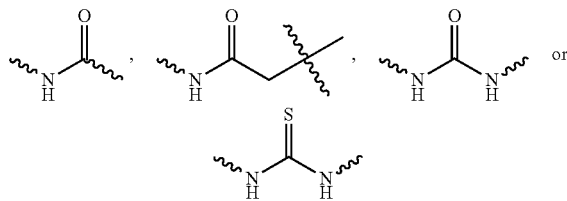

substituted at 3-position or 4-position on the benzene ring, wherein one end of atom N is connected with the benzene ring;

$R_1$ is —H, $C_1$-$C_4$ alkyl,

or substituted phenyl substituted methyl; and
the substituent of the substitute phenyl is —H, halogen or $C_1$-$C_4$ alkyl;
$R_2$ is —H, halogen, $C_1$-$C_4$ alkyl, $C_1$-$C_4$ alkoxy or —$NO_2$;
$R_3$ is substituted 4-12 membered aromatic heterocyclic radical,

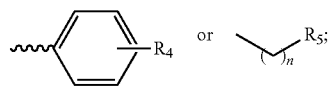

the substituent on the substituted 4-12 membered aromatic heterocyclic radical is —H, $C_1$-$C_6$ alkyl, unsubstituted aryl, —$CF_3$ or 5-10 membered aromatic heterocyclic radical; and the number of heteroatoms on the substituted 4-12 membered aromatic heterocyclic radical is 1 to 4, and the heteroatom is N or O;
$R_4$ is —H, halogen, $C_1$-$C_4$ alkyl, $C_1$-$C_4$ alkoxy, —$CF_3$, —$OCF_3$ or morpholinyl;
$R_5$ is —H, phenyl or $C_3$-$C_8$ cycloalkyl; and
wherein when L is

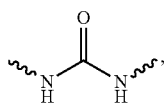

and $R_3$ is

then $R_5$ is phenyl or $C_3$-$C_8$ cycloalkyl;
wherein when L is

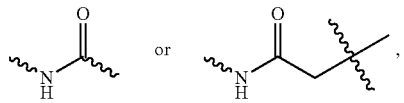

then $R_3$ is substituted 4-12 membered aromatic heterocyclic radical or

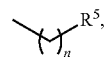

and $R_5$ is phenyl or $C_3$-$C_8$ cycloalkyl;
n=0-4.

24. The pyrazolopyrimidine derivative or a pharmaceutically acceptable salt or hydrate thereof of claim 23, characterized in that: Y is oxygen or sulfur;

L is

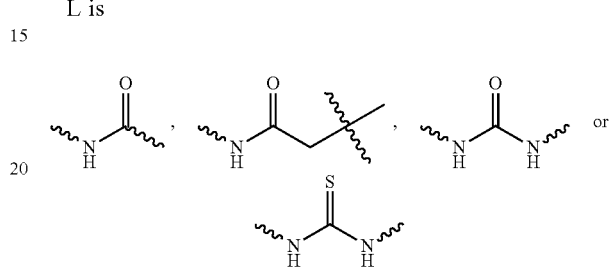

substituted at 3-position or 4-position on the benzene ring, wherein one end of atom N is connected with the benzene ring;

$R_1$ is —H, $C_1$-$C_4$ alkyl,

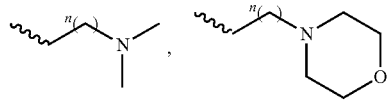

substituted phenyl substituted methyl; and
the substituent of the substituted phenyl is —H, halogen or $C_1$-$C_4$ alkyl;
$R_2$ is —H, halogen, $C_1$-$C_4$ alkyl, $C_1$-$C_4$ alkoxy or —$NO_2$;
$R_3$ is substituted 4-12 membered aromatic heterocyclic radical,

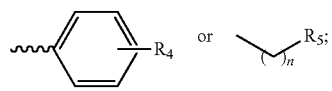

the substituent on the substituted 4-12 membered aromatic heterocyclic radical is —H, $C_1$-$C_6$ alkyl, unsubstituted aryl, —$CF_3$ or 5-10 membered aromatic heterocyclic radical; and the number of heteroatoms on the substituted 4-12 membered aromatic heterocyclic radical is 1 to 4, and the heteroatom is N or O;
$R_4$ is —H, halogen, $C_1$-$C_4$ alkyl, $C_1$-$C_4$ alkoxy, —$CF_3$, —$OCF_3$ or morpholinyl;
$R_5$ is —H, phenyl or cyclohexyl; and
wherein when L is

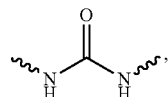

and R₃ is

then R₅ is phenyl or C₃-C₈ cycloalkyl;
wherein when L is

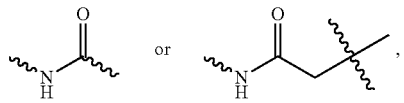

then R₃ is substituted 4-12 membered aromatic heterocyclic radical or

and R₅ is phenyl or cyclohexyl;
n=0-3.

26. The pyrazolopyrimidine derivative or a pharmaceutically acceptable salt or hydrate thereof of claim 3, characterized in that: Y is oxygen or sulfur;
L is

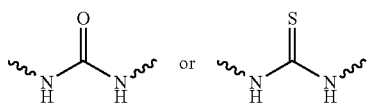

substituted at 4-position on the benzene ring;
R₁ is —H, C₁-C₄ alkyl,

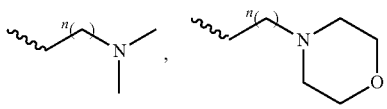

or substituted 6-10 membered aromatic ring substituted methyl; and the substituent on the substituted aromatic ring is —H, halogen or C₁-C₄ alkyl;
R₂ is —H, halogen, C₁-C₄ alkyl, C₁-C₄ alkoxy, C₁-C₄ alkyl sulfenyl or —NO₂;
R₃ is substituted 4-12 membered aromatic heterocyclic radical,

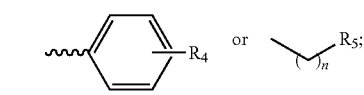

the substituent on the substituted 4-12 membered aromatic heterocyclic radical is —H, C₁-C₆ alkyl, unsubstituted aryl, —CF₃ or 5-10 membered aromatic heterocyclic radical; and the number of heteroatoms on the substituted 4-12 membered aromatic heterocyclic radical is 1 to 4, and the heteroatom is N, O or S;
R₄ is —H, halogen, C₁-C₄ alkyl, C₁-C₄ alkoxy, —CF₃, —OCF₃, morpholinyl or C₁-C₄ phenylalkyl;
R₅ is —H, aryl or C₃-C₈ cycloalkyl; and
wherein when L is

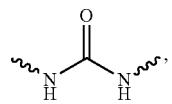

and R₃ is

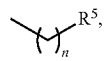

then R₅ is aryl or C₃-C₈ cycloalkyl;
n=0-4.

26. The pyrazolopyrimidine derivative or a pharmaceutically acceptable salt or hydrate thereof of claim 25, characterized in that: Y is oxygen or sulfur;
L is

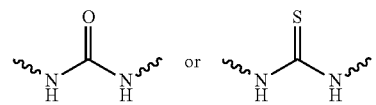

substituted at 4-position on the benzene ring;
R₁ is —H or C₁-C₄ alkyl;
R₂ is —H, halogen, C₁-C₄ alkyl, C₁-C₄ alkoxy, C₁-C₄ alkyl sulfenyl or —NO₂;
R₃ is substituted 4-12 membered aromatic heterocyclic radical,

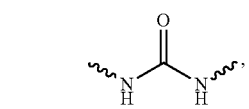

the substituent on the substituted 4-12 membered aromatic heterocyclic radical is —H, C₁-C₆ alkyl, unsubstituted aryl, —CF₃ or 5-10 membered aromatic heterocyclic radical; and the number of heteroatoms on the substituted 4-12 membered aromatic heterocyclic radical is 1 to 4, and the heteroatom is N, O or S;
R₄ is —H, halogen, C₁-C₄ alkyl, C₁-C₄ alkoxy, —CF₃, —OCF₃, morpholinyl or C₁-C₄ phenylalkyl;
R₅ is —H, aryl or C₃-C₈ cycloalkyl; and
wherein when L is

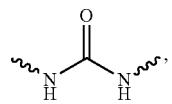

and R₃ is

then R₅ is aryl or C₃-C₈ cycloalkyl;
n=0-4.

27. The pyrazolopyrimidine derivative or a pharmaceutically acceptable salt or hydrate thereof of claim 26, characterized in that: Y is oxygen or sulfur;

L is

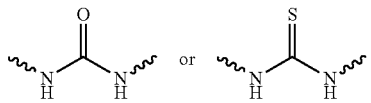

substituted at 4-position on the benzene ring;

$R_1$ is —H;

$R_2$ is —H, halogen, $C_1$-$C_4$ alkyl, $C_1$-$C_4$ alkoxy, $C_1$-$C_4$ alkyl sulfenyl or —NO$_2$;

$R_3$ is substituted 4-12 membered aromatic heterocyclic radical,

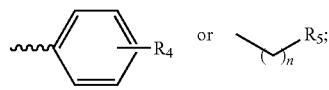

the substituent on the substituted 4-12 membered aromatic heterocyclic radical is —H, $C_1$-$C_6$ alkyl, unsubstituted aryl, —CF$_3$ or 5-10 membered aromatic heterocyclic radical; and the number of heteroatoms on the substituted 4-12 membered aromatic heterocyclic radical is 1 to 4, and the heteroatom is N, O or S;

$R_4$ is —H, halogen, $C_1$-$C_4$ alkyl, $C_1$-$C_4$ alkoxy, —CF$_3$, —OCF$_3$, morpholinyl or $C_1$-$C_4$ phenylalkyl;

$R_5$ is —H, aryl or $C_3$-$C_8$ cycloalkyl; and wherein when L is

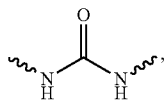

and $R_3$ is

then $R_5$ is aryl or $C_3$-$C_8$ cycloalkyl;

n=0-4.

28. The pyrazolopyrimidine derivative or a pharmaceutically acceptable salt or hydrate thereof of claim 27, characterized in that: Y is oxygen or sulfur;

L is

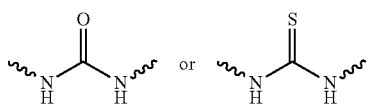

substituted at 4-position on the benzene ring;

$R_1$ is —H;

$R_2$ is —H, —F, —Cl, methyl, methoxy or —NO$_2$;

$R_3$ is substituted pyrazolyl, substituted isoxazolyl, substituted quinolyl, substituted pyridyl,

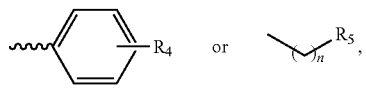

and the substituent is —H, $C_1$-$C_4$ alkyl, unsubstituted phenyl, —CF$_3$ or quinolyl;

$R_4$ is —H, —F, —Cl, —Br, methyl, isopropyl, methoxy, —CF$_3$, —OCF$_3$ or morpholinyl;

$R_5$ is —H, phenyl or cyclohexyl; and wherein when L is

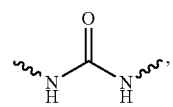

and $R_3$ is

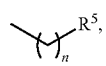

then $R_5$ is phenyl or cyclohexyl;

n=0-3.

29. The pyrazolopyrimidine derivative or a pharmaceutically acceptable salt or hydrate thereof of claim 2, when L is

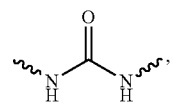

the derivative has the structural formula II as follows:

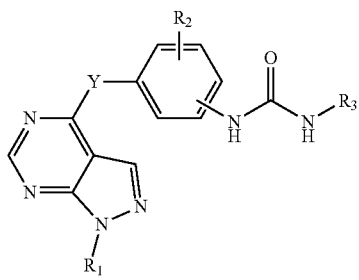

II wherein, Y is oxygen or sulfur;

$R_1$ is —H, $C_1$-$C_4$ alkyl,

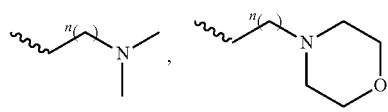

or substituted phenyl substituted methyl; and the substituent of the substituted phenyl is —H, halogen or $C_1$-$C_4$ alkyl;

$R_2$ is —H, halogen, $C_1$-$C_4$ alkyl, $C_1$-$C_4$ alkoxy or —NO$_2$;

R₃ is substituted 4-12 membered aromatic heterocyclic radical,

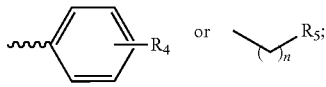

the substituent on the substituted 4-12 membered aromatic heterocyclic radical is —H, $C_1$-$C_6$ alkyl, unsubstituted aryl, —$CF_3$ or 5-10 membered aromatic heterocyclic radical; and the number of heteroatoms on the substituted 4-12 membered aromatic heterocyclic radical is 1 to 4, and the heteroatom is N, O or S;

$R_4$ is —H, halogen, $C_1$-$C_4$ alkyl, $C_1$-$C_4$ alkoxy, —$CF_3$, —$OCF_3$ or morpholinyl;

$R_5$ is aryl or $C_3$-$C_8$ cycloalkyl; and n=0-4.

30. The pyrazolopyrimidine derivative or a pharmaceutically acceptable salt or hydrate thereof of claim 29, characterized in that: Y is oxygen or sulfur;

$R_1$ is —H, $C_1$-$C_4$ alkyl,

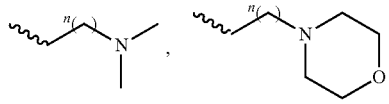

or substituted phenyl substituted methyl; and the substituent of the substituted phenyl is —H, —F, —Cl or —Br;

$R_2$ is —H, halogen, $C_1$-$C_4$ alkyl, $C_1$-$C_4$ alkoxy or —$NO_2$;

$R_3$ is substituted 4-12 membered aromatic heterocyclic radical,

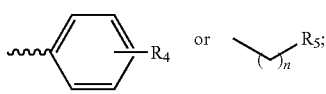

the substituent on the substituted 4-12 membered aromatic heterocyclic radical is —H, $C_1$-$C_6$ alkyl, unsubstituted aryl, —$CF_3$ or 5-10 membered aromatic heterocyclic radical; and the number of heteroatoms on the substituted 4-12 membered aromatic heterocyclic radical is 1 to 4, and the heteroatom is N, O or S;

$R_4$ is —H, halogen, $C_1$-$C_4$ alkyl, $C_1$-$C_4$ alkoxy, —$CF_3$, —$OCF_3$ or morpholinyl;

$R_5$ is aryl or $C_3$-$C_8$ cycloalkyl; and n=0-3.

31. The pyrazolopyrimidine derivative or a pharmaceutically acceptable salt or hydrate thereof of claim 30, characterized in that: Y is oxygen or sulfur;

$R_1$ is —H, $C_1$-$C_4$ alkyl,

or substituted phenyl substituted methyl; and the substituent of the substituted phenyl is —H or —Br;

$R_2$ is —H, halogen, $C_1$-$C_4$ alkyl, $C_1$-$C_4$ alkoxy or —$NO_2$;

$R_3$ is substituted 4-12 membered aromatic heterocyclic radical,

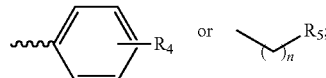

the substituent on the substituted 4-12 membered aromatic heterocyclic radical is —H, $C_1$-$C_6$ alkyl, unsubstituted aryl, —$CF_3$ or 5-10 membered aromatic heterocyclic radical; and the number of heteroatoms on the substituted 4-12 membered aromatic heterocyclic radical is 1 to 4, and the heteroatom is N, O or S;

$R_4$ is —H, halogen, $C_1$-$C_4$ alkyl, $C_1$-$C_4$ alkoxy, —$CF_3$, —$OCF_3$ or morpholinyl;

$R_5$ is aryl or $C_3$-$C_5$ cycloalkyl; and n=0-3.

32. The pyrazolopyrimidine derivative or a pharmaceutically acceptable salt or hydrate thereof of claim 31, characterized in that: Y is oxygen or sulfur;

$R_1$ is —H, $C_1$-$C_4$ alkyl,

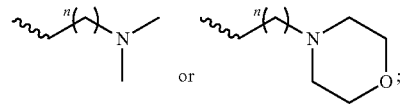

$R_2$ is —H, halogen, $C_1$-$C_4$ alkyl, $C_1$-$C_4$ alkoxy or —$NO_2$;

$R_3$ is substituted 4-12 membered aromatic heterocyclic radical,

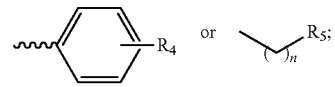

the substituent on the substituted 4-12 membered aromatic heterocyclic radical is —H, $C_1$-$C_6$ alkyl, unsubstituted aryl, —$CF_3$ or 5-10 membered aromatic heterocyclic radical; and the number of heteroatoms on the substituted 4-12 membered aromatic heterocyclic radical is 1 to 4, and the heteroatom is N, O or S;

$R_4$ is —H, halogen, $C_1$-$C_4$ alkyl, $C_1$-$C_4$ alkoxy, —$CF_3$, —$OCF_3$, morpholinyl;

$R_5$ is aryl or $C_3$-$C_8$ cycloalkyl; and n=0-3.

33. The pyrazolopyrimidine derivative or a pharmaceutically acceptable salt or hydrate thereof of claim 32, characterized in that: Y is oxygen or sulfur;

$R_1$ is —H,

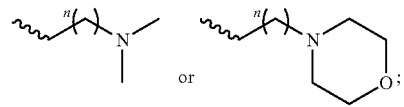

$R_2$ is —H, halogen, $C_1$-$C_4$ alkyl, $C_1$-$C_4$ alkoxy or —$NO_2$;

$R_3$ is substituted 4-12 membered aromatic heterocyclic radical,

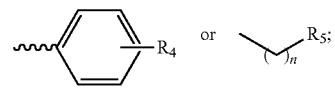

the substituent on the substituted 4-12 membered aromatic heterocyclic radical is —H, $C_1$-$C_6$ alkyl, unsubstituted aryl, —$CF_3$ or 5-10 membered aromatic heterocyclic radical; and the number of heteroatoms on the substituted 4-12 membered aromatic heterocyclic radical is 1 to 4, and the heteroatom is N, O or S;

$R_4$ is —H, halogen, $C_1$-$C_4$ alkyl, $C_1$-$C_4$ alkoxy, —$CF_3$, —$OCF_3$, morpholinyl;

$R_5$ is aryl or $C_3$-$C_8$ cycloalkyl; and n=0-3.

34. The pyrazolopyrimidine derivative or a pharmaceutically acceptable salt or hydrate thereof of claim 33, characterized in that: Y is oxygen or sulfur;

$R_1$ is —H;

$R_2$ is —H, halogen, $C_1$-$C_4$ alkyl, $C_1$-$C_4$ alkoxy or —$NO_2$;

$R_3$ is substituted 4-12 membered aromatic heterocyclic radical,

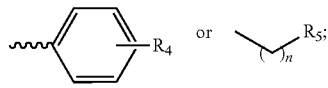

the substituent on the substituted 4-12 membered aromatic heterocyclic radical is —H, $C_1$-$C_6$ alkyl, unsubstituted aryl, —$CF_3$ or 5-10 membered aromatic heterocyclic radical; and the number of heteroatoms on the substituted 4-12 membered aromatic heterocyclic radical is 1 to 4, and the heteroatom is N, O or S;

$R_4$ is —H, halogen, $C_1$-$C_4$ alkyl, $C_1$-$C_4$ alkoxy, —$CF_3$, —$OCF_3$, morpholinyl;

$R_5$ is aryl or $C_3$-$C_8$ cycloalkyl; and n=0-3.

35. The pyrazolopyrimidine derivative or a pharmaceutically acceptable salt or hydrate thereof of claim 29, characterized in that: Y is oxygen or sulfur;

$R_1$ is —H, $C_1$-$C_4$ alkyl,

or substituted phenyl substituted methyl; and the substituent of the substituted phenyl is —H, halogen or $C_1$-$C_4$ alkyl;

$R_2$ is —H, —F, —Cl, —Br, $C_1$-$C_4$ alkyl, $C_1$-$C_4$ alkoxy or —$NO_2$;

$R_3$ is substituted 4-12 membered aromatic heterocyclic radical,

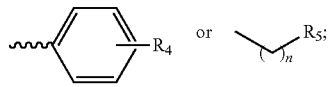

the substituent on the substituted 4-12 membered aromatic heterocyclic radical is —H, $C_1$-$C_6$ alkyl, unsubstituted aryl, —$CF_3$ or 5-10 membered aromatic heterocyclic radical; and the number of heteroatoms on the substituted 4-12 membered aromatic heterocyclic radical is 1 to 4, and the heteroatom is N, O or S;

$R_4$ is —H, halogen, $C_1$-$C_4$ alkyl, $C_1$-$C_4$ alkoxy, —$CF_3$, —$OCF_3$ or morpholinyl;

$R_5$ is aryl or $C_3$-$C_8$ cycloalkyl; and n=0-4.

36. The pyrazolopyrimidine derivative or a pharmaceutically acceptable salt or hydrate thereof of claim 35, characterized in that: Y is oxygen or sulfur;

$R_1$ is —H, $C_1$-$C_4$ alkyl,

or substituted phenyl substituted methyl; and the substituent of the substituted phenyl is —H, halogen or $C_1$-$C_4$ alkyl;

$R_2$ is —H, —F, —Cl, methyl, methoxy or —$NO_2$;

$R_3$ is substituted 4-12 membered aromatic heterocyclic radical,

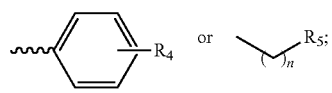

the substituent on the substituted 4-12 membered aromatic heterocyclic radical is —H, $C_1$-$C_6$ alkyl, unsubstituted aryl, —$CF_3$ or 5-10 membered aromatic heterocyclic radical; and the number of heteroatoms on the substituted 4-12 membered aromatic heterocyclic radical is 1 to 4, and the heteroatom is N, O or S;

$R_4$ is —H, halogen, $C_1$-$C_4$ alkyl, $C_1$-$C_4$ alkoxy, —$CF_3$, —$OCF_3$ or morpholinyl;

$R_5$ is aryl or $C_3$-$C_8$ cycloalkyl; and n=0-3.

37. The pyrazolopyrimidine derivative or a pharmaceutically acceptable salt or hydrate thereof of claim 29, characterized in that: Y is oxygen or sulfur;

$R_1$ is —H, $C_1$-$C_4$ alkyl,

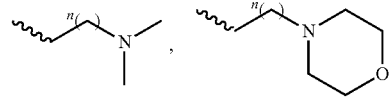

or substituted phenyl substituted methyl; and the substituent of the substituted phenyl is —H, halogen or $C_1$-$C_4$ alkyl;

$R_2$ is —H, halogen, $C_1$-$C_4$ alkyl, $C_1$-$C_4$ alkoxy or —$NO_2$;

$R_3$ is substituted 5-10 membered aromatic heterocyclic radical,

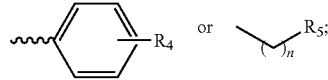

the substituent on the substituted 5-10 membered aromatic heterocyclic radical is —H, $C_1$-C4 alkyl, unsubstituted aryl, —$CF_3$ or quinolyl; and the number of heteroatoms on the substituted 5-10 membered aromatic heterocyclic radical is 1 to 3, and the heteroatom is N or O;

$R_4$ is —H, halogen, $C_1$-$C_4$ alkyl, $C_1$-$C_4$ alkoxy, —$CF_3$, —$OCF_3$ or morpholinyl;
$R_5$ is aryl or $C_3$-$C_8$ cycloalkyl; and
n=0-4.

38. The pyrazolopyrimidine derivative or a pharmaceutically acceptable salt or hydrate thereof of claim 37, characterized in that: Y is oxygen or sulfur;
$R_1$ is —H, $C_1$-$C_4$ alkyl,

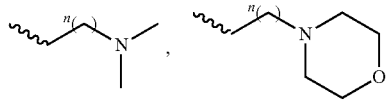

or substituted phenyl substituted methyl; and
the substituent of the substituted phenyl is —H, halogen or $C_1$-$C_4$ alkyl;
$R_2$ is —H, halogen, $C_1$-$C_4$ alkyl, $C_1$-$C_4$ alkoxy or —$NO_2$;
$R_3$ is substituted pyrazolyl, substituted isoxazolyl, substituted quinolyl, substituted pyridyl,

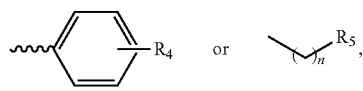

and the substituent is —H, $C_1$-$C_4$ alkyl, unsubstituted phenyl, —$CF_3$ or quinolyl;
$R_4$ is —H, halogen, $C_1$-$C_4$ alkyl, $C_1$-$C_4$ alkoxy, —$CF_3$, —$OCF_3$ or morpholinyl;
$R_5$ is aryl or $C_3$-$C_8$ cycloalkyl; and
n=0-3.

39. The pyrazolopyrimidine derivative or a pharmaceutically acceptable salt or hydrate thereof of claim 29, characterized in that: Y is oxygen or sulfur;
$R_1$ is —H, $C_1$-$C_4$ alkyl,

or substituted phenyl substituted methyl; and
the substituent of the substituted phenyl is —H, halogen or $C_1$-$C_4$ alkyl;
$R_2$ is —H, halogen, $C_1$-$C_4$ alkyl, $C_1$-$C_4$ alkoxy or —$NO_2$;
$R_3$ is substituted 4-12 membered aromatic heterocyclic radical,

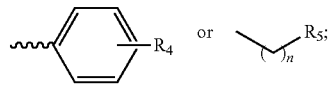

the substituent on the substituted 4-12 membered aromatic heterocyclic radical is —H, $C_1$-$C_6$ alkyl, unsubstituted aryl, —$CF_3$ or 5-10 membered aromatic heterocyclic radical; and the number of heteroatoms on the substituted 4-12 membered aromatic heterocyclic radical is 1 to 4, and the heteroatom is N or O;
$R_4$ is —H, —F, —Cl, —Br, $C_1$-$C_4$ alkyl, $C_1$-$C_4$ alkoxy, —$CF_3$, —$OCF_3$ or morpholinyl;
$R_5$ is aryl or $C_3$-$C_8$ cycloalkyl; and
n=0-4.

40. The pyrazolopyrimidine derivative or a pharmaceutically acceptable salt or hydrate thereof of claim 39, characterized in that: Y is oxygen or sulfur;
$R_1$ is —H, $C_1$-$C_4$ alkyl,

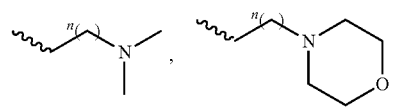

or substituted phenyl substituted methyl; and
the substituent of the substituted phenyl is —H, halogen or $C_1$-$C_4$ alkyl;
$R_2$ is —H, halogen, $C_1$-$C_4$ alkyl, $C_1$-$C_4$ alkoxy or —$NO_2$;
$R_3$ is substituted 4-12 membered aromatic heterocyclic radical,

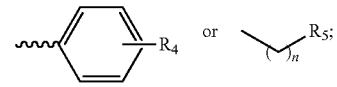

the substituent on the substituted 4-12 membered aromatic heterocyclic radical is —H, $C_1$-$C_6$ alkyl, unsubstituted aryl, —$CF_3$ or 5-10 membered aromatic heterocyclic radical; and the number of heteroatoms on the substituted 4-12 membered aromatic heterocyclic radical is 1 to 4, and the heteroatom is N or O;
$R_4$ is —H, —F, —Cl, —Br, methyl, isopropyl, methoxyl, —$CF_3$, —$OCF_3$ or morpholinyl;
$R_5$ is aryl or $C_3$-$C_8$ cycloalkyl; and
n=0-3.

41. The pyrazolopyrimidine derivative or a pharmaceutically acceptable salt or hydrate thereof of claim 29, characterized in that: Y is oxygen or sulfur;
$R_1$ is —H, $C_1$-$C_4$ alkyl,

or substituted phenyl substituted methyl; and
the substituent of the substituted phenyl is —H, halogen or $C_1$-$C_4$ alkyl;
$R_2$ is —H, halogen, $C_1$-$C_4$ alkyl, $C_1$-$C_4$ alkoxy or —$NO_2$;
$R_3$ is substituted 4-12 membered aromatic heterocyclic radical,

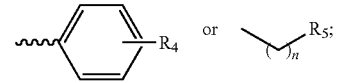

the substituent on the substituted 4-12 membered aromatic heterocyclic radical is —H, $C_1$-$C_6$ alkyl, unsubstituted aryl, —$CF_3$ or 5-10 membered aromatic heterocyclic radical; and the number of heteroatoms on the substituted 4-12 membered aromatic heterocyclic radical is 1 to 4, and the heteroatom is N or O;

R$_4$ is —H, halogen, C$_1$-C$_4$ alkyl, C$_1$-C$_4$ alkoxy, —CF$_3$, —OCF$_3$ or morpholinyl;
R$_5$ is phenyl or C$_3$-C$_8$ cycloalkyl; and
n=0-4.

42. The pyrazolopyrimidine derivative or a pharmaceutically acceptable salt or hydrate thereof of claim 41, characterized in that: Y is oxygen or sulfur;
R$_1$ is —H, C$_1$-C$_4$ alkyl,

or substituted phenyl substituted methyl; and
the substituent of the substituted phenyl is —H, halogen or C$_1$-C$_4$ alkyl;
R$_2$ is —H, halogen, C$_1$-C$_4$ alkyl, C$_1$-C$_4$ alkoxy or —NO$_2$;
R$_3$ is substituted 4-12 membered aromatic heterocyclic radical,

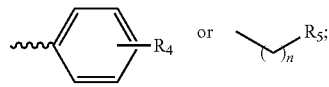

the substituent on the substituted 4-12 membered aromatic heterocyclic radical is —H, C$_1$-C$_6$ alkyl, unsubstituted aryl, —CF$_3$ or 5-10 membered aromatic heterocyclic radical; and the number of heteroatoms on the substituted 4-12 membered aromatic heterocyclic radical is 1 to 4, and the heteroatom is N or O;
R$_4$ is —H, halogen, C$_1$-C$_4$ alkyl, C$_1$-C$_4$ alkoxy, —CF$_3$, —OCF$_3$ or morpholinyl;
R$_5$ is phenyl or cyclohexyl; and
n=0-3.

43. The pyrazolopyrimidine derivative or a pharmaceutically acceptable salt or hydrate thereof of claim 29, characterized in that: Y is oxygen or sulfur;
R$_1$ is —H, C$_1$-C$_4$ alkyl,

or substituted phenyl substituted methyl; and
the substituent of the substituted phenyl is —H, halogen or C$_1$-C$_4$ alkyl;
R$_2$ is —H, halogen, C$_1$-C$_4$ alkyl, C$_1$-C$_4$ alkoxy, or —NO$_2$;
R$_3$ is substituted 4-12 membered aromatic heterocyclic radical,

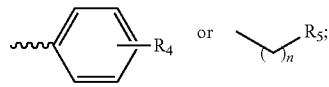

the substituent on the substituted 4-12 membered aromatic heterocyclic radical is —H, C$_1$-C$_6$ alkyl, unsubstituted aryl, —CF$_3$ or 5-10 membered aromatic heterocyclic radical; and the number of heteroatoms on the substituted 4-12 membered aromatic heterocyclic radical is 1 to 4, and the heteroatom is N, O or S;
R$_4$ is —H, halogen, C$_1$-C$_4$ alkyl, C$_1$-C$_4$ alkoxy, —CF$_3$, —OCF$_3$ or morpholinyl;
R$_5$ is aryl or C$_3$-C$_8$ cycloalkyl; and
n=0-4.

44. The pyrazolopyrimidine derivative or a pharmaceutically acceptable salt or hydrate thereof of claim 43, characterized in that: Y is oxygen or sulfur;
R$_1$ is —H or C$_1$-C$_4$ alkyl;
R$_2$ is —H, halogen, C$_1$-C$_4$ alkyl, C$_1$-C$_4$ alkoxy, or —NO$_2$;
R$_3$ is substituted 4-12 membered aromatic heterocyclic radical,

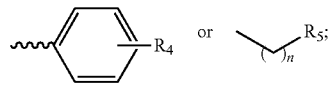

the substituent on the substituted 4-12 membered aromatic heterocyclic radical is —H, C$_1$-C$_6$ alkyl, unsubstituted aryl, —CF$_3$ or 5-10 membered aromatic heterocyclic radical; and the number of heteroatoms on the substituted 4-12 membered aromatic heterocyclic radical is 1 to 4, and the heteroatom is N, O or S;
R$_4$ is —H, halogen, C$_1$-C$_4$ alkyl, C$_1$-C$_4$ alkoxy, —CF$_3$, —OCF$_3$ or morpholinyl;
R$_5$ is aryl or C$_3$-C$_8$ cycloalkyl; and
n=0-4.

45. The pyrazolopyrimidine derivative or a pharmaceutically acceptable salt or hydrate thereof of claim 44, characterized in that: Y is oxygen or sulfur;
R$_1$ is —H;
R$_2$ is —H, halogen, C$_1$-C$_4$ alkyl, C$_1$-C$_4$ alkoxy, or —NO$_2$;
R$_3$ is substituted 4-12 membered aromatic heterocyclic radical,

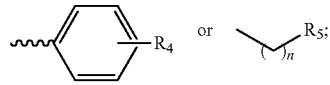

the substituent on the substituted 4-12 membered aromatic heterocyclic radical is —H, C$_1$-C$_6$ alkyl, unsubstituted aryl, —CF$_3$ or 5-10 membered aromatic heterocyclic radical; and the number of heteroatoms on the substituted 4-12 membered aromatic heterocyclic radical is 1 to 4, and the heteroatom is N, O or S;
R$_4$ is —H, halogen, C$_1$-C$_4$ alkyl, C$_1$-C$_4$ alkoxy, —CF$_3$, —OCF$_3$ or morpholinyl;
R$_5$ is aryl or C$_3$-C$_8$ cycloalkyl; and
n=0-4.

46. The pyrazolopyrimidine derivative or a pharmaceutically acceptable salt or hydrate thereof of claim 45, characterized in that: Y is oxygen or sulfur;
R$_1$ is —H;
R$_2$ is —H, —F, —Cl, methyl, methoxy or —NO$_2$;
R$_3$ is substituted pyrazolyl, substituted isoxazolyl, substituted quinolyl, substituted pyridyl,

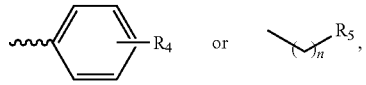

and the substituent is —H, $C_1$-$C_4$ alkyl, unsubstituted phenyl, —$CF_3$ or quinolyl;
$R_4$ is —H, —F, —Cl, —Br, methyl, isopropyl, methoxy, —$CF_3$, —$OCF_3$ or morpholinyl;
$R_5$ is phenyl or cyclohexyl; and
n=0-3.

47. The pyrazolopyrimidine derivative or a pharmaceutically acceptable salt or hydrate thereof of claim 2, when L is

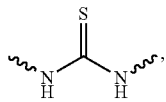

the derivative has the structural formula III as follow:

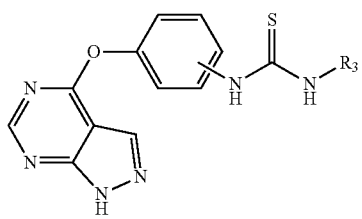

wherein, $R_3$ is substituted 4-12 membered aromatic heterocyclic radical,

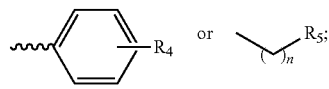

the substituent on the substituted 4-12 membered aromatic heterocyclic radical is —H, $C_1$-$C_6$ alkyl, unsubstituted aryl, —$CF_3$ or 5-10 membered aromatic heterocyclic radical; and the number of heteroatoms on the substituted 4-12 membered aromatic heterocyclic radical is 1 to 4, and the heteroatom is N, O or S;
$R_4$ is —H, halogen, $C_1$-$C_4$ alkyl, $C_1$-$C_4$ alkoxy, —$CF_3$, —$OCF_3$ or morpholinyl;
$R_5$ is —H, aryl or $C_3$-$C_8$ cycloalkyl; and
n=0-4.

48. The pyrazolopyrimidine derivative or a pharmaceutically acceptable salt or hydrate thereof of claim 47, characterized in that:
$R_3$ is substituted 5-10 membered aromatic heterocyclic radical or

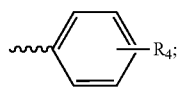

the substituent on the substituted 5-10 membered aromatic heterocyclic radical is —H, $C_1$-$C_6$ alkyl, unsubstituted aryl, —$CF_3$ or 5-10 membered aromatic heterocyclic radical; and the number of heteroatoms on the substituted 5-10 membered aromatic heterocyclic radical is 1 to 4, and the heteroatom is N or O; and $R_4$ is —H, halogen, $C_1$-$C_4$ alkyl, $C_1$-$C_4$ alkoxy, —$CF_3$, —$OCF_3$ or morpholinyl.

49. The pyrazolopyrimidine derivative or a pharmaceutically acceptable salt or hydrate thereof of claim 48, characterized in that:
$R_3$ is

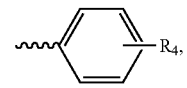

substituted pyrazolyl, substituted isoxazolyl, substituted quinolyl or substituted pyridyl, and the substituent is —H, $C_1$-$C_4$ alkyl, unsubstituted phenyl, —$CF_3$ or quinolyl; and
$R_4$ is —H, halogen, $C_1$-$C_4$ alkyl, $C_1$-$C_4$ alkoxy, —$CF_3$, —$OCF_3$ or morpholinyl.

50. The pyrazolopyrimidine derivative or a pharmaceutically acceptable salt or hydrate thereof of claim 49, characterized in that $R_3$ is

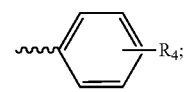

and
$R_4$ is —H, halogen, $C_1$-$C_4$ alkyl, $C_1$-$C_4$ alkoxy, —$CF_3$, —$OCF_3$ or morpholinyl.

51. The pyrazolopyrimidine derivative or a pharmaceutically acceptable salt or hydrate thereof of claim 50, characterized in that $R_3$ is

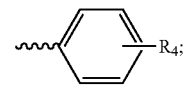

$R_4$ is —H, —F, —Cl, —Br, $C_1$-$C_4$ alkyl, $C_1$-$C_4$ alkoxy or —$CF_3$.

52. The pyrazolopyrimidine derivative or a pharmaceutically acceptable salt or hydrate thereof of claim 51, characterized in that $R_3$ is

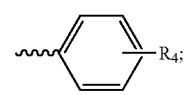

and
$R_4$ is —H, $C_1$-$C_4$ alkyl or —$CF_3$.

53. The pyrazolopyrimidine derivative or a pharmaceutically acceptable salt or hydrate thereof of claim 52, characterized in that $R_3$ is

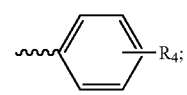

and
$R_4$ is —H or —$CF_3$.

54. The pyrazolopyrimidine derivative or a pharmaceutically acceptable salt or hydrate thereof of claim 1, characterized in that:

Y is oxygen, L is

[structure: -NH-C(=O)-NH-]

substituted at 4-position on the benzene ring; $R_1$ is —H; $R_2$ is —H or halogen; and $R_3$ is substituted 4-12 membered aromatic heterocyclic radical; the number of heteroatoms on the substituted aromatic heterocyclic radical is 1 to 4, the heteroatom is N, O or S; the substituent on the substituted 4-12 membered aromatic heterocyclic radical is —H, $C_1$-$C_6$ alkyl, substituted phenyl, —$CF_3$, 5-10 membered aromatic heterocyclic radical, carboxyl or $C_3$-$C_6$ cycloalkyl; and the substituent on the substituted phenyl is —H or halogen.

55. The pyrazolopyrimidine derivative or a pharmaceutically acceptable salt or hydrate thereof of claim 54, characterized in that:

Y is oxygen, L is

[structure: -NH-C(=O)-NH-]

substituted at 4-position on the benzene ring; $R_1$ is —H; $R_2$ is —H or halogen; and $R_3$ is substituted 4-6 membered aromatic heterocyclic radical; the number of heteroatoms on the substituted aromatic heterocyclic radical is 1 to 2, the heteroatom is N or S; the substituent on the substituted 4-6 membered aromatic heterocyclic radical is —H, $C_1$-$C_6$ alkyl, substituted phenyl, —$CF_3$, 5-10 membered aromatic heterocyclic radical, carboxyl or $C_3$-$C_6$ cycloalkyl; and the substituent on the substituted phenyl is —H or halogen.

56. The pyrazolopyrimidine derivative or a pharmaceutically acceptable salt or hydrate thereof of claim 55, characterized in that:

Y is oxygen, L is

[structure: -NH-C(=O)-NH-]

substituted at 4-position on the benzene ring; $R_1$ is —H; $R_2$ is —H or halogen; and $R_3$ is substituted pyrazolyl or thiazolyl; the substituent on the substituted pyrazolyl or thiazolyl is —H, $C_1$-$C_6$ alkyl, substituted phenyl, —$CF_3$, 5-10 membered aromatic heterocyclic radical, carboxyl or $C_3$-$C_6$ cycloalkyl; and the substituent on the substituted phenyl is —H or halogen.

57. The pyrazolopyrimidine derivative or a pharmaceutically acceptable salt or hydrate thereof of claim 56, characterized in that:

Y is oxygen, L is

[structure: -NH-C(=O)-NH-]

substituted at 4-position on the benzene ring; $R_1$ is —H; $R_2$ is —H or halogen; and $R_3$ is substituted pyrazolyl or thiazolyl; the substituent on the substituted pyrazolyl or thiazolyl is —H, $C_1$-$C_4$ alkyl, substituted phenyl, carboxyl or $C_3$-$C_6$ cycloalkyl; and the substituent on the substituted phenyl is —H or halogen.

58. The pyrazolopyrimidine derivative or a pharmaceutically acceptable salt or hydrate thereof of claim 57, characterized in that:

Y is oxygen, L is

[structure: -NH-C(=O)-NH-]

substituted at 4-position on the benzene ring; $R_1$ is —H; $R_2$ is —H or halogen; and $R_3$ is substituted pyrazolyl or thiazolyl; and the substituent on the substituted pyrazolyl or thiazolyl is —H, $C_1$-$C_4$ alkyl, para-fluorophenyl, carboxyl or cyclopentyl.

59. A pharmaceutical composition comprising a pyrazolopyrimidine derivative, or a pharmaceutically acceptable salt or hydrate thereof of claim 1 and pharmaceutically acceptable auxiliary components.

60. A pyrazolopyrimidine derivative, characterized by being titled 1-(4-((1H-pyrazolopyrimidin-4-yl)oxy)phenyl)-3-(4-(trifluoromethyl)phenyl)urea, 1-(4-((1H-pyrazolopyrimidin-4-yl)oxy)phenyl)-3-(4-chloro-3-(trifluoromethyl)phenyl)urea, 1-(4-((1H-pyrazolopyrimidin-4-yl)oxy)phenyl)-3-(4-bromophenyl)urea, 1-(4-((1H-pyrazolopyrimidin-4-yl)oxy)phenyl)-3-(2,3-dimethylphenyl)urea, 1-(4-((1H-pyrazolopyrimidin-4-yl)oxy)phenyl)-3-(3-methoxyphenyl)urea, 1-(4-((1H-pyrazolopyrimidin-4-yl)oxy)phenyl)-3-(3-(trifluoromethyl)phenyl)urea, 1-(4-((1H-pyrazolopyrimidin-4-yl)oxy)-3-fluorophenyl)-3-(3-isopropylphenyl)urea, 1-(4-((1H-pyrazolopyrimidin-4-yl)oxy)-3-fluorophenyl)-3-(3-(trifluoromethoxy)phenyl)urea, 1-(4-((1H-pyrazolopyrimidin-4-yl)oxy)-3-fluorophenyl)-3-(4-(trifluoromethyl)phenyl)urea, 1-(4-((1H-pyrazolopyrimidin-4-yl)oxy)-3-fluorophenyl)-3-(4-chloro-3-(trifluoromethyl)phenyl)urea, 1-(4-((1H-pyrazolopyrimidin-4-yl)oxy)-2-methylphenyl)-3-(3-(trifluoromethyl)phenyl)urea, 1-(4-((1H-pyrazolopyrimidin-4-yl)oxy)phenyl)-3-(3,5-bis(trifluoromethyl)phenyl)urea, 1-(4-((1H-pyrazolopyrimidin-4-yl)oxy)phenyl)-3-(2-chloro-4-(trifluoromethyl)phenyl)urea, 1-(4-((1H-pyrazolopyrimidin-4-yl)oxy)phenyl)-3-(3-fluorophenyl)urea, 1-(4-((1H-pyrazolopyrimidin-4-yl)oxy)phenyl)-3-phenylurea, 1-(4-((1H-pyrazolopyrimidin-4-yl)oxy)phenyl)-3-(4-morpholinphenyl)urea, 1-(4-((1H-pyrazolopyrimidin-4-yl)oxy)phenyl)-3-(4-fluorophenyl)urea, (S)-1-(4-((1H-pyrazolopyrimidin-4-yl)oxy)phenyl)-3-(1-phenethyl)urea, (R)-1-(4-((1H-pyrazolopyrimidin-4-yl)oxy)phenyl)-3-(1-phenethyl)urea, 1-(4-((1H-pyrazolopyrimidin-4-yl)oxy)phenyl)-3-(methylcyclohexyl)

urea, 1-(4-((1H-pyrazolopyrimidin-4-yl)oxy)phenyl)-3-cyclohexylurea, 1-(4-((1H-pyrazolopyrimidin-4-yl)oxy)phenyl)-3-(6-quinolyl)urea, 1-(4-((1H-pyrazolopyrimidin-4-yl)oxy)phenyl)-3-pyridylurea, 1-(4-((1H-pyrazolopyrimidin-4-yl)oxy)phenyl)-3-(3-tert-butyl-1-phenyl-1H-pyrazol-5-yl)urea, 1-(4-((1H-pyrazolopyrimidin-4-yl)oxy)phenyl)-3-(3-tert-butylisoxazol-5-yl)urea, 1-(4-((1H-pyrazolopyrimidin-4-yl)oxy)phenyl)-3-(5-tert-butylisoxazol-3-yl)urea, 1-(4-((1H-pyrazolopyrimidin-4-yl)oxy)phenyl)-3-(3-isopropyl-1-methyl-pyrazol-5-yl)urea, 1-(4-((1H-pyrazolopyrimidin-4-yl)oxy)phenyl)-3-(5-(trifluoromethyl)isoxazol-3-yl)urea, 1-(4-((1H-pyrazolopyrimidin-4-yl)oxy)-2-methylphenyl)-3-(5-tert-butylisoxazol-3-yl)urea, 1-(4-((1H-pyrazolopyrimidin-4-yl)oxy)-2-fluorophenyl)-3-(5-tert-butylisoxazol-3-yl)urea, 1-(4-((1H-pyrazolopyrimidin-4-yl)oxy)-3-fluorophenyl)-3-(5-tert-butylisoxazol-3-yl)urea, 1-(4-((1H-pyrazolopyrimidin-4-yl)oxy)-3-chlorophenyl)-3-(3-tert-butyl-1-methylpyrazol-5-yl)urea, 1-(4-((1H-pyrazolopyrimidin-4-yl)oxy)-3,5-difluorophenyl)-3-(5-tert-butylisoxazol-3-yl)urea, 1-(4-((1H-pyrazolopyrimidin-4-yl)oxy)phenyl)-3-(3-tert-butyl-1-methyl-1H-pyrazol-5-yl)urea, 1-(4-((1H-pyrazolopyrimidin-4-yl)oxy)phenyl)-3-(1-methyl-3(trifluoromethyl) 1H-pyrazol-5-yl)urea, 1-(4-((1H-pyrazolopyrimidin-4-yl)oxy)-3-fluorophenyl)-3-(1-methyl-3 (trifluoromethyl)1H-pyrazol-5-yl)urea, 1-(4-((1H-pyrazolopyrimidin-4-yl)oxy)-2-nitrophenyl)-3-(5-tert-butylisoxazol-3-yl)urea, 1-(4-((1H-pyrazolopyrimidin-4-yl)oxy)-3-fluorophenyl)-3-(3-tert-butylisoxazol-5-yl)urea, 1-(4-((1H-pyrazolopyrimidin-4-yl)oxy)-2-methoxyphenyl)-3-(5-tert-butylisoxazol-3-yl)urea, 1-(4-((1H-pyrazolopyrimidin-4-yl)oxy)phenyl)-3-(3-tert-butyl-1-(quinolin-7-yl)-1H-pyrazol-5-yl)urea, 1-(3-((1H-pyrazolopyrimidin-4-yl)oxy)phenyl)-3-(3-(trifluoromethyl)phenyl)urea, 1-(3-((1H-pyrazolopyrimidin-4-yl)oxy)phenyl)-3-(4-chloro-3-(trifluoromethyl)phenyl)urea, 1-(3-((1H-pyrazolopyrimidin-4-yl)oxy)phenyl)-3-(4-(trifluoromethyl)phenyl)urea, 1-(3-((1H-pyrazolopyrimidin-4-yl)oxy)phenyl)-3-(5-tert-butylisoxazol-3-yl)urea, 1-(4-((1H-pyrazolopyrimidin-4-yl)oxy)phenyl)-3-phenylthiourea, 1-(4-((1H-pyrazolopyrimidin-4-yl)oxy)phenyl)-3-(3-trifluoromethylphenyl)thiourea, 1-(4-(1H-pyrazolopyrimidin-4-sulfydryl)phenyl)-3-(4-trifluoromethyl)phenyl)urea, 1-(4-(1H-pyrazolopyrimidin-4-sulfydryl)phenyl)-3-(3-(trifluoromethyl)phenyl)urea, 1-(4-(1H-pyrazolopyrimidin-4-sulfydryl)phenyl)-3-(5-tert-butylisoxazol-3-yl)urea, 1-(4-((1H-pyrazolopyrimidin-4-yl)oxy)-3-fluorophenyl)-3-(3-tert-butyl-1-methylpyrazol-5-yl)urea, 1-(4-((1H-pyrazolopyrimidin-4-yl)oxy)-3-chlorophenyl)-3-(5-tert-butylisoxazol-3-yl)urea, 1-(4-((1H-pyrazolopyrimidin-4-yl)oxy)-2-fluorophenyl)-3-(4-chloro-3-(trifluoromethyl)phenyl)urea, 1-(4-((1H-pyrazolopyrimidin-4-yl)oxy)-2-chlorophenyl)-3-(4-chloro-3-(trifluoromethyl)phenyl)urea, 1-(4-((1H-pyrazolopyrimidin-4-yl)oxy)-3-fluorophenyl)-3-(3-tert-butyl-1-phenyl-1H-pyrazol-5-yl)urea, 1-(4-((1H-pyrazolopyrimidin-4-yl)oxy)-3-chlorophenyl)-3-(3-tert-butyl-1-phenyl-1H-pyrazol-5-yl)urea, 5-(3-(4-((1H-pyrazolopyrimidin-4-yl)oxy)phenyl)carbamido)-3-tert-butyl-1H-pyrazol-1-carboxylic acid, 5-(3-(4-((1H-pyrazolopyrimidin-4-yl)oxy)-3-fluoro-phenyl)carbamido)-3-tert-butyl-1H-pyrazol-1-carboxylic acid, 1-(4-((1H-pyrazolopyrimidin-4-yl)oxy)-3-fluorophenyl)-3-(3-tert-butyl-1-(4-fluoro-phenyl)-1H-pyrazol-5-yl)urea, 1-(4-((1H-pyrazolopyrimidin-4-yl)oxy)phenyl)-3-(3-tert-butyl-1-cyclopentyl-1H-pyrazol-5-yl)urea, 1-(4-((1H-pyrazolopyrimidin-4-yl)oxy)-3-fluorophenyl)-3-(3-tert-butyl-1-cyclopentyl-1H-pyrazol-5-yl)urea, 1-(4-((1H-pyrazolopyrimidin-4-yl)oxy)phenyl)-3-(3-tert-butyl-thiazol-2-yl)urea, 1-(4-((1H-pyrazolopyrimidin-4-yl)oxy)phenyl)-3-(4-phenylthiazol-2-yl)urea or 1-(4-((1H-pyrazolopyrimidin-4-yl)oxy)phenyl)-3-(benzothiazol-2-yl)urea.

* * * * *